(12) United States Patent
Mintz

(10) Patent No.: US 7,858,744 B2
(45) Date of Patent: Dec. 28, 2010

(54) COMPOSITIONS, REAGENTS AND KITS FOR AND METHODS OF DIAGNOSING, MONITORING AND TREATING HORMONAL IMBALANCE

(75) Inventor: Liat Mintz, East Brunswick, NJ (US)

(73) Assignee: Dialean, Ltd. (IL)

( * ) Notice: Subject to any disclaimer, the term of this patent is extended or adjusted under 35 U.S.C. 154(b) by 55 days.

(21) Appl. No.: 11/591,649

(22) Filed: Nov. 1, 2006

(65) Prior Publication Data

US 2007/0099275 A1    May 3, 2007

Related U.S. Application Data

(60) Provisional application No. 60/733,090, filed on Nov. 3, 2005.

(51) Int. Cl.
*C07K 14/435* (2006.01)
*C07K 14/605* (2006.01)
(52) U.S. Cl. ...................... 530/350; 530/308
(58) Field of Classification Search ....................... None
See application file for complete search history.

(56) References Cited

U.S. PATENT DOCUMENTS

| 4,946,778 A | 8/1990 | Ladner et al. |
| 5,547,839 A | 8/1996 | Dower et al. |
| 6,110,707 A * | 8/2000 | Newgard et al. ............ 435/69.4 |
| 2007/0083334 A1* | 4/2007 | Mintz et al. .................... 702/19 |

FOREIGN PATENT DOCUMENTS

| EP | 0 242 236 B2 | | 8/1996 |
| WO | WO 98/35044 | | 8/1998 |
| WO | WO 01/36632 | * | 5/2001 |

OTHER PUBLICATIONS

Drucker et al., Journal of Biological Chemistry, 263:13475-13478, 1988.*
Wilson, I. et al., "The Structure Of An Antigenic Determinant In A Protein", Cell 37:767-778 (1984).
Sarkar et al., "Restriction-site PCR: A Direct Method Of Unknown Sequence Retrieval Adjacent To A Known Locus . . . ", PCR Methods Appl. 2:318-22 (1993).
Triglia, T. et al., "A Procedure For In Vitro Amplification Of DNA Segments That Lie Outside . . . ", Nucleic Acids Res. 16:8186 (1988).
Lagerstrom, M. et al., "Capture PCR: Efficient Amplification Of DNA Fragments Adjacent To A Known Sequence", PCR Methods Appl. 1:111-19 (1991).
Parker, J.D. et al., "Targeted Gene Walking Polymerase Chain Reaction", Nucleic Acids Res. 19:3055-60 (1991).
Murray, E. et al., "Codon Usage In Plant Genes", Nucleic Acids Res. 17:477-498 (1989).
Van Heeke et al., "Expression Of Human Asparagine Synthetase In *Escherichia Coli*", J. Biol. Chem. 264:5503-5509 (1989).
Brisson et al., "Expression Of A Bacterial Gene In Plants By Using A Viral Vector", Nature 310:511-514 (1984).
Takamatsu et al., "Expression Of Bacterial Chloramphenicol Acetyltransferase Gene In Tobacco Plants . . . ", EMBO J. 6:307-311 (1987).
Coruzzi et al., "Tissue-Specific And Light-Regulated Expression Of A Pea Nuclear Gene Encoding The Small Subunit . . . ", EMBO J. 3:1671-1679 (1984).
Broglie et al., "Light-Regulated Expression Of A Pea Ribulose-1,5-Bisphosphate Carboxylase . . . ", Science 224:838-843 (1984).
Winter, J. et al., "The Expression Of Heat Shock Protein And Cognate Genes During Plant Development", Results Probl. Cell Differ. 17:85-103 (1991).
Smith et al., "Molecular Engineering Of The Autographa Californica Nuclear Polyhedrosis Virus Genome . . . ", J. Virol. 46:584-593 (1983).
Engelhard, E.K. et al., "The Insect Tracheal System: A Conduit For The Systemic Spread Of Autographa . . . ", Proc. Nat. Acad. Sci. USA 91:3224-7 (1994).
Logan et al., "Adenovirus Tripartite Leader Sequence Enhances Translation Of mRNAs Late After Infection", Proc. Natl. Acad. Sci., USA 81:3655-59 (1984).
Scharf, D. et al., "Introduction: Heat Stress Promoters And Transcription Factors", Results Probl. Cell Differ. 20:125-62 (1994).
Bitter et al., "Expression And Secretion Vectors For Yeast", Meth. Enzymol. 153:516-544 (1987).
Wigler, M. et al., "Transfer Of Purified Herpes Virus Thymidine Kinase Gene To Cultured Mouse Cells", Cell 11:223-32 (1977).
Lowy, I. et al., "Isolation Of Transforming DNA: Cloning The Hamster APRT Gene", Cell 22:817-23 (1980).
Wigler, M. et al., "Transformation Of Mammalian Cells With An Amplifiable Dominant-Acting Gene", Proc. Natl. Acad. Sci. USA 77:3567-70 (1980).
F. Colbere-Garapin et al., "A New Dominant Hybrid Selective Marker For Higher Eukaryotic Cells", J. Mol. Biol. 150:1-14 (1981).
S.C. Hartman and R.C. Mulligan, "Two Dominant-Acting Selectable Markers For Gene Transfer Studies . . . ", Proc. Natl. Acad. Sci., USA, 85:8047-51 (1988).
C.A. Rhodes et al., "Transformation Of Maize By Electroporation Of Embryos", Methods Mol. Biol. 55:121-131 (1995).
Porath et al., "Immobilized Metal Ion Affinity Chromatography", Protein Expr. Purif. 3:263-281 (1992).
Saiki et al., "Analysis Of Enzymatically Amplified Beta-Globin And HLA-DQ . . . ", Nature, 324:163-166 (1986).
Cotton et al., "Reactivity Of Cytosine And Thymine In Single-Base-Pair Mismatches . . . ", Proc. Natl. Acad. Sci., USA, 85:4397-4401 (1988).
L.G. Kostrikis et al., "Spectral Genotyping Of Human Alleles", Science 279:1228-1229 (1998).

(Continued)

*Primary Examiner*—Marianne P Allen
(74) *Attorney, Agent, or Firm*—Potter Anderson & Corroon, LLP

(57) ABSTRACT

The present invention concerns ten novel variants of alternative splicing of the hormonal imbalance related genes.

2 Claims, 32 Drawing Sheets

OTHER PUBLICATIONS

Lee et al., Complexes Formed By (Pyrimidine)n (purine)n DNAs On Lowering The pH Are Three-Stranded, Nucl. Acids Res. 6:3073-3091 (1979).
Cooney et al., "Site-Specific Oligonucleotide Binding Represses Transcription Of The Human c-myc Gene in Vitro", Science 241:456-459 (1988).
Beal et al., "Second Structural Motif For Recognition Of DNA By Oligonucleotide-Directed Triple-Helix Formation", Science 251:1360 (1991).
Okano et al., "Myelin Basic Protein Gene And The Function Of Antisense RNA In Its Repression In Myelin-Deficient Mutant . . . ", J. Neurochem. 56:560-567 (1991).
Miller et al., "Retrovirus Packaging Cells", Human Gene Therapy, vol. 1, p. 5-14 (1990).
H.J. Mauceri et al., "Tumor Necrosis Factor a (TNF-a) Gene Therapy Targeted by Ionizing Radiation . . . ", Cancer Res. 56(19):4311-4314 (1996).
J. Merrifield, "The Synthesis Of A Tetrapeptide", J. Am. Chem. Soc. 85:2149-2154 (1963).
Koehler and Milstein, "Continuous Cultures Of Fused Cells Secreting Antibody Of Predefined Specificity", Nature 256:495-497 (1975).
Kozbor et al., "The Production Of Monoclonal Antibodies From Human Lymphocytes", Immunol. Today 4:72-79 (1983).
Cote et al., "Generation Of Human Monoclonal Antibodies Reactive With Cellular Antigens", Proc. Natl. Acad. Sci., USA, 80:2026-2030 (1983).
Cole et al., "Human Monoclonal Antibodies", Mol. Cell Bioch. 62:109-120 (1984).
Morrison et al., "Chimeric Human Antibody Molecules: Mouse Antigen-Binding Domains . . . ", Proc. Natl. Acad. Sci. USA 81:6851-6855 (1984).
Neuberger et al., "Recombinant Antibodies Possessing Novel Effector Functions", Nature 312:604-608 (1984).
Takeda et al., "Construction Of Chimeric Processed Immunoglobulin Genes Containing Mouse Variable . . . ", Nature, 314:452-454 (1985).
Orlandi et al., "Cloning Immunoglobulin Variable Domains For Expression By The Polymerase . . . ", Proc. Natl. Acad. Sci., USA, 86:3833-3837 (1989).
G. Winter and C. Milstein, "Man-Made Antibodies", Nature 349:293-299 (1991).
W.D. Huse et al., "Generation Of A Large Combinatorial Library Of The Immunoglobulin Repertoire In Phage Lambda", Science 256:1275-1281 (1989).
D.E. Maddox et al., "Elevated Serum Levels In Human Pregnancy Of A Molecule Immunochemically Similar . . . ", J. Exp. Med. 158:1211 (1983).
B. Holst et al., "Steric Hindrance Mutagenesis Versus Alanine Scan In Mapping Of Ligand Binding Sites . . . ", Mol. Pharmacol. 53:166-175 (1998).
Orskov, C. et al., Effect of Truncated Glucagon-Like Peptide-1 . . . , Endocrinology, vol. 123, No. 4, pp. 2009-2013, 1988.
Wang, Z. et al., Glucagon-like Peptide-1 . . . , J. Clin. Invest. Rapid Publication, vol. 95, pp. 417-421, Jan. 1995.
Adelhorst et al., Structure-Activity Studies of . . . , J. Biol. Chem., 269, 9, pp. 6275-6278, Mar. 4,1994.
Knudsen et al., Glucagon-Like Peptide-1-(9-36) Amide is a Major Metabolite . . . , European Journal Pharm. ,318, pp. 429-435, 1996.
Creutzfeldt, W.O. et al., Glucagonostatic Actions and Reductions of Fasting . . . , Diabetes Care, 19, 6, pp. 580-586, 1996.
Tang-Christensen, M. et al., Central administration of GLP-1-(7-36) amide . . . , Am J Physiol Regul Integr Comp Physiol 27, pp. R848-856, 1996.
Groger, G. et al., Ileal Carbohydrates Inhibit Cholinergically Stimulated . . . , Int Journal of Pancreatol, 22, 1, pp. 23-29, Aug. 1997.
Nauck, M.A. et al., Glucagon-like peptde 1 inhibition of gastric emptying . . . , Am J Physiol Endocrinol Metab., 273, pp. E981-988, 1997.
Wettergren, A. et al., Glucagon-like peptide-1 inhibits gastropancreatic . . . , Am. J. Physiol. Gastrointest. Liver Physiol., 275, pp. G984-992, 1998.
Buteau, J. et al., Glucagon-like peptide-1 promotes DNA synthesis, activates . . . , Diabetologia, 42, pp. 856-864, 1999.
Balkan, B et al., Portal GLP-1 Administration in Rats Augments the Insulin Response . . . , Am. Phy., 279, pp. R1449-1454, 2000.
Xiao, Q. et al.., Biological Activities of Glucagon-Like Peptide-1 Analogues in Vitro and in Vivo, Biochemistry, vol. 40, No. 9, pp. 2860-2869, 2001.
Vila Petroff, M.G. et al., Glucagon-Like Peptide-1 Increases cAMP but Fails to . . . , Circ. Res. 89, pp. 445-452, 2001.
Hui, H. et al., The Short Half-Life of GlucagonLlike Peptide-1 . . . , European J. of Endocrinology, 146, pp. 863-869, 2002.
Yamamoto H. et al., Glucagon-Like Peptide-1 Receptor Stimulation Increases Blood . . . , J. Clin. Invest. vol. 110, 1, pp. 43-52, Jul. 2002.
Perry, T. et al., Protection and Reversal of Excitotoxic Neuronal . . . , J. Pharmacol. Exp. Ther., vol. 302, No. 3, pp. 881-888, 2002.
MacDonald, P.E. et al., The Multiple Actions of GLP-1 on the Process of Glucose . . . , Diabetes vol. 51, Suppl 3, pp. S434-442, Dec. 2002.
Yamamoto, H. et al., Glucagon-like Peptide-1 Responsive Catecholamine . . . , The J Neurosci., 23, 7, pp. 2939-2946, Apr. 2003.
Drucker, D.J., Glucagon-like Peptides: Regulators of Cell Proliferation . . . , Mol. Endocrinol. 17, 2, pp. 161-171, 2003.
Vilsbøll, T. et al., Both GLP-1 and GIP are Insulintropic at Basal and Postprandial . . . , Regulatory Peptides, 114, pp. 115-121, 2003.
During, M.J. et al., Glucagon-Like Peptide-1 Receptor is involved . . . , Nat. Med., 9, pp. 1173-1179, 2003.
Vilsbøll T. et al., Incretins, Insulin Secretion and Type 2 Diabetes Mellitus, Diabetologia, 47, pp. 357-666, 2004.
Nikolaidis, L.A. et al., Recombinant Glucagon-Like Peptide-1 Increases Myocardial . . . , Circulation, 110, pp. 955-961, 2004.
Preitner, F. et al., Gluco-incretins Control Insulin Secretion at Multiple Levels as . . . , J. Clin. Invest., 113, pp. 635-645, 2004.
Holst, J.J. et al., The Incretin Approach for Diabetes Treatment, Diabetes, 53, Suppl. 3, pp. S197-204, 2004.
Bose, A.K. et al., Glucagon-Like Peptide 1 Can Directly Protect the Heart Against . . . , Diabetes, 54, pp. 146-151, 2005.
Dyachok, O. et al., Oscillations of Cyclic AMP in Hormone-Stimulated . . . , Nature, 439, 19, pp. 349-352, 2006.

* cited by examiner

Figure 1

```
SEQID20      1  MKSIYFVAGLFVMLVQGSWQRSLQDTEEKSRSFSASQADPLSDPDQMNED    50
                ||||||||||||||||||||||||||||||||||||||||||||||||||
SEQID21      1  MKSIYFVAGLFVMLVQGSWQRSLQDTEEKSRSFSASQADPLSDPDQMNED    50

SEQID20     51  KRHSQGTFTSDYSKYLDSRRAQDFVQWLMNTKRNRNNIAKRHDEFERHAE   100
                ||||||||||||||||||||||||||||||||||||||||||||||||||
SEQID21     51  KRHSQGTFTSDYSKYLDSRRAQDFVQWLMNTKRNRNNIAKRHDEFERHAE   100

SEQID20    101  GTFTS---DVSSYLEGQAAKE-FIAWLVKGRGRRDFPEEVAIVEELGRRH   146
                |||||    ..|..|:..||.. .:..|::
SEQID21    101  GTFTSVSQKRSPLLKNLAADMLMVLSLMR                        129

SEQID20    147  ADGSFSDEMNTILDNLAARDFINWLIQTKITDRK      180

SEQID21    130                                         129
```

Figure 2

```
SEQID22      MMAGMKIQLVCMLLLAFSSWSLCSDSEEEMKALEADFLTNMHTSKISKAHVPSWKMTLLN 60
SEQID24      MMAGMKIQLVCMLLLAFSSWSLCSDSEEEMKALEADFLTNMHTSK--------------- 45
SEQID23      MMAGMKIQLVCMLLLAFSSWSLCSDSEEEMKALEADFLTNMHTSKISKAHVPSWKMTLLN 60
             ********************************************   .: . : .

SEQID22      VCSLVNNLNSPAEETGEVHEEELVARRKLPTALDGFSLEAMLTIYQLHKICHSRAFQHWE 120
SEQID24      ------------------------------------------------------------
SEQID23      VCSLVNNLNSPAEETGEVHEEELVARRKLPTALDGFSLEAMLTIYQLHKICHSRAFQHWE 120
             .:   .. .:.:..:..   :   . .:: .. :  .:  :   .  . . : :.   .

SEQID22      LIQEDILDTGNDKNGKEEVIKRKIPYILKRQLYENKPRRPYILKRDSYYY 170
SEQID24      LIQEDILDTGNDKNGKEEVIKRKIPYILKRQLYENKPRRPYILKRDSYYY 95
SEQID23      LIQEDILDTGNDKNGKEEVIKRKIPYILKRQ--QATCARAV--------- 159
             *******************************  :  *.    . .:
```

Figure 3

```
SEQID25    1 MAAARLCLSLLLLSTCVALLLQPLLGAQGAPLEPVYPGDNATPEQMAQYA    50
             ||||||||||||||||||||||||||||||||||||||||||||||||||
SEQID26    1 MAAARLCLSLLLLSTCVALLLQPLLGAQGAPLEPVYPGDNATPEQMAQYA    50

SEQID25   51 ADLRRYINMLTR----------PRYGKRHKEDTLAFSEWGSPHAAVPREL    90
             ||||||||||||          ||||||||||||||||||||||||||||
SEQID26   51 ADLRRYINMLTRPSACPCCLFPPRYGKRHKEDTLAFSEWGSPHAAVPREL   100

SEQID25   91 SPLDL     95
             |||||
SEQID26  101 SPLDL    105
```

Figure 4

```
SEQID27    1 MESSRVRLLPLLGAALLLMLPLLGTRAQEDAELQPRALDIYSAVDDASHE     50
             ||||||||||||||||||||||||||||||||||||||||||||||||||
SEQID28    1 MESSRVRLLPLLGAALLLMLPLLGTRAQEDAELQPRALDIYSAVDDASHE     50

SEQID27   51 KELIEALQEVLKKLK-----------SKRVPIYEKKYGQVPMCDAGEQC     88
             |||: .:...|..|:           |.....|.:..|     ||.
SEQID28   51 KELV-GIPLALDPLELSPCLFSCTPPSSPHPHSYSQSQG------AGS     91

SEQID27   89 AVRKGARIGKLCDCPRGTSCNSFLLKCL    116
SEQID28   92                                 91
```

Figure 5

```
SEQID29    1 MRQAGRAALLAALLLLVQLCPGSSQRSPEAA----GVQDPSLRWSPGARN    46
             |||||||||||||||||||||||||||||:|    |. :|..| .|.|..
SEQID30    1 MRQAGRAALLAALLLLVQLCPGSSQRSPESALEPRGT-EPGWR-GPRAPL    48

SEQID29   47 QGGGARALLLLLAERFPRRAGPGRLGLGTA-GERPRRDNPSLSIDLTFHL    95
             ..|||...        ||.|.|    :||. |.|.........|:.
SEQID30   49 AAGGALPA--------PRGARP----IGTRDGRRAAAAGQPFSVH       81

SEQID29   96 LRTLLELARTQSQRERAEQNRIIFDSVGK    124
SEQID30   82                                81
```

Figure 6

```
SEQID31      1 MARFLTLCTWLLLLGPGLLATVRAECSQDCATCSYRLVRPADINFLACVM    50
                                                                  |
SEQID32      1                                                  M    1

SEQID31     51 ECEGKLPSLKIWETCKELLQLSKPELPQDGTSTLRENSKPEESHLLAKRY   100
               ||||||||||||||||||||||||||||||||||||||||||||||||||
SEQID32      2 ECEGKLPSLKIWETCKELLQLSKPELPQDGTSTLRENSKPEESHLLAKRY    51

SEQID31    101 GGFMKRYGGFMKKMDELYPMEPEEEANGSEILAKRYGGFMKKDAEEDDSL   150
               ||||||||||||||||||||||||||||||||||||||||||||||||||
SEQID32     52 GGFMKRYGGFMKKMDELYPMEPEEEANGSEILAKRYGGFMKKDAEEDDSL   101

SEQID31    151 ANSSDLLKELLETGDNRERSHHQDGSDNEEEVSKRYGGFMRGLKRSPQLE   200
               ||||||||||||||||||||||||||||||||||||||||||||||||||
SEQID32    102 ANSSDLLKELLETGDNRERSHHQDGSDNEEEVSKRYGGFMRGLKRSPQLE   151

SEQID31    201 DEAKELQKRYGGFMRRVGRPEWWMDYQKRYGGFLKRFAEALPSDEEGESY   250
               ||||||||||||||||||||||||||||||||||||||||||||||||||
SEQID32    152 DEAKELQKRYGGFMRRVGRPEWWMDYQKRYGGFLKRFAEALPSDEEGESY   201

SEQID31    251 SKEVPEMEKRYGGFMRF    267
               |||||||||||||||||
SEQID32    202 SKEVPEMEKRYGGFMRF    218
```

Figure 7

```
SEQID33    1 MCAERLGQFMTLALVLATFDPARGTDATNPPEGPQDRSSQQKGRLSLQNT    50
             ||||||||||||||||||||||||||||||||||||||||||||||||||
SEQID34    1 MCAERLGQFMTLALVLATFDPARGTDATNPPEGPQDRSSQQKGRLSLQNT    50

SEQID33   51 AEIQHCLVNAGDVGCGVFECFENNSCEIRGLHGICMTFLHNAGKFDAQGK   100
             ||||||||||||||||||||||||||||||||||||||||||||||||||
SEQID34   51 AEIQHCLVNAGDVGCGVFECFENNSCEIRGLHGICMTFLHNAGKFDAQGK   100

SEQID33  101 SFIKDALKCKAHALRHRFGCISRKCPAIREMVSQLQRECYLKHDLCAAAQ   150
             ||||||||||||||||||||||||||||||||||||||||||||||||||
SEQID34  101 SFIKDALKCKAHALRHRFGCISRKCPAIREMVSQLQRECYLKHDLCAAAQ   150

SEQID33  151 ENTRVIVEMIHFKDLLLHEPYVDLVNLLLTCGEEVKEAITHSVQVQCEQN   200
             ||||||||||||||||||||||||||||||||||||||||||||||||||
SEQID34  151 ENTRVIVEMIHFKDLLLHEPYVDLVNLLLTCGEEVKEAITHSVQVQCEQN   200

SEQID33  201 WGSLCSILSFCTSAIQKPPTAPPERQPQVDRTKLSRAHHGEAGHHLPEP-   249
             |||||||||||||||||||||||||||||||||||||||||..|..|...
SEQID34  201 WGSLCSILSFCTSAIQKPPTAPPERQPQVDRTKLSRAHHGVLGAKLKFSF   250

SEQID33  250 ---SSRETGRGAKGERGSKSHPNAHARGRVGGLGAQGPSGSSEWEDEQSE   296
               :.|....|..|.|...|..|.
SEQID34  251 LCGALRFRALGEGGGRSVISMCNF                            274

SEQID33  297 YSDIRR    302

SEQID34  275            274
```

Figure 8

```
SEQID35     1 MDPQTAPSRALLLLLFLHLAFLGGRSHPLGSPGSASDLETSGLQEQRNHL      50
              ||||||||||||||||||||||||||||||||||||||||||||||||||
SEQID36     1 MDPQTAPSRALLLLLFLHLAFLGGRSHPLGSPGSASDLETSGLQEQRNHL      50

SEQID35    51 QGKLSELQVEQTSLEPLQESPRPTGVWKSREVATEGIRGHRKMVLYTLRA     100
              ||||||||||||||||||||||||||||||||||||||||||||||||||
SEQID36    51 QGKLSELQVEQTSLEPLQESPRPTGVWKSREVATEGIRGHRKMVLYTLRA     100

SEQID35   101 PRSPKMVQGSGCFGRKMDRISSSSGLGCKVLRRH                     134
              |||||||||||||||||||||||||||||||  .:|
SEQID36   101 PRSPKMVQGSGCFGRKMDRISSSSGLGCK--GKHPLPPRPPSPIPVCDTV     148

SEQID35   135                          134

SEQID36   149 RVTLGFVVSGNHTL      162
```

Figure 9

```
SEQID37      1 MLRTESCRPRSPAGQVAAASPLLLLLLLLAWCAGACRGAPILPQGLQPEQ      50
               ||||||||||||||||||||||||||||||||||||||||||||||||||
SEQID38      1 MLRTESCRPRSPAGQVAAASPLLLLLLLLAWCAGACRGAPILPQGLQPEQ      50

SEQID37     51 QLQLWNEIDDTCSSFLSIDSQPQASNALEELCFMIMGMLPKPQEQDEKDN     100
               ||||||||||||||||||||||||||||||||||||||||||||||||||
SEQID38     51 QLQLWNEIDDTCSSFLSIDSQPQASNALEELCFMIMGMLPKPQEQDEKDN     100

SEQID37    101 TKRFLFHYSKTQKLGKSNVVSSVVHPLLQLVPHLHERRMKRFRVDEEFQS     150
               ||||||||||||||||||||                         |||||
SEQID38    101 TKRFLFHYSKTQKLGKSNVV-------------------------EEFQS     125

SEQID37    151 PFASQSRGYFLFRPRNGRRSAGFI    174
               |||||||||||||||||||||||
SEQID38    126 PFASQSRGYFLFRPRNGRRSAGFI    149
```

Figure 10A

```
SEQID1     1 ACAGAGCTTAGGACACAGAGCACATCAAAAGTTCCCAAAGAGGGCTTGCT    50
             |||||||||||||||||||||||||||||||||||||||||||||||||
SEQID2     1 ACAGAGCTTAGGACACAGAGCACATCAAAAGTTCCCAAAGAGGGCTTGCT    50

SEQID1    51 CTCTCTTCACCTGCTCTGTTCTACAGCACACTACCAGAAGACAGCAGAAA   100
             |||||||||||||||||||||||||||||||||||||||||||||||||
SEQID2    51 CTCTCTTCACCTGCTCTGTTCTACAGCACACTACCAGAAGACAGCAGAAA   100

SEQID1   101 TGAAAAGCATTTACTTTGTGGCTGGATTATTTGTAATGCTGGTACAAGGC   150
             |||||||||||||||||||||||||||||||||||||||||||||||||
SEQID2   101 TGAAAAGCATTTACTTTGTGGCTGGATTATTTGTAATGCTGGTACAAGGC   150

SEQID1   151 AGCTGGCAACGTTCCCTTCAAGACACAGAGGAGAAATCCAGATCATTCTC   200
             |||||||||||||||||||||||||||||||||||||||||||||||||
SEQID2   151 AGCTGGCAACGTTCCCTTCAAGACACAGAGGAGAAATCCAGATCATTCTC   200

SEQID1   201 AGCTTCCCAGGCAGACCCACTCAGTGATCCTGATCAGATGAACGAGGACA   250
             |||||||||||||||||||||||||||||||||||||||||||||||||
SEQID2   201 AGCTTCCCAGGCAGACCCACTCAGTGATCCTGATCAGATGAACGAGGACA   250

SEQID1   251 AGCGCCATTCACAGGGCACATTCACCAGTGACTACAGCAAGTATCTGGAC   300
             |||||||||||||||||||||||||||||||||||||||||||||||||
SEQID2   251 AGCGCCATTCACAGGGCACATTCACCAGTGACTACAGCAAGTATCTGGAC   300

SEQID1   301 TCCAGGCGTGCCCAAGATTTTGTGCAGTGGTTGATGAATACCAAGAGGAA   350
             |||||||||||||||||||||||||||||||||||||||||||||||||
SEQID2   301 TCCAGGCGTGCCCAAGATTTTGTGCAGTGGTTGATGAATACCAAGAGGAA   350

SEQID1   351 CAGGAATAACATTGCCAAACGTCACGATGAATTTGAGAGACATGCTGAAG   400
             |||||||||||||||||||||||||||||||||||||||||||||||||
SEQID2   351 CAGGAATAACATTGCCAAACGTCACGATGAATTTGAGAGACATGCTGAAG   400

SEQID1   401 GGACCTTTACCAGTGATGTAAGTTCTTATTTGGAAGGCCAAGCTGCCAAG   450
             ||||||||||||||
SEQID2   401 GGACCTTTACCAGTG-----------------------------------   415

SEQID1   451 GAATTCATTGCTTGGCTGGTGAAAGGCCGAGGAAGGCGAGATTTCCCAGA   500
                                                       |||||||||
SEQID2   416 -----------------------------------TTTCCCAGA   424

SEQID1   501 AGAGGTCGCCATTGTTGAAGAACTTGGCCGCAGACATGCTGATGGTTCTT   550
             |||||||.|||||||||||||||||||||.||||||||||||||||||||
SEQID2   425 AGAGGTCGCCATTGTTGAAGAACTTGGCCGCAGACATGCTGATGGTTCTT   474

SEQID1   551 TCTCTGATGAGATGAACACCATTCTTGATAATCTTGCCGCCAGGGACTTT   600
             |||||||||||||||||||||||||||||||||||||||||||||||||
SEQID2   475 TCTCTGATGAGATGAACACCATTCTTGATAATCTTGCCGCCAGGGACTTT   524

SEQID1   601 ATAAACTGGTTGATTCAGACCAAAATCACTGACAGGAAATAACTATATCA   650
             |||||||||||||||||||||||||||||||||||||||||||||||||
SEQID2   525 ATAAACTGGTTGATTCAGACCAAAATCACTGACAGGAAATAACTATATCA   574

SEQID1   651 CTATTCAAGATCATCTTCACAACATCACCTGCTAGCCACGTGGGATGTTT   700
             |||||||||||||||||||||||||||||||||||||||||||||||||
SEQID2   575 CTATTCAAGATCATCTTCACAACATCACCTGCTAGCCACGTGGGATGTTT   624
```

Figure 10B

```
SEQID1    701  GAAATGTTAAGTCCTGTAAATTTAAGAGGTGTATTCTGAGGCCACATTGC   750
               ||||||||||||||||||||||||||||||||||||||||||||||||||
SEQID2    625  GAAATGTTAAGTCCTGTAAATTTAAGAGGTGTATTCTGAGGCCACATTGC   674

SEQID1    751  TTTGCATGCCAATAAATAAATTTTCTTTTAGTGTTGTGTAGCCAAAAATT   800
               ||||||||||||||||||||||||||||||||||||||||||||||||||
SEQID2    675  TTTGCATGCCAATAAATAAATTTTCTTTTAGTGTTGTGTAGCCAAAAATT   724

SEQID1    801  ACAAATGGAATAAAGTTTTATCAAAATATTGCTAAAATATCAGCTTTAAA   850
               ||||||||||||||||||||||||||||||||||||||||||||||||||
SEQID2    725  ACAAATGGAATAAAGTTTTATCAAAATATTGCTAAAATATCAGCTTTAAA   774

SEQID1    851  ATATGAAAGTGCTAGATTCTGTTATTTTCTTCTTATTTTGGATGAAGTAC   900
               ||||||||||||||||||||||||||||||||||||||||||||||||||
SEQID2    775  ATATGAAAGTGCTAGATTCTGTTATTTTCTTCTTATTTTGGATGAAGTAC   824

SEQID1    901  CCCAACCTGTTTACATTTAGCGATAAAATTATTTTTCTATGATATAATTT   950
                |||||||||||||||||||||||||||||||||||||||||||||||||
SEQID2    825  CCCAACCTGTTTACATTTAGCGATAAAATTATTTTTCTATGATATAATTT   874

SEQID1    951  GTAAATGTAAATTATTCCGATCTGACATATCTGCATTATAATAATAGGAG  1000
               ||||||||||||||||||||||||||||||||||||||||||||||||||
SEQID2    875  GTAAATGTAAATTATTCCGATCTGACATATCTGCATTATAATAATAGGAG   924

SEQID1   1001  AATAGAAGAACTGGTAGCCACAGTGGTGAAATTGGAAAGAGAACTTTCTT  1050
               ||||||||||||||||||||||||||||||||||||||||||||||||||
SEQID2    925  AATAGAAGAACTGGTAGCCACAGTGGTGAAATTGGAAAGAGAACTTTCTT   974

SEQID1   1051  CCTGAAACCTTTGTCTTAAAAATACTCAGCTTTCAATGTATCAAAGATAC  1100
               ||||||||||||||||||||||||||||||||||||||||||||||||||
SEQID2    975  CCTGAAACCTTTGTCTTAAAAATACTCAGCTTTCAATGTATCAAAGATAC  1024

SEQID1   1101  AATTAAATAAAATTTTCAAGCTTCTTTA          1128
               ||||||||||||||||||||||||||||
SEQID2   1025  AATTAAATAAAATTTTCAAGCTTC             1048
```

Figure 11A

```
SEQID3    ---AGTTCACTCACTTTCAAAGCCAGCTGAAGGAAAGAGGAAGTGCTAGAGAGAGCCCCC   57
SEQID5    GATAGTTCACTCACTTTCAAAGCCAGCTGAAGGAAAGAGGAAGTGCTAGAGAGAGCCCCC   60
SEQID4    -ATAGTTCACTCACTTTCAAAGCCAGCTGAAGGAAAGAGGAAGTGCTAGAGAGAGCCCCC   59
             ********************************************************

SEQID3    TTCAGTGTGCTTCTGACTTTTACGGACTTGGCTTGTTAGAAGGCTGAAAGATGATGGCAG  117
SEQID5    TTCAGTGTGCTTCTGACTTTTACGGACTTGGCTTGTTAGAAGGCTGAAAGATGATGGCAG  120
SEQID4    TTCAGTGTGCTTCTGACTTTTACGGACTTGGCTTGTTAGAAGGCTGAAAGATGATGGCAG  119
          ************************************************************

SEQID3    GAATGAAAATCCAGCTTGTATGCATGCTACTCCTGGCTTTCAGCTCCTGGAGTCTGTGCT  177
SEQID5    GAATGAAAATCCAGCTTGTATGCATGCTACTCCTGGCTTTCAGCTCCTGGAGTCTGTGCT  180
SEQID4    GAATGAAAATCCAGCTTGTATGCATGCTACTCCTGGCTTTCAGCTCCTGGAGTCTGTGCT  179
          ************************************************************

SEQID3    CAGATTCAGAAGAGGAAATGAAAGCATTAGAAGCAGATTTCTTGACCAATATGCATACAT  237
SEQID5    CAGATTCAGAAGAGGAAATGAAAGCATTAGAAGCAGATTTCTTGACCAATATGCATACAT  240
SEQID4    CAGATTCAGAAGAGGAAATGAAAGCATTAGAAGCAGATTTCTTGACCAATATGCATACAT  239
          ************************************************************

SEQID3    CAAAGATTAGTAAAGCACATGTTCCCTCTTGGAAGATGACTCTGCTAAATGTTTGCAGTC  297
SEQID5    CAAAG-------------------------------------------------------  245
SEQID4    CAAAGATTAGTAAAGCACATGTTCCCTCTTGGAAGATGACTCTGCTAAATGTTTGCAGTC  299
          *****

SEQID3    TTGTAAATAATTTGAACAGCCCAGCTGAGGAAACAGGAGAAGTTCATGAAGAGGAGCTTG  357
SEQID5    ------------------------------------------------------------
SEQID4    TTGTAAATAATTTGAACAGCCCAGCTGAGGAAACAGGAGAAGTTCATGAAGAGGAGCTTG  359

SEQID3    TTGCAAGAAGGAAACTTCCTACTGCTTTAGATGGCTTTAGCTTGGAAGCAATGTTGACAA  417
SEQID5    ------------------------------------------------------------
SEQID4    TTGCAAGAAGGAAACTTCCTACTGCTTTAGATGGCTTTAGCTTGGAAGCAATGTTGACAA  419

SEQID3    TATACCAGCTCCACAAAATCTGTCACAGCAGGGCTTTTCAACACTGGGAGTTAATCCAGG  477
SEQID5    -----------------------------------------------TTAATCCAGG    255
SEQID4    TATACCAGCTCCACAAAATCTGTCACAGCAGGGCTTTTCAACACTGGGAGTTAATCCAGG  479
                                                         **********

SEQID3    AAGATATTCTTGATACTGGAAATGACAAAAATGGAAAGGAAGAAGTCATAAAGAGAAAAA  537
SEQID5    AAGATATTCTTGATACTGGAAATGACAAAAATGGAAAGGAAGAAGTCATAAAGAGAAAAA  315
SEQID4    AAGATATTCTTGATACTGGAAATGACAAAAATGGAAAGGAAGAAGTCATAAAGAGAAAAA  539
          ************************************************************

SEQID3    TTCCTTATATTCTGAAACGGCAGC--------------------TCTATGAGAATAAACCC  578
SEQID5    TTCCTTATATTCTGAAACGGCAGC--------------------TGTATGAGAATAAACCC  356
SEQID4    TTCCTTATATTCTGAAACGGCACCAGGCCACATGTGCTCGAGCTGTATGAGAATAAACCC  599
          ***********************                    ****************

SEQID3    AGAAGACCCTACATACTCAAAACAGATTCTTACTATTACTGAGAGAATAAATCATTTATT  638
SEQID5    AGAAGACCCTACATACTCAAAAGAGATTCTTACTATTACTGAGAGAATAAATCATTTATT  416
SEQID4    AGAAGACCCTACATACTCAAAAGAGATTCTTACTATTACTGA------------------  641
          **********************  ******************
```

Figure 11B

```
SEQID3      TACATGTGATTGTGATTCATCATCCCTTAATTAAATATCAAATTATATTTGTGTGAAAAT  698
SEQID5      TACATGTGATTGTGATTCATCATCCCTTAATTAAATATCAAATTATATTTGTGTGAAAAT  476
SEQID4      ------------------------------------------------------------

SEQID3      GTGACAAACACACTTATCTGTCTCTTCTACAATTGTGGTTTATTGAATGTGATTTTTCTG  758
SEQID5      GTGACAAACACACTTATCTGTCTCTTCTACAATTGTGGTTTATTGAATGTGATTTTTCTG  536
SEQID4      ------------------------------------------------------------

SEQID3      CACTAATATAAATTAGACTAAGTGTTTTCAAATAAATCTAAATCTTCAGCATGATGTGTT  818
SEQID5      CACTAATATAAATTAGACTAAGTGTTTTCAAATAAATCTAAATCTTCAGCATGATGTGTT  596
SEQID4      ------------------------------------------------------------

SEQID3      GTGTATAATTGGAGTAGATATTAATTAAGTCACCTGTATAATGTTTTGTAATTTTGCAAA  878
SEQID5      GTGTATAATTGGAGTAGATATTAATTAAGTCACCTGTATAATGTTTTGTAATTTTGCAAA  656
SEQID4      ------------------------------------------------------------

SEQID3      ACATATCTTGAGTTGTTTAAACAGTCAAAATGTTTGATATTTTATACCAGCTTATGAGCT  938
SEQID5      ACATATCTTGAGTTGTTTAAACAGTCAAAATGTTTGATATTTTATACCAGCTTATGAGCT  716
SEQID4      ------------------------------------------------------------

SEQID3      CAAAGTACTACAGCAAAGCCTAGCCTGCATATCATTCACCCAAAACAAAGTAATAGCGCC  998
SEQID5      CAAAGTACTACAGCAAAGCCTAGCCTGCATATCATTCACCCAAAACAAAGTAATAGCGCC  776
SEQID4      ------------------------------------------------------------

SEQID3      TCTTTTATTATTTTGACTGAATGTTTTATGGAATTGAAAGAAACATACGTTCTTTTCAAG 1058
SEQID5      TCTTTTATTATTTTGACTGAATGTTTTATGGAATTGAAAGAAACATACGTTCTTTTCAAG  836
SEQID4      ------------------------------------------------------------

SEQID3      ACTTCCTCATGAATCTCTCAATTATAGGAAAAGTTATTGTGATAAAATAGGAACAGCTGA 1118
SEQID5      ACTTCCTCATGAATCTCTCAATTATAGGAAAAGTTATTGTGATAAAATAGGAACAGCTGA  896
SEQID4      ------------------------------------------------------------

SEQID3      AAGATTGATTAATGAACTATTGTTAATTCTTCCTATTTTAATGAATGACATTGAACTGAA 1178
SEQID5      AAGATTGATTAATGAACTATTGTTAATTCTTCCTATTTTAATGAATGACATTGAACTGAA  956
SEQID4      ------------------------------------------------------------

SEQID3      TTTTTTGTCTGTTAAATGAACTTGATAGCTAATAAAAAGACAACTAGCCATCAAAAAAAA 1238
SEQID5      TTTTTTGTCTGTTAAATGAACTTGATAGCTAATAAAAAGACAACTAGCCATCAAAAAAAA 1016
SEQID4      ------------------------------------------------------------

SEQID3      AAA 1241
SEQID5      AA- 1018
SEQID4      ---
```

Figure 12

```
SEQID6      1  ATGGCTGCCGCACGCCTCTGCCTCTCCCTGCTGCTCCTGTCCACCTGCG      49
               ||||||||||||||||||||||||||||||||||||||||||||||||
SEQID7      1  GATGGCTGCCGCACGCCTCTGCCTCTCCCTGCTGCTCCTGTCCACCTGCG     50

SEQID6     50  TGGCTCTGTTACTACAGCCACTGCTGGGTGCCCAGGGAGCCCCACTGGAG      99
               ||||||||||||||||||||||||||||||||||||||||||||||||||
SEQID7     51  TGGCTCTGTTACTACAGCCACTGCTGGGTGCCCAGGGAGCCCCACTGGAG    100

SEQID6    100  CCAGTGTACCCAGGGGACAATGCCACACCAGAGCAGATGGCCCAGTATGC    149
               ||||||||||||||||||||||||||||||||||||||||||||||||||
SEQID7    101  CCAGTGTACCCAGGGGACAATGCCACACCAGAGCAGATGGCCCAGTATGC    150

SEQID6    150  AGCTGATCTCCGTAGATACATCAACATGCTGACCAGGCCT----------    189
               ||||||||||||||||||||||||||||||||||||||||
SEQID7    151  AGCTGATCTCCGTAGATACATCAACATGCTGACCAGGCCTAGTGCTTGCC    200

SEQID6    190  --------------------AGGTATGGGAAAAGACACAAAGAGGACACG    219
                                   ||||||||||||||||||||||||||||||
SEQID7    201  CCTGCTGCCTCTTCCCTCCCAGGTATGGGAAAAGACACAAAGAGGACACG    250

SEQID6    220  CTGGCCTTCTCGGAGTGGGGGTCCCCGCATGCTGCTGTCCCCAGGGAGCT    269
               ||||||||||||||||||||||||||||||||||||||||||||||||||
SEQID7    251  CTGGCCTTCTCGGAGTGGGGGTCCCCGCATGCTGCTGTCCCCAGGGAGCT    300

SEQID6    270  CAGCCCGCTGGACTTATAATGCCACCTTCTGTCTCCTACGACTCCATGAG    319
               ||||||||||||||||||||||||||||||||||||||||||||||||||
SEQID7    301  CAGCCCGCTGGACTTATAATGCCACCTTCTGTCTCCTACGACTCCATGAG    350

SEQID6    320  CAGCGCCAGCCCAGCTCTCCCCTCTGCACCCTTGGCTCTGGCCAAAGCTT    369
               ||||||||||||||||||||||||||||||||||||||||||||||||||
SEQID7    351  CAGCGCCAGCCCAGCTCTCCCCTCTGCACCCTTGGCTCTGGCCAAAGCTT    400

SEQID6    370  GCTCCCTGCTCCCACACAGGCTCAATAAAGCAAGTCAAAGCCAAAAAAAA    419
               ||||||||||||||||||||||||||||||||||||||||||||||||||
SEQID7    401  GCTCCCTGCTCCCACACAGGCTCAATAAAGCAAGTCAAAGCCAAAAAAAA    450

SEQID6    420  A      420
SEQID7    451         450
```

Figure 13A

```
SEQID8        1  GGTTGACCCGGGCCCTCCTCCACACCCCCTTCCTTCTTCGCCTCCTCCCT   50
SEQID9        1                                                         0

SEQID8       51  CTTTCCTGCACGGGGGCTCGGGCTCACTATAAAAGGTGGGAGCGCGTGGT  100
SEQID9        1                                                         0

SEQID8      101  GCCCCAGCAACGACGAGTTTCAGAACGATGGAGAGCTCCCGCGTGAGGCT  150
                             ||||||||||||||||||||||||||||||||||||||||||
SEQID9        1           AACGACGAGTTTCAGAACGATGGAGAGCTCCCGCGTGAGGCT   42

SEQID8      151  GCTGCCCCTCCTGGGCGCCGCCCTGCTGCTGATGCTACCTCTGTTGGGTA  200
                 ||||||||||||||||||||||||||||||||||||||||||||||||||
SEQID9       43  GCTGCCCCTCCTGGGCGCCGCCCTGCTGCTGATGCTACCTCTGTTGGGTA   92

SEQID8      201  CCCGTGCCCAGGAGGACGCCGAGCTCCAGCCCCGAGCCCTGGACATCTAC  250
                 ||||||||||||||||||||||||||||||||||||||||||||||||||
SEQID9       93  CCCGTGCCCAGGAGGACGCCGAGCTCCAGCCCCGAGCCCTGGACATCTAC  142

SEQID8      251  TCTGCCGTGGATGATGCCTCCCACGAGAAGGAGCT---------------  285
                 |||||||||||||||||||||||||||||||||||
SEQID9      143  TCTGCCGTGGATGATGCCTCCCACGAGAAGGAGCTGGTCGGTATTCCCCT  192

SEQID8      286  --------------------------------------------------  285
SEQID9      193  CGCTCTCGACCCCCTTGAGCTGTCGCCTTGTCTCTTCTCTTGCACGCCTC  242

SEQID8      286  --------------------------------------------------  285
SEQID9      243  CCTCCTCCCCCCACCCCCACTCCTATTCCCAGAGTCAGGGCGCGGGGAGC  292

SEQID8      286  --------------------------------------------------  285
SEQID9      293  TGAGCGCAACGCCCAGCCACCCACTGCCATCCGAAGAGCGTCTCGAGCTC  342

SEQID8      286  --------------------------------------------------  285
SEQID9      343  ACGGGCTCCTGGCAGTCTGTTGAGCGAATCCCTCATCCCGGCCCCTCTGA  392

SEQID8      286  --------------------------------------------------  285
SEQID9      393  GCAACAGGGACCCCAGCGGCTCAGAGACCCGCGGTCAGTACCTGGGACAG  442

SEQID8      286  --------------------------------------------------  285
SEQID9      443  CGTCCGCTAAGTTTCCACCCCTCGACCATTCCCTGTGTCCGCGGAGTCCC  492

SEQID8      286  --------------------------------------------------  285
SEQID9      493  ACCGCAGAGTGCGTGTGGGTCCGGGGCTCCTTATAACTAGGGCTGGAAGT  542

SEQID8      286  --------------------------------------------------  285
SEQID9      543  GCGCACCTGGGCTGGGCTCGCAGCCAAGGCGGCAACTTCAGGCTCCGAAG  592
```

Figure 13B

```
SEQID8    286 ------------GATCGAAGCGCTGCAAGAAGTCTTGAAGAAGCTCAAGA    323
              ||||||||||||||||||||||||||||||||||||||
SEQID9    593 CGGTGTGTTGCAGATCGAAGCGCTGCAAGAAGTCTTGAAGAAGCTCAAGA    642

SEQID8    324 GTAAACGTGTTCCCATCTATGAGAAGAAGTATGGCCAAGTCCCCATGTGT    373
              ||||||||||||||||||||||||||||||||||||||||||||||||||
SEQID9    643 GTAAACGTGTTCCCATCTATGAGAAGAAGTATGGCCAAGTCCCCATGTGT    692

SEQID8    374 GACGCCGGTGAGCAGTGTGCAGTGAGGAAAGGGGCAAGGATCGGGAAGCT    423
              ||||||||||||||||||||||||||||||||||||||||||||||||||
SEQID9    693 GACGCCGGTGAGCAGTGTGCAGTGAGGAAAGGGGCAAGGATCGGGAAGCT    742

SEQID8    424 GTGTGACTGTCCCCGAGGAACCTCCTGCAATTCCTTCCTCCTGAAGTGCT    473
              ||||||||||||||||||||||||||||||||||||||||||||||||||
SEQID9    743 GTGTGACTGTCCCCGAGGAACCTCCTGCAATTCCTTCCTCCTGAAGTGCT    792

SEQID8    474 TATGAAGGGCGTCCATTCTCCTCCATACATCCCCATCCCTCTACTTTCC    523
              ||||||||||||||||||||||||||||||||||||||||||||||||||
SEQID9    793 TATGAAGGGCGTCCATTCTCCTCCATACATCCCCATCCCTCTACTTTCC    842

SEQID8    524 CCAGAGGACCACACCTTCCTCCCTGGAGTTTGGCTTAAGCAACAGATAAA    573
              ||||||||||||||||||||||||||||||||||||||||||||||||||
SEQID9    843 CCAGAGGACCACACCTTCCTCCCTGGAGTTTGGCTTAAGCAACAGATAAA    892

SEQID8    574 GTTTTTATTTTCCTCTGAAGGGAAAGGCTCTTTTCCTGCTGTTTCAAAA    623
              ||||||||||||||||||||||||||||||||||||||||||||||||||
SEQID9    893 GTTTTTATTTTCCTCTGAAGGGAAAGGCTCTTTTCCTGCTGTTTCAAAA    942

SEQID8    624 ATAAAAGAACACATTAGATGTTACTGTGTGAAGAATAATGCCTTGTATGG    673
              ||||||||||||||||||||||||||||||||||||||||||||||||||
SEQID9    943 ATAAAAGAACACATTAGATGTTACTGTGTGAAGAATAATGCCTTGTATGG    992

SEQID8    674 TGTTGATACGTGTGTGAAGTATTCTTATTTTATTTGTCTGACAAACTCTT    723
              ||||||||||||||||||||||||||||||||||||||||||||||||||
SEQID9    993 TGTTGATACGTGTGTGAAGTATTCTTATTTTATTTGTCTGACAAACTCTT    1042

SEQID8    724 GTGTACCTTTGTGTAAAGAAGGGAAGCTTTGTTTGAAAATTGTATTTTTG    773
              ||||||||||||||||||||||||||||||||||||||||||||||||||
SEQID9    1043 GTGTACCTTTGTGTAAAGAAGGGAAGCTTTGTTTGAAAATTGTATTTTTG   1092

SEQID8    774 TATGTGGCATGGCAGAATGAAAATTAGATCTAGCTAATCTCGGTAGATGT    823
              ||||||||||||||||||||||||||||||||||||||||||||||||||
SEQID9    1093 TATGTGGCATGGCAGAATGAAAATTAGATCTAGCTAATCTCGGTAGATGT   1142

SEQID8    824 CATTACAACCTGGAAAATAAATCACCCTAAGTGACACAAATTGAAGCATG    873
              ||||||||||||||||||||||||||||||||||||||||||||||||||
SEQID9    1143 CATTACAACCTGGAAAATAAATCACCCTAAGTGACACAAATTGAAGCATG   1192

SEQID8    874 TACAAATTATACATAATAAAGTGTTTTTAATAATT               908
              ||||||||||||||||||||||||||||||||||
SEQID9    1193 TACAAATTATACATAATAAAGTGTTTTTAATAAT                1226
```

Figure 14A

```
SEQID10       1                                                          0

SEQID11       1  TGCGTCCAGTGCTGCTTCCAGCGCTAGCCCCAGGGGCACGAAGGCTGGTG       50

SEQID10       1                                                          0

SEQID11      51  TAGGGAGGTGCGCCCCTCCGGGGGCCCGCCAGCCGTCAGACTCGAAGCTG      100

SEQID10       1                                                          0

SEQID11     101  TGGCTGTCATTGCTTCTACAATCAGTGCATGTTCTTCGCTGACGTCAGTC      150

SEQID10       1                                AGCCCCGGGACAGACCC          17
                                                |||||||||||||||||
SEQID11     151  CCAGCTGTCCTGGCACTATATAAGGCTGGCGACAGCCCCGGGACAGACCC      200

SEQID10      18  TGTGTTCCCCAAGGCGTCTTCAGCCTGCCCCGAGGGACAGAGACTGGAGC       67
                 |:|||||||||||||||||||||||||||||||||||||||||||||||||
SEQID11     201  TGTGTTCCCCAAGGCGTCTTCAGCCTGCCCCGAGGGACAGAGACTGGAGC      250

SEQID10      68  TCAATCTTGGACCGTACAGACGCTCGCCGACAACCTGGCCGGCGGCACCA      117
                 ||||||||||||||||||||:|||||||||||||||||||||||||||||
SEQID11     251  TCAATCTTGGACCGTACAGACGCTCGCCGACAACCTGGCCGGCGGCACCA      300

SEQID10     118  TGAGGCACGCGGGACGCGCAGCGCTGCTGGCCGCGCTGCTGCTCCTGGTA      167
                 |||||||||||||||||||||||||||||  |||||||||||||||||||
SEQID11     301  TGAGGCAGGCGGGACGCGCAGCGCTGCTGGCCGCGCTGCTGCTCCTGGTA      350

SEQID10     168  CAGCTGTGCCCTGGGAGCAGCCAGAGGAGCCCCGAGGCGGCCGGGGTCCA      217
                 ||||||||||||||||||||||||||||||
SEQID11     351  CAGCTGTGCCCTGGGAGCAGCCAGAGGAGC--------------------      380

SEQID10     218  GGACCCGAGTCTGCGCTGGAGCCCCGGGGCACGGAACCAGGGTGGCGGGG      267
                    ||||||||||||||||||||||||||||||||||||||||||||||
SEQID11     381  ---CCCGAGTCTGCGCTGGAGCCCCGGGGCACGGAACCAGGGTGGCGGGG      427

SEQID10     268  CCCGCGCGCTCCTCTTGCTGCTGGCGGAGCGCTTCCCGCGCCGCGCGGGG      317
                 ||||||||||||||||||||||||||| ||||||||||||||||||||||
SEQID11     428  CCCGCGCGCTCCTCTTGCTGCTGGCGGAGCGCTTCCCGCGCCGCGCGGGG      477

SEQID10     318  CCCGGCCGATTGGGACTCGGGACGGCAGGCGAGCGGCCGCGGCGGGACAA      367
                 ||||||||||||||||||||||||||||||||||| ||||||||||||||
SEQID11     478  CCCGGCCGATTGGGACTCGGGACGGCAGGCGAGCGGCCGCGGCGGGACAA      527

SEQID10     368  CCCTTCTCTGTCCATTGACCTCACCTTTCACCTGCTGCGGACCCTGCTGG      417
                 |||||||||:||||||||||||||||||||||||||||||||||||||||
SEQID11     528  CCCTTCTCTGTCCATTGACCTCACCTTTCACCTGCTGCGGACCCTGCTGG      577

SEQID10     418  AGCTGGCGCGGACGCAGAGCCAGCGGGAGCGCGCCGAGCAGAACCGCATC      467
                 |||||||||||||||||||||||||||||||||||||||||||:||||||
SEQID11     578  AGCTGGCGCGGACGCAGAGCCAGCGGGAGCGCGCCGAGCAGAACCGCATC      627

SEQID10     468  ATATTCGACTCGGTGGGCAAGTGATGGCCCGGTTTGGGGCTGCGAAAACG      517
                 |||||||||||||||||||||:|||||||||||||||| |||||||||||
SEQID11     628  ATATTCGACTCGGTGGGCAAGTGATGGCCCGGTTTGGGGCTGCGAAAACG      677
```

Figure 14B

```
SEQID10      518  TTGACCCCTTTCCCCCACCCCAGAGTTGGGATGCGGGGCAGAGCCACCAG    567
                  ||||||||||||||||||||||||||||||||||||||||||||||||||
SEQID11      678  TTGACCCCTTTCCCCCACCCCAGAGTTGGGATGCGGGGCAGAGCCACCAG    727

SEQID10      568  GGCACTGTCTGCGTGACTATTTTTTAATAAAAGTACTGAAGACCCGTT     615
                  ||||||||||||||||||||||||||||||||||||||||||||||||
SEQID11      728  GGCACTGTCTGCGTGACTATTTTTTAATAAAAGTACTGAAGACCCGTT     775
```

Figure 15A

```
SEQID12      1 CGGCGAGGGTCCTGCCGAGGGACCCGTTCTGCGCCCAGGCAGGCTCGAAC   50

SEQID13      1                                                         0

SEQID12     51 CACGCGTCCCTCTCTCCTCGCAGTCCATGGCGCGGTTCCTGACACTTTGC  100
                                                                 |
SEQID13      1                                                  C    1

SEQID12    101 ACTTGGCTGCTGTTGCTCGGCCCCGGGCTCCTGGCGACCGTGCGGGCCGA  150
                || ||.|||..||  |  |.||||. |||||.|.||     |.|||
SEQID13      2 AC-TGACTGAAGT--C-CTGCCCT-GGCTCTTAGC-----TTCGG---    36

SEQID12    151 ATGCAGCCAGGATTGCGCGACGTGCAGCTACCGCCTAGTGCGCCCGGCCG  200
                ||||. !||||||...|.|                |.|.||
SEQID13     37 ---------GGATC-CGCGACTATCTG------------GGGACC-----   59

SEQID12    201 ACATCAACTTCCTGGCTTGCGTAATGGAATGTGAAGGTAAACTGCCTTCT  250
                             ||||||||||||||||||||||||||||||||||||
SEQID13     60 -------------GGCTTGCGTAATGGAATGTGAAGGTAAACTGCCTTCT   96

SEQID12    251 CTGAAAATTTGGGAAACCTGCAAGGAGCTCCTGCAGCTGTCCAAACCAGA  300
                ||||||||||||||||||||||||||||||||||||||||||||||||||
SEQID13     97 CTGAAAATTTGGGAAACCTGCAAGGAGCTCCTGCAGCTGTCCAAACCAGA  146

SEQID12    301 GCTTCCTCAAGATGGCACCAGCACCCTCAGAGAAAATAGCAAACCGGAAG  350
                ||||||||||||||||||||||||||||||||||||||||||||||||||
SEQID13    147 GCTTCCTCAAGATGGCACCAGCACCCTCAGAGAAAATAGCAAACCGGAAG  196

SEQID12    351 AAAGCCATTTGCTAGCCAAAAGGTATGGGGGCTTCATGAAAAGGTATGGA  400
                |||||||||:||||||||||||||||||||||||||||||||||||||||
SEQID13    197 AAAGCCATTTGCTAGCCAAAAGGTATGGGGGCTTCATGAAAAGGTATGGA  246

SEQID12    401 GGCTTCATGAAGAAAATGGATGAGCTTTATCCCATGGAGCCAGAAGAAGA  450
                ||||||||||||||||||||||||||||||||||||||||||||||||||
SEQID13    247 GGCTTCATGAAGAAAATGGATGAGCTTTATCCCATGGAGCCAGAAGAAGA  296

SEQID12    451 GGCCAATGGAAGTGAGATCCTCGCCAAGCGGTATGGGGGCTTCATGAAGA  500
                ||||||||||||||||||||||||||||||||||||||||||||||||||
SEQID13    297 GGCCAATGGAAGTGAGATCCTCGCCAAGCGGTATGGGGGCTTCATGAAGA  346

SEQID12    501 AGGATGCAGAGGAGGACGACTCGCTGGCCAATTCCTCAGACCTGCTAAAA  550
                ||||||||||||||||||||||||:|||||||||||||||||||||||||
SEQID13    347 AGGATGCAGAGGAGGACGACTCGCTGGCCAATTCCTCAGACCTGCTAAAA  396

SEQID12    551 GAGCTTCTGGAAACAGGGGACAACCGAGAGCGTAGCCACCACCAGGATGG  600
                ||||||||||||||||||||||||||||||||||||||||||||||||||
SEQID13    397 GAGCTTCTGGAAACAGGGGACAACCGAGAGCGTAGCCACCACCAGGATGG  446

SEQID12    601 CAGTGATAATGAGGAAGAAGTGAGCAAGAGATATGGGGGCTTCATGAGAG  650
                |||:|||||||||||||||||||||||||.||||||||||||||||||||
SEQID13    447 CACTGATAATGAGGAAGAAGTGAGCAAGAGATATGGGGGCTTCATGAGAG  496

SEQID12    651 GCTTAAAGAGAAGCCCCCAACTGGAAGATGAAGCCAAAGAGCTGCAGAAG  700
                |.||||||||||||||||||||||||||||||||||||||||||||||||
SEQID13    497 GCTTAAAGAGAAGCCCCCAACTGGAAGATGAAGCCAAAGAGCTGCAGAAG  546
```

Figure 15B

```
SEQID12    701  CGATATGGGGGCTTCATGAGAAGAGTAGGTCGCCCAGAGTGGTGGATGGA   750
                |||||||||||||||||||||||||||||||||||||||||||||||||
SEQID13    547  CGATATGGGGGCTTCATGAGAAGAGTAGGTCGCCCAGAGTGGTGGATGGA   596

SEQID12    751  CTACCAGAAACGGTATGGAGGTTTCCTGAAGCGCTTTGCCGAGGCTCTGC   800
                |||||||||||||||||||||||||||||||||||||||||||||||||
SEQID13    597  CTACCAGAAACGGTATGGAGGTTTCCTGAAGCGCTTTGCCGAGGCTCTGC   646

SEQID12    801  CCTCCGACGAAGAAGGCGAAAGTTACTCCAAAGAAGTTCCTGAAATGGAA   850
                ||||||||||||||||||||||||||||||||||||||||||||||||| 
SEQID13    647  CCTCCGACGAAGAAGGCGAAAGTTACTCCAAAGAAGTTCCTGAAATGGAA   696

SEQID12    851  AAAAGATACGGAGGATTTATGAGATTTTAATATTTTTCCCACTAGTGGCC   900
                |||||||||||||||||||||||||||||||||||||||||||||||||
SEQID13    697  AAAAGATACGGAGGATTTATGAGATTTTAATATTTTTCCCACTAGTGGCC   746

SEQID12    901  CCAGGCCCCAGCAAGCCTCCCTCCATCCTCCAGTGGGAAACTGTTGATGG   950
                |||||||||||||||||||||||||||||||||||||||||||||||||
SEQID13    747  CCAGGCCCCAGCAAGCCTCCCTCCATCCTCCAGTGGGAAACTGTTGATGG   796

SEQID12    951  TGTTTTATTGTCATGTGTTGCTTGCCTTGTATAGTTGACTTCATTGTCTG  1000
                |||||||||||||||||||||||||||||||||||||||||||||||||
SEQID13    797  TGTTTTATTGTCATGTGTTGCTTGCCTTGTATAGTTGACTTCATTGTCTG   846

SEQID12   1001  GATAACTATACAACCTGAAAACTGTCATTTCAGGTTCTGTGCTCTTTTTG  1050
                |||||||||||||||||||||||||||||||||||||||||||||||||
SEQID13    847  GATAACTATACAACCTGAAAACTGTCATTTCAGGTTCTGTGCTCTTTTTG   896

SEQID12   1051  GAGTCTTTAAGCTCAGTATTAGTCTATTGCAGCTATCTCGTTTTCATGCT  1100
                |||||||||||||||||||||||||||||||||||||||||||||||||
SEQID13    897  GAGTCTTTAAGCTCAGTATTAGTCTATTGCAGCTATCTCGTTTTCATGCT   946

SEQID12   1101  AAAATAGTTTTTGTTATCTTGTCTCTTATTTTTGACAAACATCAATAAAT  1150
                |||||||||||||||||||||||||||||||||||||||||||||||||
SEQID13    947  AAAATAGTTTTTGTTATCTTGTCTCTTATTTTTGACAAACATCAATAAAT   996

SEQID12   1151  GCTTACTTGTATATAGAGATAATAAACCTATTACCCCAAGTGCAAAAAAA  1200
                ||||||||||||||||||||||||||||||||||||||||||||.||||
SEQID13    997  GCTTACTTGTATATAGAGATAATAAACCTATTACCCCAAGTGCATAAAAA  1046

SEQID12   1201  AAAAAAAAAAAAAAAAAAAAAAAAAAAAAAAAAAAAAAA            1239
                ||......||
SEQID13   1047  AACTTGTAA                                          1055
```

Figure 16A

```
SEQID14       1  TTTCTCCTTCCCTCCACGGGCCGGGTGAGAAAGTAGCCGGGGGCTATCCC    50
SEQID15       1                                                          0

SEQID14      51  GACCCGGCGGTTCTTGGGGAGCGGGCCCGAACAAGAAAAGGGAGGAGATGG   100
SEQID15       1                                                          0

SEQID14     101  AGATAACTTCCCCGGATTTAGCTTTTTTGTCTTTGTTTTTGTTCTCACCA   150
SEQID15       1                                                          0

SEQID14     151  CTTCCATCGGATGACTGGAGAGTAAAAGGGAACCCGGAGCGGGTGGCGA    200
SEQID15       1                                                          0

SEQID14     201  GCAGCGCTTTGAGAAAATGCAGGAGTGTGTTTGGAGACGCGTAAAGTTGC   250
SEQID15       1                                                          0

SEQID14     251  CTTTCAAGCTCTGGCCTCCGGGCACGCGATGCTCCGCGGCGGGCTGACTC   300
SEQID15       1                                                          0

SEQID14     301  AGGGCTGCCTTGGGCCTCCCTGCCACCCTCCTGGAAATGATGCAAGTCCT   350
SEQID15       1                                                          0

SEQID14     351  GACTGTCACCTGGATCCCTGCAGCCCAGCCTGGAATGCGTCTGGATTAGG   400
SEQID15       1                                                          0

SEQID14     401  GGAAAGACGAGAAACGACACTCCAGGTGTTGCACGGCCCACCAAAGCGGG   450
SEQID15       1                                                          0

SEQID14     451  AAGATAGGGCAGTTGCTCAGACCAAATACTGTATCTAGTGCTTCTGCTCC   500
SEQID15       1                                                          0

SEQID14     501  TATCTTCAATCGTGGGGTTCTTTTTAATGCAAAGTGTCACAAGGCCAGGA   550
SEQID15       1                                                          0

SEQID14     551  ATTCCCATGTGTGCTCAGTTGGCCCACAGCATCATTGTGCCTAGGAAACT   600
SEQID15       1                                                          0

SEQID14     601  GCTTCAATTTATCAAGTCCTCTGGGCTGGGAATCTCACTGAATTCCAAAC   650
SEQID15       1                                                          0

SEQID14     651  GGCGGAAAGAGGAAACTTTCCCAACCCGATGTGGGTGTGACGCGAGCCAG   700
SEQID15       1                                                          0
```

Figure 16B

```
SEQID14    701  GGGCCCCAGGGACACTGTCCCAGAGCACACCGTCCCCCTTTAACAGCAAC     750
SEQID15      1                                                            0

SEQID14    751  TGGAGCTTGGATTCGCTCTTATATTGTACAGTCCTTTCGACCATTGCCCT     800
SEQID15      1                                                            0

SEQID14    801  GGAGCACCCGCACACGCGCACGCATCTCCGGCCGCGCTCACACACACTCA     850
SEQID15      1                                                            0

SEQID14    851  TACACACGCACGCAAACGCGTGGCCGCCGCCAGGTCGGCAACTTTGTCCG     900
SEQID15      1                                                            0

SEQID14    901  GCGCTCCCAGCGGCGCTCGGCTTCCTCCTGTAGTAGTTGAGCGCAGGCCC     950
SEQID15      1                                                            0

SEQID14    951  CGCCTCCCGGCCGTGTTGTCAAAAGGGCCGGGGTCTCGGATTGGTCCAGC    1000
SEQID15      1                                                            0

SEQID14   1001  CGCCGGGACAACACCTGCTCGACTCCTTCATTCAAGTGACACCAGAGCTT    1050
SEQID15      1                                                            0

SEQID14   1051  CCAGGGATATTTGAGGCACCATCCCTGCCATTGCCGGGCACTCGCGGCGC    1100
SEQID15      1                                                            0

SEQID14   1101  TGCTAACGGCCTGGTCACATGCTCTCCGGAGAGCTACGGGAGGGCGCTGG    1150
SEQID15      1                                                            0

SEQID14   1151  GTAACCTCTATCCGAGCCGCGGCCGCGAGGAGGAGGGAAAAGGCGAGCAA    1200
SEQID15      1                                                            0

SEQID14   1201  AAAGGAAGAGTGGGAGGAGGAGGGGAAGCGGCGAAGGAGGAAGAGGAGGA    1250
SEQID15      1                                                            0

SEQID14   1251  GGAGGAAGAGGGGAGCACAAAGGATCCAGGTCTCCCGACGGGAGGTTAAT    1300
                               ||||||||||||| ||||||||||||||||||||
SEQID15      1                  CACAAACGATCCAGGTCTCCCGACGGGAGGTTAAT      35

SEQID14   1301  ACCAAGAACCATGTGTGCCGAGCGGCTGGGCCAGTTCATGACCCTGGCTT    1350
                ||||||||||||||||||||||||||||||||||||||||||||||||||
SEQID15     36  ACCAAGAACCATGTGTGCCGAGCGGCTGGGCCAGTTCATGACCCTGGCTT      85

SEQID14   1351  TGGTGTTGGCCACCTTTGACCCGGCGCGGGGACCGACGCCACCAACCCA    1400
                |||||||||||||||||||||||||||||||| |||||||||||||||||
SEQID15     86  TGGTGTTGGCCACCTTTGACCCGGCGCGGGGACCGACGCCACCAACCCA     135
```

Figure 16C

```
SEQID14   1401  CCCGAGGGTCCCCAAGACAGGAGCTCCCAGCAGAAAGGCCGCCTGTCCCT   1450
                ||||||||||||||||||||||||||||||||||||||||||||||||||
SEQID15    136  CCCGAGGGTCCCCAAGACAGGAGCTCCCAGCAGAAAGGCCGCCTGTCCCT    185

SEQID14   1451  GCAGAATACAGCGGAGATCCAGCACTGTTTGGTCAACGCTGGCGATGTGG   1500
                |||||||| |||||||||||||||||||||||||||||||||||||||||
SEQID15    186  GCAGAATACAGCGGAGATCCAGCACTGTTTGGTCAACGCTGGCGATGTGG    235

SEQID14   1501  GGTGTGGCGTGTTTGAATGTTTCGAGAACAACTCTTGTGAGATTCGGGGC   1550
                ||||||||||||||||||||||||||||||||||||||||||||||||||
SEQID15    236  GGTGTGGCGTGTTTGAATGTTTCGAGAACAACTCTTGTGAGATTCGGGGC    285

SEQID14   1551  TTACATGGGATTTGCATGACTTTTCTGCACAACGCTGGAAAATTTGATGC   1600
                ||||||||||||||||||||||||||||||||||||||||||||||||||
SEQID15    286  TTACATGGGATTTGCATGACTTTTCTGCACAACGCTGGAAAATTTGATGC    335

SEQID14   1601  CCACGGCAAGTCATTCATCAAAGACGCCTTGAAATGTAAGGCCCACGCTC   1650
                |||| |||||||||||||||||||||||||||||||||||||||||||||
SEQID15    336  CCAGGGCAAGTCATTCATCAAAGACGCCTTGAAATGTAAGGCCCACGCTC    385

SEQID14   1651  TGCGGCACAGGTTCGGCTGCATAAGCCGGAAGTGCCCGGCCATCAGGGAA   1700
                ||||||||||||||||||||||||||||||||||||||||||||||||||
SEQID15    386  TGCGGCACAGGTTCGGCTGCATAAGCCGGAAGTGCCCGGCCATCAGGGAA    435

SEQID14   1701  ATGGTGTCCCAGTTGCAGCGGGAATGCTACCTCAAGCACGACCTGTGCGC   1750
                ||||||||||||||||||||||||||||||||||||||||||||||||||
SEQID15    436  ATGGTGTCCCAGTTGCAGCGGGAATGCTACCTCAAGCACGACCTGTGCGC    485

SEQID14   1751  GGCTGCCCAGGAGAACACCCGGGTGATAGTGGAGATGATCCATTTCAAGG   1800
                ||||||||||||||||||||||||||||||||||||||||||||||||||
SEQID15    486  GGCTGCCCAGGAGAACACCCGGGTGATAGTGGAGATGATCCATTTCAAGG    535

SEQID14   1801  ACTTGCTGCTGCACGAACCCTACGTGGACCTCGTGAACTTGCTGCTGACC   1850
                ||||||||||||||||||||||||||||||||||||||||||||||||||
SEQID15    536  ACTTGCTGCTGCACGAACCCTACGTGGACCTCGTGAACTTGCTGCTGACC    585

SEQID14   1851  TGTGGGGAGGAGGTGAAGGAGGCCATCACCCACAGCGTGCAGGTTCAGTG   1900
                ||||||||||||||||||||||||||||||||||||||||||||||||||
SEQID15    586  TGTGGGGAGGAGGTGAAGGAGGCCATCACCCACAGCGTGCAGGTTCAGTG    635

SEQID14   1901  TGAGCAGAACTGGGGAAGCCTGTGCTCCATCTTGAGCTTCTGCACCTCGG   1950
                ||||||||||||||||||||||||||||||||||||||||||||||||||
SEQID15    636  TGAGCAGAACTGGGGAAGCCTGTGCTCCATCTTGAGCTTCTGCACCTCGG    685

SEQID14   1951  CCATCCAGAAGCCTCCCACGGCGCCCCCGAGCGCCAGCCCCAGGTGGAC   2000
                ||||||||||||||||||||||||||||||||||||||||||||||||||
SEQID15    686  CCATCCAGAAGCCTCCCACGGCGCCCCCGAGCGCCAGCCCCAGGTGGAC    735

SEQID14   2001  AGAACCAAGCTCTCCAGGGCCCACCACGGGGAAGCAGGACATCACCTCCC   2050
                ||||||||||||||||||||||||||||
SEQID15    736  AGAACCAAGCTCTCCAGGGCCCACCAC-----------------------    762

SEQID14   2051  AGAGCCCAGCAGTAGGGAGACTGGCCGAGGTGCCAAGGGTGAGCGAGGTA   2100

SEQID15    763  --------------------------------------------------    762
```

Figure 16D

```
SEQID14    2101  GCAAGAGCCACCCAAACGCCCATGCCCGAGGCAGAGTCGGGGGCCTTGGG    2150
SEQID15     763  --------------------------------------------------     762

SEQID14    2151  GCTCAGGGACCTTCCGGAAGCAGCGAGTGGGAAGACGAACAGTCTGAGTA    2200
SEQID15     763  --------------------------------------------------     762

SEQID14    2201  TTCTGATATCCGGAGGTGAAATGAAAGGCCTGGCCACGAAATCTTTCCTC    2250
SEQID15     763  --------------------------------------------------     762

SEQID14    2251  CACGCCGTCCATTTTCTTATCTATGGACATTCCAAAACATTTACCATTAG    2300
SEQID15     763  --------------------------------------------------     762

SEQID14    2301  AGAGGGGGATGTCACACGCAGGATTCTGTGGGACTGTGGACTTCATCG     2350
SEQID15     763  --------------------------------------------------     762

SEQID14    2351  AGGTGTGTGTTCGCGGAACGGACAGGTGAGATGGAGACCCCTGGGGCCGT    2400
SEQID15     763  --------------------------------------------------     762

SEQID14    2401  GGGGTCTCAGGGGTGCCTGGTGAATTCTGCACTTACACGTACTCAAGGGA    2450
SEQID15     763  --------------------------------------------------     762

SEQID14    2451  GCGCGCCCGCGTTATCCTCGTACCTTTGTCTTCTTTCCATCTGTGGAGTC    2500
SEQID15     763  --------------------------------------------------     762

SEQID14    2501  AGTGGGTGTCGGCCGCTCTGTTGTGGGGGAGGTGAACCAGGGAGGGGCAG    2550
SEQID15     763  --------------------------------------------------     762

SEQID14    2551  GGCAAGGCAGGGCCCCCAGAGCTGGGCCACACAGTGGGTGCTGGGCCTCG    2600
SEQID15     763  --------------------------------------------------     762

SEQID14    2601  CCCCGAAGCTTCTGGTGCAGCAGCCTCTGGTGCTGTCTCCGCGGAAGTCA    2650
SEQID15     763  --------------------------------------------------     762

SEQID14    2651  GGGCGGCTGGATTCCAGGACAGGAGTGAATGTAAAAATAAATATCGCTTA    2700
SEQID15     763  --------------------------------------------------     762

SEQID14    2701  GAATGCAGGAGAAGGGTGGAGAGGAGGCAGGGGCCGAGGGGGTGCTTGGT    2750
                                                      ||||||||||||
SEQID15     763  -------------------------------------GGGGTGCTTGGT     774

SEQID14    2751  GCCAAACTGAAATTCACTTTCTTCTGTGGGGCCTTGCGGTTCAGAGCTCT    2800
                 ||||||||||||||| ||||||||||||||||||||||||||||||||||
SEQID15     775  GCCAAACTGAAATTCAGTTTCTTGTGTGGGGCCTTGCGGTTCAGAGCTCT     824
```

Figure 16E

```
SEQID14    2801  TGGCGAGGGTGGAGGGAGGAGTGTCATTTCTATGTGTAATTTCTGAGCCA    2850
                 ||||||||||||||||||||||||||||||||||||||||||||||||||
SEQID15     825  TGGCGAGGGTGGAGGGAGGAGTGTCATTTCTATGTGTAATTTCTGAGCCA     874

SEQID14    2851  TTGTACTGTCTGGGCTGGGGGGACACTGTCCAAGGGAGTGGCCCCTATG    2900
                 |||||||||||||||||||||||||||||||||||||||||||||||||
SEQID15     875  TTGTACTGTCTGGGCTGGGGGGACACTGTCCAAGGGAGTGGCCCCTATG     924

SEQID14    2901  AGTTTATATTTTAACCACTGCTTCAAATCTCGATTTCACTTTTTTATTT    2950
                 |||||||||||||||||||||||||||||||||||||||||||||||||
SEQID15     925  AGTTTATATTTTAACCACTGCTTCAAATCTCGATTTCACTTTTTTATTT     974

SEQID14    2951  ATCCAGTTATATCTACATATCTGTCATCTAAATAAATGGCTTTCAAACAA    3000
                 ||||||||||||||||||||||||||||||||||||||||||||||||||
SEQID15     975  ATCCAGTTATATCTACATATCTGTCATCTAAATAAATGGCTTTCAAACAA    1024

SEQID14    3001  AGCAACTGGGTCATTAAAACCAGCTCAAAGGGGGTTTAAAAAAAAAAAAC    3050
                 ||||||||||||||||||||||||||||||||||||||||||||||||
SEQID15    1025  AGCAACTGGGTCATTAAAACCAGCTCAAAGGGGGTTTAAAAAAAAAAAA    1073

SEQID14    3051  CAGCCCATCCTTTGAGGCTGATTTTTCTTTTTTTTAAGTTCTATTTTAAA    3100
SEQID15    1074                                                         1073

SEQID14    3101  AGCTATCAAACAGCGACATAGCCATACATCTGACTGCCTGACATGGACTC    3150
SEQID15    1074                                                         1073

SEQID14    3151  CTGCCCACTTGGGGGAAACCTTATACCCAGAGGAAAATACACACCTGGGG    3200
SEQID15    1074                                                         1073

SEQID14    3201  AGTACATTTGACAAATTTCCCTTAGGATTTCGTTATCTCACCTTGACCCT    3250
SEQID15    1074                                                         1073

SEQID14    3251  CAGCCAAGATTGGTAAAGCTGCGTCCTGGCGATTCCAGGAGACCCAGCTG    3300
SEQID15    1074                                                         1073

SEQID14    3301  GAAACCTGGCTTCTCCATGTGAGGGGATGGGAAAGGAAAGAAGAGAATGA    3350
SEQID15    1074                                                         1073

SEQID14    3351  AGACTACTTAGTAATTCCCATCAGGAAATGCTGACCTTTTACATAAAATC    3400
SEQID15    1074                                                         1073

SEQID14    3401  AAGGAGACTGCTGAAAATCTCTAAGGGACAGGATTTTCCAGATCCTAATT    3450
SEQID15    1074                                                         1073

SEQID14    3451  GGAAATTTAGCAATAAGGAGAGGAGTCCAACGGGACAAATAAAGGCAGAG    3500
SEQID15    1074                                                         1073
```

Figure 16F

```
SEQID14   3501 AGAAGAGACAGAACTAAAAATACGAGGAAAGGAGAGTGAGGATTTTCATT   3550
SEQID15   1074                                                         1073

SEQID14   3551 AAAAGTCTCAGCAGTGGGTTTCTTGGGTTATTTAAAACATCACCTAAATA   3600
SEQID15   1074                                                         1073

SEQID14   3601 GGCCTTTTCTTCCTAATTGGCCATCAAATTAAAGCCTATCCTTTCTCAAG   3650
SEQID15   1074                                                         1073

SEQID14   3651 CAGGAGCTGGTATTGTAGGGAGTGGCCGGGTATTCTGGGCTGGGCTCTTC   3700
SEQID15   1074                                                         1073

SEQID14   3701 TGGAGTAGGGGGTCAGCAAACATTGTCTGCAAAGGGCCAGATACTGAATC   3750
SEQID15   1074                                                         1073

SEQID14   3751 CAGTACTTTCAGTTTGGCGAGCCGTGAGGTCTCTGTCGAAACTACTCAAC   3800
SEQID15   1074                                                         1073

SEQID14   3801 TCTGCCGTCCTAGCACAAAAGCAGCCATAGACAACACACAAACGAGAGGG   3850
SEQID15   1074                                                         1073

SEQID14   3851 CTTGGCTCCCTTCCAGGAAGATTTATTTAACAGGCTCCCAGCTGAATTTC   3900
SEQID15   1074                                                         1073

SEQID14   3901 ACTCACAGGACACAGTTTACTGATCTCTGTTCTAGTGAGTGGGTCAAAAA   3950
SEQID15   1074                                                         1073

SEQID14   3951 GCATATGCATCCTTATCCGTCAACTCATCAGCTCTTCCTCAAGGCAACCT   4000
SEQID15   1074                                                         1073

SEQID14   4001 GAGGCCAGACACCAAGAAACCAAGCGTATCTGCTCTAAAATGACTTGTTC   4050
SEQID15   1074                                                         1073

SEQID14   4051 CTGGGGAATGCCTTCAACCAAAACACAGCTAGTATTTCTATCCCCCAAAT   4100
SEQID15   1074                                                         1073

SEQID14   4101 CCAATCCCAGTCTTTCATGATCCATGCCGGCGGTTGGGTGGGGAGGGGAA   4150
SEQID15   1074                                                         1073

SEQID14   4151 TCATTGGTTGGGGGAAGGGAGGAAACCCCACCTCCAGCCCCCGCCACCGG   4200
SEQID15   1074                                                         1073
```

Figure 16G

| | | | |
|---|---|---|---|
| SEQID14 | 4201 | GCTCCCTGGGCACCCAGCAAGATCTGGGGCTGCAGAGAACAGAAGAGCTG | 4250 |
| SEQID15 | 1074 | | 1073 |
| SEQID14 | 4251 | GTGCACTTAATCCAGCTCTGCCCTTGGGGGAGGAGGACCTGTGTGTCAG | 4300 |
| SEQID15 | 1074 | | 1073 |
| SEQID14 | 4301 | GCTCTGCCATGGGAACGAGTGTAAACCGTGGCTGTCTCCTGCAGTGAGCC | 4350 |
| SEQID15 | 1074 | | 1073 |
| SEQID14 | 4351 | ACCGCGGCAGGCACGTTGACTGTTTTACTGACATCACTCAAAAGCTAAAG | 4400 |
| SEQID15 | 1074 | | 1073 |
| SEQID14 | 4401 | CAATAACATTCTCCTGCGTTGCTGAGTCAGCTGTTCATTTGTCCGCCAGC | 4450 |
| SEQID15 | 1074 | | 1073 |
| SEQID14 | 4451 | TCCTGGACTGGATGTGTGAAAGGCATCACATTTCCATTTTCCTCCGTGTA | 4500 |
| SEQID15 | 1074 | | 1073 |
| SEQID14 | 4501 | AATGTTTTATGTGTTCGCCTACTGATCCCATTCGTTGCTTCTATTGTAAA | 4550 |
| SEQID15 | 1074 | | 1073 |
| SEQID14 | 4551 | TATTTGTCATTTGTATTTATTATCTCTGTGTTTTCCCCCTAAGGCATAAA | 4600 |
| SEQID15 | 1074 | | 1073 |
| SEQID14 | 4601 | ATGGTTTACTGTGTTCATTTGAACCCATTTACTGATCTCTGTTGTATATT | 4650 |
| SEQID15 | 1074 | | 1073 |
| SEQID14 | 4651 | TTTCATGCCACTGCTTTGTTTTCTCCTCAGAAGTCGGGTAGATAGCATTT | 4700 |
| SEQID15 | 1074 | | 1073 |
| SEQID14 | 4701 | CTATCCCATCCCTCACGTTATTGGAAGCATGCAACAGTATTTATTGCTCA | 4750 |
| SEQID15 | 1074 | | 1073 |
| SEQID14 | 4751 | GGGTCTTCTGCTTAAAACTGAGGAAGGTCCACATTCCTGCAAGCATTGAT | 4800 |
| SEQID15 | 1074 | | 1073 |
| SEQID14 | 4801 | TGAGACATTTGCACAATCTAAAATCTAAGCAAAGTAGTCATTAAAAATAC | 4850 |
| SEQID15 | 1074 | | 1073 |
| SEQID14 | 4851 | ACCCTCTACTTGGGCTTTATACTGCATACAAATTTACTCATGAGCCTTCC | 4900 |
| SEQID15 | 1074 | | 1073 |

Figure 16H

```
SEQID14    4901  TTTGAGGAACGATGTGGATCTCCAAATAAAGATTTAGTGTTTATTTTGAG  4950
SEQID15    1074                                                        1073

SEQID14    4951  CTCTGCATCTTAACAAGATGATCTGAACACCTCTCCTTTGTATCAATAAA  5000
SEQID15    1074                                                        1073

SEQID14    5001  TAGCCCTGTTATTCTGAAGTGAGAGGACCAAGTATAGTAAAATGCTGACA  5050
SEQID15    1074                                                        1073

SEQID14    5051  TCTAAAACTAAATAAATAGAAAACACCAGGCCAGAACTATAGTCATACTC  5100
SEQID15    1074                                                        1073

SEQID14    5101  ACACAAAGGGAGAAATTTAAACTCGAACCAAGCAAAAGGCTTCACGGAAA  5150
SEQID15    1074                                                        1073

SEQID14    5151  TACCATCGAAAAACAATGCTTCCAGTGGCCACTTCCTAAGGAGGAACAAC  5200
SEQID15    1074                                                        1073

SEQID14    5201  CCCGTCTGATCTCAGAATTGGCACCACGTGAGCTTGCTAAGTGATAATAT  5250
SEQID15    1074                                                        1073

SEQID14    5251  CTGTTTCTACTACGGATTTAGGCAACAGGACCTGTACATTGTCACATTGC  5300
SEQID15    1074                                                        1073

SEQID14    5301  ATTATTTTCTTCAAGCGTTAATAAAAGTTTTAAATAAATGGCAAAAAAA   5350
SEQID15    1074                                                        1073

SEQID14    5351  AAAAAAAAAA       5361
SEQID15    1074                   1073
```

Figure 17A

```
SEQID16        1 CCCCGCAGGCTGAGGGCAGGTGGGAAGCAAACCCGGACGCATCGCAGCAG    50
                 |||||||||||||||||||||||||||||||||||||||||||||||||
SEQID17        1 CCCCGCAGGCTGAGGGCAGGTGGGAAGCAAACCCGGACGCATCGCAGCAG    50

SEQID16       51 CAGCAGCAGCAGCAGAAGCAGCAGCAGCAGCCTCCGCAGTCCCTCCAGAG   100
                 |||||||||||||||||||||||||||||||||||||||||||||||||
SEQID17       51 CAGCAGCAGCAGCAGAAGCAGCAGCAGCAGCCTCCGCAGTCCCTCCAGAG   100

SEQID16      101 ACATGGATCCCCAGACAGCACCTTCCCGGGCGCTCCTGCTCCTGCTCTTC   150
                 |||||||||||||||||||||||||||||||||||||||||||||||||
SEQID17      101 ACATGGATCCCCAGACAGCACCTTCCCGGGCGCTCCTGCTCCTGCTCTTC   150

SEQID16      151 TTGCATCTGGCTTTCCTGGGAGGTCGTTCCCACCCGCTGGGCAGCCCCGG   200
                 |||||||||||||||||||||||||||||||||||||||||||||||||
SEQID17      151 TTGCATCTGGCTTTCCTGGGAGGTCGTTCCCACCCGCTGGGCAGCCCCGG   200

SEQID16      201 TTCAGCCTCGGACTTGGAAACGTCCGGGTTACAGGAGCAGCGCAACCATT   250
                 |||||||||||||||||||||||||||||||||||||||||||||||||
SEQID17      201 TTCAGCCTCGGACTTGGAAACGTCCGGGTTACAGGAGCAGCGCAACCATT   250

SEQID16      251 TGCAGGGCAAACTGTCGGAGCTGCAGGTGGAGCAGACATCCCTGGAGCCC   300
                 |||||||||||||||||||||||||||||||||||||||||||||||||
SEQID17      251 TGCAGGGCAAACTGTCGGAGCTGCAGGTGGAGCAGACATCCCTGGAGCCC   300

SEQID16      301 CTCCAGGAGAGCCCCCGTCCCACAGGTGTCTGGAAGTCCCGGGAGGTAGC   350
                 |||||||||||||||||||||||||||||||||||||||||||||||||
SEQID17      301 CTCCAGGAGAGCCCCCGTCCCACAGGTGTCTGGAAGTCCCGGGAGGTAGC   350

SEQID16      351 CACCGAGGGCATCCGTGGGCACCGCAAAATGGTCCTCTACACCCTGCGGG   400
                 |||||||||||||||||||||||||||||||||||||||||||||||||
SEQID17      351 CACCGAGGGCATCCGTGGGCACCGCAAAATGGTCCTCTACACCCTGCGGG   400

SEQID16      401 CACCACGAAGCCCCAAGATGGTGCAAGGGTCTGGCTGCTTTGGGAGGAAG   450
                 |||||||||||||||||||||||||||||||||||||||||||||||||
SEQID17      401 CACCACGAAGCCCCAAGATGGTGCAAGGGTCTGGCTGCTTTGGGAGGAAG   450

SEQID16      451 ATGGACCGGATCAGCTCCTCCAGTGGCCTGGGCTGCAAAGTGCTGAGGCG   500
                 ||||||||||||||||||||||||||||||||||||||||....|....|.
SEQID17      451 ATGGACCGGATCAGCTCCTCCAGTGGCCTGGGCTGCAAAGGTAAGCACCC   500

SEQID16      501 GCATTAA-------------------------GAGGAAGTCCTGGCTGC   524
                 .|....|                         |.|..|..|.........
SEQID17      501 CCTGCCACCCCGGCCGCCTTCCCCCATTCCAGTGTGTGACACTGTTAGAG   550

SEQID16      525 AGACACCTGCTTCTGATTCCACAAGGGGCTTTTTCCTCAACCCTGTGGCC   574
                 ..|....|..|.||.|..|.|..||..|......||.........||.|
SEQID17      551 TCACTTTGGGGTTTGTTGTCTCTGGGAACCACACTCTTTGAGAAAAGGTC   600

SEQID16      575 GCCTTTGAAGTGACTCATTTTTTTAATGTATTTATGTATTTATTTGATTG   624
                 .|||....|..|..||.|.|..||||.....||..|......|...|...
SEQID17      601 ACCTGGACATCGCTTCCTCTTGTTAACAGCCTTCAGGGCCAAGGGGTGCC   650

SEQID16      625 TTTTATATAAGATGGTTTCTTACCTTTGAGCACAAAATTTCCACGGTGAA   674
                 |||.....|..|.....|....||||...|...|....|.||.......|.
SEQID17      651 TTTGTCGAATTAGTAAATGTGGGCTTATTTCATTACCATGCCCACAATAC   700
```

Figure 17B

```
SEQID16      675 ATAAAGTCAACATTATAAGCTTTAAAAAAAAAAA                      708
                 .|.....|.:|.|..||....|||..|||.....
SEQID17      701 CTTCTCCCCACCTCCTACTTCTTATCAAAGGGGCAGAATCTCCTTTGGGG     750

SEQID16      709                                                         708

SEQID17      751 GTCTGTTTATCATTTGGCAGCCCCCCAGTGGTGCAGAAAGAGAACCAAAC     800

SEQID16      709                                                         708

SEQID17      801 ATTTCCTCCTGGTTTCCTCTAAACTGTCTATAGTCTCAAAGGCAGAGAGC     850

SEQID16      709                                                         708

SEQID17      851 AGGATCACCAGAGCAATGATAATCCCCAATTTACAGATGAGGAAACTGAG     900

SEQID16      709              708

SEQID17      901 GCTCA        905
```

Figure 18A

```
SEQID18     1 AGTCCTGCGTCCGGGCCCCGAGGCGCAG-CAGGGCACCAGGTGGAGCACC    49
              |||||||||||||||||||||||||||| ||| |||||||||||||||||
SEQID19     1 AGTCCTGCGTCCGGGCCCCGAGGCACAGCCAGGGCACCAGGTGGAGCACC    50

SEQID18    50 ACCTACGCGTGGCGCAGCGCAGCGTCCCTAGCACCGAGCCTCCCGCAGCC    99
              ||||||||||:|||||||||||||||||||||||||||||||||||||||
SEQID19    51 AGCTACGCGTGGCGCAGCGCAGCGTCCCTAGCACCGAGCCTCCCGCAGCC   100

SEQID18   100 GCCGAGATGCTGCGAACAGAGAGCTGCCGCCCCAGGTCGCCCGCCGGACA   149
              |||||||||||||||||||||||||||||||||||| |||||||||||||
SEQID19   101 GCCGAGATGCTGCGAACAGAGAGCTGCCGCCCCAGGTCGCCCGCCGGACA   150

SEQID18   150 GGTGGCCGCGGCGTCCCCGCTCCTGCTGCTGCTGCTGCTCGCCTGGT    199
              |||||||||||||||||||!|||||||||:|||||||||:|||||||||
SEQID19   151 GGTGGCCGCGGCGTCCCCGCTCCTGCTGCTGCTGCTGCTCGCCTGGT    200

SEQID18   200 GCGCGGGCGCCTGCCGAGGTGCTCCAATATTACCTCAAGGATTACAGCCT   249
              ||:|||||||||||||||||||||||||||||||||||||||||||||||
SEQID19   201 GCGCGGGCGCCTGCCGAGGTGCTCCAATATTACCTCAAGGATTACAGCCT   250

SEQID18   250 GAACAACAGCTACAGTTGTGGAATGAGATAGATGATACTTGTTCGTCTTT   299
              ||||||||||||||||||||||||||||||||||||||||||||||||||
SEQID19   251 GAACAACAGCTACAGTTGTGGAATGAGATAGATGATACTTGTTCGTCTTT   300

SEQID18   300 TCTGTCCATTGATTCTCAGCCTCAGGCATCCAACGCACTGGAGGAGCTTT   349
              ||||||||||||||||||||||||||||||||||||||||||||||||||
SEQID19   301 TCTGTCCATTGATTCTCAGCCTCAGGCATCCAACGCACTGGAGGAGCTTT   350

SEQID18   350 GCTTTATGATTATGGGAATGCTACCAAAGCCTCAGGAACAAGATGAAAAA   399
              !|||||||||||||||||||||||||||:|||||||||||||||||||||
SEQID19   351 GCTTTATGATTATGGGAATGCTACCAAAGCCTCAGGAACAAGATGAAAAA   400

SEQID18   400 GATAATACTAAAAGGTTCTTATTTCATTATTCGAAGACACAGAAGTTGGG   449
              ||||||||||||||||||||||||||||||||||||||||||||||||||
SEQID19   401 GATAATACTAAAAGGTTCTTATTTCATTATTCGAAGACACAGAACTTGGG   450

SEQID18   450 CAAGTCAAATGTTGTGTCGTCAGTTGTGCATCCGTTGCTGCAGCTCGTTC   499
              ||||||||||||||| |||
SEQID19   451 CAAGTCAAATGTTGTG----------------------------------   466

SEQID18   500 CTCACCTGCATCACAGAAGAATGAAGAGATTCAGAGTGGACGAAGAATTC   549
                                                       ||||!||||
SEQID19   467 ------------------------------------   ---GAAGAATTC   475

SEQID18   550 CAAAGTCCCTTTGCAAGTCAAAGTCGAGGATATTTTTTATTCAGGCCACG   599
              ||||||||||||||||||||||||||:|||||||||||||||||||||||
SEQID19   476 CAAAGTCCCTTTGCAAGTCAAAGTCGAGGATATTTTTTATTCAGGCCACG   525

SEQID18   600 GAATGGAAGAAGGTCAGCAGGGTTCATTTAAAATGGATGCCAGCTAATTT   649
              ||||||||||||:|||||||||||||||||||||||||||||||||||||
SEQID19   526 GAATGGAAGAAGGTCAGCAGGGTTCATTTAAAATGGATGCCAGCTAATTT   575

SEQID18   650 TCCACAGAGCAATGCTATGGAATACAAAATGTACTGACATTTTGTTTTCT   699
              |||||||||||||||||||||||||||||||||||||||||||||:||||
SEQID19   576 TCCACAGAGCAATGCTATGGAATACAAAATGTACTGACATTTTGTTTTCT   625
```

Figure 18B

```
SEQID18    700  TCTGAAAAAAATCCTTGCTAAATGTACTCTGTTGAAAATCCCTGTGTTGT    749
                |||||||||||||||||||||||||||||||||||||||||||||||||
SEQID19    626  TCTGAAAAAAATCCTTGCTAAATGTACTCTGTTGAAAATCCCTGTGTTGT    675

SEQID18    750  CAATGTTCTCAGTTGTAACAATGTTGTAAATGTTCAATTTGTTGAAAATT    799
                |||||||||||||||||||||||||||||||||||||||||||||||||
SEQID19    676  CAATGTTCTCAGTTGTAACAATGTTGTAAATGTTCAATTTGTTGAAAATT    725

SEQID18    800  AAAAAATCTAAAAATAAA         817
                ||||||||||||||||
SEQID19    726  AAAAAATCTAAAAATA           741
```

COMPOSITIONS, REAGENTS AND KITS FOR AND METHODS OF DIAGNOSING, MONITORING AND TREATING HORMONAL IMBALANCE

CROSS-REFERENCE TO RELATED APPLICATION

This application claims priority from Provisional U.S. Patent Application Ser. No. 60/733,090, filed Nov. 3, 2005, which is incorporated herein by reference.

FIELD OF THE INVENTION

The present invention relates to hormonal imbalance markers; to reagents which can detect hormonal imbalance marker transcripts and translation products; to kits and methods for detecting hormonal imbalance marker transcripts and translation products; to methods and kits for screening and diagnosing hormonal imbalance in individuals and monitoring response to treatment, disease progression and disease recurrence in patients diagnosed with hormonal imbalance; to compounds which specifically bind to translation products of the hormonal imbalance marker transcripts; to treating the hormonal imbalance using one or a composition of several of the hormonal imbalance markers or their translation products as therapeutic agents; to compositions for and methods of treating the hormonal imbalance.

BACKGROUND OF THE INVENTION

Every cell is capable of producing a vast number of regulatory molecules (hormones). The classical endocrine glands and their hormone products are specialized to serve regulation on the overall organism level, but can in many instances be used in other ways or only on the tissue level. The rate of production of a given hormone is most commonly regulated by a homeostatic control system, generally by negative feedback. Homeostatic regulation of hormones depends, apart from production, on the metabolism and excretion of hormones. Hormone secretion can be stimulated and inhibited by: Other hormones (stimulating or releasing-hormones), Plasma concentrations of ions or nutrients, as well as binding proteins, Neurons and mental activity.

Peptide hormones are a class of peptides that are secreted into the blood stream and have endocrine functions in living animals. Peptide hormone precursors (pre-prohormones) are processed in several stages, typically in the endoplasmic reticulum, including removal of the N-terminal signal sequence and sometimes glycosylation, resulting in prohormones.

These prohormones often contain superfluous amino acid residues that were needed to direct folding of the hormone molecule into its active configuration but have no function once the hormone folds. Specific endopeptidases in the cell cleave the prohormone just before it is released into the blood stream, generating the mature hormone form of the molecule. Mature peptide hormones then diffuse through the blood to all of the cells of the body, where they interact with specific receptors on the surface of their target cells.

Peptide hormones are key players in most of the major life threatening diseases like Diabetes, Obesity, Cancer, and cardiovascular disease.

There remains a need for hormonal imbalance specific markers. There remains a need for reagents and kits which can be used to detect the presence of hormonal imbalance markers in samples from patients. There remains a need for reagents and kits which can be used to detect the future propensity of developing hormonal imbalance in samples from patients. There remains a need for methods of screening and diagnosing individuals who have hormonal imbalance and methods of monitoring response to treatment, disease progression and disease recurrence in patients diagnosed with hormonal imbalance.

There remains a need for reagents, kits and methods for determining the type of hormonal imbalance that an individual has. There remains a need for compositions which can specifically target hormonal imbalance related cells. There remains a need for improved methods of treating individuals who are suspected of suffering from hormonal imbalance.

GLOSSARY

In the following description and claims, use will be made, at times, with a variety of terms, and the meaning of such terms as they should be construed in accordance with the invention is as follows:

"Hormonal Imbalance nucleic acid sequences"—the sequence shown in any one of SEQ ID NO:1 to SEQ ID NO:2 and of SEQ ID NO:20 to SEQ ID NO:21, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Glucagon, depicted in NCBI Gene database as GeneID: 2641 under Accession Number NM_002054 which is the sequence coding for the human 21 kDa preproprotein of 180 amino acids that is cleaved into five distinct mature peptides, Glucagon, GLP-1, GLP-2, Oxyntomodulin, and Glicentin. One of these, Glucagon, plays a key role in glucose metabolism and homeostasis, regulating blood glucose by increasing gluconeogenesis and decreasing glycolysis. Glucagon is a counterregulatory hormone of insulin, raising plasma glucose levels in response to insulin-induced hypoglycemia, and playing an important role in initiating and maintaining hyperglycemic conditions in diabetes. GLP-1 is a potent stimulator of glucose-dependent insulin release, playing important roles on gastric motility and the suppression of plasma glucagon levels. GLP-1 may be involved in the suppression of satiety and stimulation of glucose disposal in peripheral tissues, independent of the actions of insulin, and it has growth-promoting activities on intestinal epithelium. GLP-1 may also regulate the hypothalamic pituitary axis (HPA) via effects on LH, TSH, CRH, oxytocin, and vasopressin secretion. GLP-1 increases islet mass through stimulation of islet neogenesis and pancreatic beta cell proliferation, and it inhibits beta cell apoptosis. GLP-2 stimulates intestinal growth and up-regulates villus height in the small intestine, concomitant with increased crypt cell proliferation and decreased enterocyte apoptosis. The gastrointestinal tract, from the stomach to the colon is the principal target for GLP-2 action. GLP-2 plays a key role in nutrient homeostasis, enhancing nutrient assimilation through enhanced gastrointestinal function, as well as increasing nutrient disposal. GLP-2 stimulates intestinal glucose transport and decreases mucosal permeability. Oxyntomodulin significantly reduces food intake, and it inhibits gastric emptying in humans. Oxyntomodulin also suppresses gastric emptying, which may lead to increased gastric distension, which in turn may contribute to satiety by causing a sensation of fullness. Finally, the fifth peptide Glicentin may modulate gastric acid secretion and the gastro-pyloro-duodenal activity. Glicentin may also play an important role in intestinal mucosal growth in the early period of life. It should be emphasized that the novel variants of the present invention are naturally occurring sequences resulting from alternative splicing of Glucagon and not merely truncated, mutated or fragmented forms of the gene.

the sequence shown in any one of SEQ ID NO:3 to SEQ ID NO:5 and of SEQ ID NO:22 to SEQ ID NO:24, sequences having at least 90%, at least 91%, at least 92%, at least 93%, at least 94%, at least 95%, at least 96%, at least 97%, at least 98%, or at least 99% identity (see below) to said sequences, and fragments (see below, Table 2) of the above sequences of least 15 b.p. long. These sequences are sequences coding for naturally occurring, alternative splice variants of the native and known Neurotensin, depicted in NCBI Gene database as GeneID: 4922 under Accession Number NM_006183, which is the sequence coding for the human 20 kDa, a 170 amino acid common precursor for two peptides, neuromedin N and neurotensin. Neurotensin is a secreted tridecapeptide, which is widely distributed throughout the central nervous system, and may function as a neurotransmitter or a neuromodulator. It may be involved in dopamine-associated pathophysiological events, in the maintenance of gut structure and function, and in the regulation of fat metabolism. Tissue-specific processing may lead to the formation in some tissues of larger forms of neuromedin N and neurotensin. The large forms may represent more stable peptides that are also biologically active. It should be emphasized that the novel variants of the present invention are naturally occurring sequences resulting from alternative splicing of Neurotensin and not merely truncated, mutated or fragmented forms of the gene.

the sequence shown in any one of SEQ ID NO:6 to SEQ ID NO:7 and of SEQ ID NO:25 to SEQ ID NO:26, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known pancreatic polypeptide (PPY), depicted in NCBI Gene database as GeneID: 5539 under Accession Number NM_002722, which is the sequence coding for the human 10 kDa protein precursor of 95 amino acids. Pancreatic hormone is synthesized in pancreatic islets of Langerhans and acts as a regulator of pancreatic and gastrointestinal functions. This hormone of 36 amino acids is involved in the regulation of exocrine pancreatic secretion and biliary tract motility. PPY is involved in regulation of food intake. It should be emphasized that the novel variants of the present invention are naturally occurring sequences resulting from alternative splicing of PPY and not merely truncated, mutated or fragmented forms of the gene.

the sequence shown in any one of SEQ ID NO:8 to SEQ ID NO:9 and of SEQ ID NO:27 to SEQ ID NO:28, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known CART (cocaine- and amphetamine-regulated transcript), depicted in NCBI Gene database as GeneID: 9607 under Accession Number NM_004291, which is the sequence coding for the human 13 kDa preprotein of 116 amino acids. CART is a satiety factor closely associated with the actions of leptin and neuropeptide Y; this anorectic peptide inhibits both normal and starvation-induced feeding and completely blocks the feeding response induced by neuropeptide Y and regulated by leptin in the hypothalamus. It promotes neuronal development and survival in vitro. It should be emphasized that the novel variants of the present invention are naturally occurring sequences resulting from alternative splicing of CART and not merely truncated, mutated or fragmented forms of the gene.

the sequence shown in any one of SEQ ID NO:10 to SEQ ID NO:11 and of SEQ ID NO:29 to SEQ ID NO:30, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Urocortin (UCN), depicted in NCBI Gene database as GeneID: 7349 under Accession Number NM_003353, which is the sequence coding for the human 13.5 kDa preprotein of 124 amino acids. Urocortin acts in vitro to stimulate the secretion of adrenocorticotropic hormone (ACTH) and it may be responsible for the effects of stress on appetite. Urocortin binds with high affinity to CRF Receptor types 1,2-alpha, and 2-beta. It should be emphasized that the novel variants of the present invention are naturally occurring sequences resulting from alternative splicing of Urocortin and not merely truncated, mutated or fragmented forms of the gene.

the sequence shown in any one of SEQ ID NO:12 to SEQ ID NO:13 and of SEQ ID NO:31 to SEQ ID NO:32, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Proenkephalin (PENK), depicted in NCBI Gene database as GeneID: 5179 under Accession Number NM_006211, which is the sequence coding for the human 31 kDa preprotein of 267 amino acids. Proenkephalin compete with and mimic the effects of opiate drugs. It plays a role in a number of physiologic functions, including pain perception and responses to stress. It should be emphasized that the novel variants of the present invention are naturally occurring sequences resulting from alternative splicing of Proenkephalin and not merely truncated, mutated or fragmented forms of the gene.

the sequence shown in any one of SEQ ID NO:14 to SEQ ID NO:15 and of SEQ ID NO:33 to SEQ ID NO:34, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Stanniocalcin 2 (STC2), depicted in NCBI Gene database as GeneID: 8614 under Accession Number NM_003714, which is the sequence coding for the human 33 kDa preprotein of 302 amino acids. Stanniocalcin 2 has an anti-hypocalcemic action on calcium and phosphate homeostasis. It should be emphasized that the novel variants of the present invention are naturally occurring sequences resulting from alternative splicing of Stanniocalcin 2 and not merely truncated, mutated or fragmented forms of the gene.

the sequence shown in any one of SEQ ID NO:16 to SEQ ID NO:17 and of SEQ ID NO:35 to SEQ ID NO:36, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Natriuretic peptide precursor B (NPPB), depicted in NCBI Gene database as GeneID: 4879 under Accession Number NM_002521, which is the sequence coding for the human 15 kDa preprotein of 134 amino acids. NPPB acts as a cardiac hormone with a variety of biological actions including natriuresis, diuresis, vasorelaxation, and inhibition of renin and aldosterone secretion. It is thought to play a key role in cardiovascular homeostasis, and it helps restore the body's salt and water balance. NPPB also improves heart function. It should be emphasized that the novel variants of the present invention are naturally occurring sequences resulting from alternative splicing of NPPB and not merely truncated, mutated or fragmented forms of the gene.

the sequence shown in any one of SEQ ID NO:18 to SEQ ID NO:19 and of SEQ ID NO:37 to SEQ ID NO:38, sequences having at least 90%, at least 91%, at least 92%, at least 93%, at least 94%, at least 95%, at least 96%, at least 97%, at least 98%, or at least 99% identity (see below) to said sequences, and fragments (see below) of the above sequences of least 15 b.p. long. These sequences are sequences coding for naturally occurring, alternative splice variants of the native and known Neuromedin U (NMU), depicted in NCBI Gene database as GeneID: 10874 under Accession Number NM_006681, which is the sequence coding for the human 20 kDa preprotein of 174 amino acids. NMU stimulates muscle contractions of specific regions of the gastrointestinal tract. In humans, NMU stimulates contractions of the ileum and urinary bladder. It should be emphasized that the novel variants of the present invention are naturally occurring sequences resulting from alternative splicing of NMU and not merely truncated, mutated or fragmented forms of the gene.

The description of the hormonal imbalance related gene variants and their difference from the original sequence are summarized in Table 1 as follows:

TABLE 1

| SEQ ID NO: | Hormonal Imbalance related genes | GenBank Human GeneID | Gene Symbol | Variation description |
|---|---|---|---|---|
| 1 | Glucagon - WT (Variant 1) | 2641 | GCG | Nucleotide sequence of the human wild type protein |
| 2 | Glucagon (Variant 2) | | | Nucleotide sequence of variant 2 |
| 3 | Neurotensin - WT (Variant 1) | 4922 | NTS | Nucleotide sequence of the human wild type protein |
| 4 | Neurotensin (Variant 2) | | | Nucleotide sequence of variant 2 |
| 5 | Neurotensin (Variant 3) | | | Nucleotide sequence of variant 3 |
| 6 | Pancreatic Polypeptide - WT (Variant 1) | 5539 | PPY | Nucleotide sequence of the human wild type protein |
| 7 | Pancreatic Polypeptide (Variant 2) | | | Nucleotide sequence of variant 2 |
| 8 | CART (cocaine and amphetamine-regulated transcript) - WT (Variant 1) | 9607 | CART | Nucleotide sequence of the human wild type protein |
| 9 | CART (cocaine and amphetamine-regulated transcript) (Variant 2) | | | Nucleotide sequence of variant 2 |
| 10 | Urocortin - WT (variant 1) | 7349 | UCN | Nucleotide sequence of the human wild type protein |
| 11 | Urocortin (Variant 2) | | | Nucleotide sequence of variant 2 |
| 12 | Proenkephalin - WT (Variant 1) | 5179 | PENK | Nucleotide sequence of the wild type human protein |
| 13 | Proenkephalin (Variant 2) | | | Nucleotide sequence of variant 2 |
| 14 | Stanniocalcin 2 - WT (Variant 1) | 8614 | STC2 | Nucleotide sequence of the wild type human protein |
| 15 | Stanniocalcin 2 (Variant 2) | | | Nucleotide sequence of variant 2 |
| 16 | Natriuretic peptide precursor B - WT (Variant 1) | 4879 | NPPB | Nucleotide sequence of the wild type human protein |
| 17 | Natriuretic peptide precursor B (Variant 2) | | | Nucleotide sequence of (variant 2) |
| 18 | Neuromedin U - WT (Variant 1) | 10874 | NMU | Nucleotide sequence of the wild type human protein |
| 19 | Neuromedin U (Variant 2) | | | Nucleotide sequence of variant 2 |
| 20 | Glucagon - WT (Variant 1) | 2641 | GCG | Wild type human protein sequence |
| 21 | Glucagon (Variant 2) | | | An alternative exon alters the protein from position 105 in the wild type protein creating a modified GLP-1 peptide and no GLP-2 peptide |
| 22 | Neurotensin- WT (Variant 1) | 4922 | NTS | Wild type human protein sequence |
| 23 | Neurotensin (Variant 2) | | | An alternative c-terminal exon alters the Neurotensin protein from position 151 |
| 24 | Neurotensin (Variant 3) | | | Omission of an alternative exon alter the Neurotensin protein by omitting amino acids 46-120 creating a shorter Neurotensin protein |

TABLE 1-continued

| SEQ ID NO: | Hormonal Imbalance related genes | GenBank Human GeneID | Gene Symbol | Variation description |
|---|---|---|---|---|
| 25 | Pancreatic Polypeptide - WT (Variant 1) | 5539 | PPY | Wild type human protein sequence |
| 26 | Pancreatic Polypeptide (Variant 2) | | | An inclusion of an alternative exon adds 9aa after position 63 in the wild type protein thus creating a longer pancreatic hormone |
| 27 | CART (cocaine and amphet-amine-regulated transcript) - WT (Variant 1) | 9607 | CART | Wild type human protein sequence |
| 28 | CART (cocaine and amphet-amine-regulated transcript) (Variant 2) | | | An alternative exon creates an altered CART peptide from position 54 in the wild type protein |
| 29 | Urocortin - WT (variant 1) | 7349 | UCN | Wild type human protein sequence |
| 30 | Urocortin (Variant 2) | | | An alternative splicing after position 30 in the wild type protein creates a novel Urocortin peptide |
| 31 | Proenkephalin - WT (Variant 1) | 5179 | PENK | Wild type human protein sequence |
| 32 | Proenkephalin (Variant 2) | | | Alternative initiation creates a shorter Synen-kephalin peptide |
| 33 | Stanniocalcin 2 - WT (Variant 1) | 8614 | STC2 | Wild type human protein sequence |
| 34 | Stanniocalcin 2 (Variant 2) | | | An alternative c-terminal exon alters the peptide from position 240 and creates a shorter hormone |
| 35 | Natriuretic peptide precursor B - WT (Variant 1) | 4879 | NPPB | Wild type human protein sequence |
| 36 | Natriuretic peptide precursor B (Variant 2) | | | An alternative c-terminal exon alters the NPPB peptide from position 57 in the wild type protein |
| 37 | Neuromedin U - WT (Variant 1) | 10874 | NMU | Wild type human protein sequence |
| 38 | Neuromedin U (Variant 2) | | | An omission of an alternative exon after position 120 in the wild type protein alters the first four amino acids in the mature peptide |

SEQ ID NOs: 1-19 are nucleotide sequences.

SEQ ID NOs: 20-38 are protein sequences encoded by SEQ ID NOs: 1-19.

"Hormonal Imbalance Variants products", also referred at times as the "hormonal imbalance variants proteins" or "hormonal imbalance variants polypeptides"—are amino acid sequences encoded by the hormonal imbalance variants nucleic acid sequences which are naturally occurring mRNA sequences obtained as a result of alternative splicing. The amino acid sequences may be a peptide, a protein, as well as peptides or proteins having chemically modified amino acids (see below) such as a glycopeptide or glycoprotein. The hormonal imbalance variants products are shown in any one of SEQ ID NOs: 21, 23, 24, 26, 28, 30, 32, 34, 36, and 38. The term also includes homologs (see below) of said sequences in which one or more amino acids has been added, deleted, substituted (see below) or chemically modified (see below) as well as fragments (see below) of this sequence having at least 10 amino acids.

"Fragments of hormonal imbalance related variants nucleic acid sequences"—a partial sequence of any one of SEQ ID NO:2, SEQ ID NO:4, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, which includes the regions which contain the variation in nucleotides between the variant and the original sequences. These regions (in the amino acid level) are as depicted in the above Table 1. Thus, for example, a fragment of SEQ ID NO:2 of 15 b.p. could comprise nucleotides 402-416, 403-417, 404-418, 405-419, 406-420, 407-421, 408-422, 409-423, 410-424, 411-425, 412-426, 413-427, 414-428, or 415-429 of SEQ ID NO:2. These sequences all incorporate the deletion found in SEQ ID NO:2 splice variant compared to original sequence SEQ ID NO:1, thus differentiating any of these fragments from those fragments possibly produced from the original sequence. Larger fragments are similarly constructed. In relation to a splice variant that has an insertion compared to its original sequence, for example SEQ ID NO:7, a 15 b.p. fragment will contain at least one nucleotide from the insertion. Thus, for example, a 15 b.p. fragment of SEQ ID NO:7 could comprise a fragment beginning at nucleotide 191, 192, 193, 194, 195, 196, 197, 198, 199, 200, 201, 202, 203, 204, 205, or 206, which would be a fragment of 15 b.p. entirely within the SEQ ID NO:7 insertion region. A 15 b.p. fragment of SEQ ID NO:7 could also comprise a fragment beginning at nucleotide 178, 179, 180, 181, 182, 183, 184, 185, 186, 187, 188, or 189, which would be a fragment of 15 b.p. encompassing at least one nucleotide from the insertion region of SEQ ID NO:7. (Note that a fragment beginning at 176 or 177, though encompassing the first, and in the case of 177 the second, nucleotide of the SEQ ID NO:7 insertion, would produce 15 b.p. fragments identical to those produced by the original sequence SEQ ID NO:6 from nucleotides 176-190 and 177-191, respectively.) A 15 b.p. fragment of SEQ ID NO:7 could also comprise a fragment beginning at nucleotide 207, 208, 209, 210, 211, 212, 213, 214, 215, 216, 217, 218, 219, or 220, which would be a fragment of 15 b.p. encompassing at least one nucleotide from the insertion region of SEQ ID NO:7. In all cases, larger fragments are similarly constructed. In relation to a splice variant that has a region of different nucleotides compared to its original sequence, for example SEQ ID NO:13, a 15 b.p. fragment will contain at least one nucleotide from the region of differentiation. Thus, for example, a 15 b.p. fragment of SEQ ID NO:13 could comprise a fragment beginning at nucleotide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45, which would be a fragment of 15 b.p. entirely within the SEQ ID NO:13 differentiation region. Alternatively, a 15 b.p. fragment of SEQ ID NO:13 could also comprise a fragment beginning at nucleotide 46, 47, 48, 49, 50, 51, 52, 53, 54, 55, 56, 57, 58, or 59, which would be a fragment of 15 b.p.

encompassing at least one nucleotide from the differentiation region of SEQ ID NO:13. In all cases, larger fragments are similarly constructed.

"Fragments of hormonal Imbalance related variant product"—amino acid sequences coded by the above nucleic acid fragment, containing regions by which the variant differs from the original sequence as indicated in Table 1. Thus, for example, a fragment of SEQ ID NO:24 of 10 amino acids could comprise amino acids 37-46, 38-47, 39-48, 40-49, 41-50, 42-51, 43-52, 44-53, or 45-54 of SEQ ID NO:24. These sequences all incorporate the deletion found in SEQ ID NO:24 splice variant compared to original sequence SEQ ID NO:22, thus differentiating any of these fragments from those fragments possibly produced from the original sequence. Larger fragments are similarly constructed. In relation to a splice variant that has an insertion compared to its original sequence, for example SEQ ID NO:26, a 10 amino acid fragment will contain at least one amino acid from the insertion. Thus, for example, a 10 amino acid fragment of SEQ ID NO:26 could comprise a fragment beginning at nucleotide 63, which would be a fragment of 10 amino acids entirely within the SEQ ID NO:26 insertion region. A 10 amino acid fragment of SEQ ID NO:26 could also comprise a fragment beginning at amino acid 54, 55, 56, 57, 58, 59, 60, 61, or 62, which would be a fragment of 10 amino acids encompassing at least one amino acid from the insertion region of SEQ ID NO:26. A 10 amino acid fragment of SEQ ID NO:26 could also comprise a fragment beginning at amino acid 64, 65, 66, 67, 68, 69, 70, 71, or 72, which would be a fragment of 10 amino acids encompassing at least one amino acid from the insertion region of SEQ ID NO:26. In all cases, larger fragments are similarly constructed. In relation to a splice variant that has a region of different amino acids compared to its original sequence, for example SEQ ID NO:21, a 10 amino acid fragment will contain at least one amino acid from the region of differentiation. Thus, for example, a 10 amino acid fragment of SEQ ID NO:21 could comprise a fragment beginning at amino acid 106, 107, 108, 109, 110, 111, 112, 113, 114, 115, 116, 117, 118, 119, or 120, which would be a fragment of 10 amino acids entirely within the SEQ ID NO:21 differentiation region. Alternatively, a 10 amino acid fragment of SEQ ID NO:21 could also comprise a fragment beginning at amino acid 97, 98, 99, 100, 101, 102, 103, 104, or 105, which would be a fragment of 10 amino acids encompassing at least one amino acid from the differentiation region of SEQ ID NO:21. In all cases, larger fragments are similarly constructed.

"Nucleic acid sequence"—a sequence composed of DNA nucleotides, RNA nucleotides or a combination of both types and may includes natural nucleotides, chemically modified nucleotides and synthetic nucleotides.

"Amino acid sequence"—a sequence composed of any one of the 20 naturally appearing amino acids, amino acids which have been chemically modified (see below), or composed of synthetic amino acids.

"Homologues of variants/products"—amino acid sequences of variants in which one or more amino acids has been added, deleted or replaced. The altered amino acid shall be in regions where the variant differs from the original sequence, for example, according to the explanation in Table 1.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein/peptide) where at least one of its amino acid residues is modified either by natural processes, such as processing or other post-translational modifications, or by chemical modification techniques which are well known in the art. Among the numerous known modifications typical, but not exclusive examples include: acetylation, acylation (e.g., octanoylation), amidation, ADP-ribosylation, glycosylation, GPI anchor formation, covalent attachment of a lipid or lipid derivative, methylation, myristylation, pegylation, prenylation, phosphorylation, ubiquitination, or any similar process.

"Biologically active"—refers to the variant product having some sort of biological activity, for example, capability of binding to the hormonal imbalance product receptor related gene product or to other agonists of the original hormonal imbalance related gene as known.

"Immunologically active"—defines the capability of a natural, recombinant or synthetic variant product, or any fragment thereof, to induce a specific immune response in appropriate animals or cells and to bind with specific antibodies. Thus, for example, an immunologically active fragment of variant product denotes a fragment which retains some or all of the immunological properties of the variant product, e.g., can bind specific anti-variant product antibodies or which can elicit an immune response which will generate such antibodies or cause proliferation of specific immune cells which produce variant.

"Optimal alignment"—is defined as an alignment giving the highest percent identity score. Such alignment can be performed using a variety of commercially available sequence analysis programs, such as the local alignment program LALIGN using a ktup of 1, default parameters and the default PAM. A preferred alignment is the one performed using the CLUSTAL-W program from MacVector™, operated with an open gap penalty of 10.0, an extended gap penalty of 0.1, and a BLOSUM similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence). In case of alignments of known gene sequences with that of the new variant, the optimal alignment invariably included aligning the identical parts of both sequences together, then keeping apart and unaligned the sections of the sequences that differ one from the other.

"Having at least 90% identity", "having at least 91% identity", "having at least 92% identity", etc.—with respect to two amino acid or nucleic acid sequence sequences, refers to the percentage of residues that are identical in the two sequences when the sequences are optimally aligned. Thus, 90% amino acid sequence identity means that 90% of the amino acids in two or more optimally aligned polypeptide sequences are identical. The same holds true for 91% identity, 92% identity, etc.

"Isolated nucleic acid molecule having a variant nucleic acid sequence"—is a nucleic acid molecule that includes the hormonal imbalance related variant nucleic acid coding sequence. Said isolated nucleic acid molecule may include the hormonal imbalance related variant nucleic acid sequence as an independent insert; may include the hormonal imbalance related variant nucleic acid sequence fused to an additional coding sequences, encoding together a fusion protein in which the variant coding sequence is the dominant coding sequence (for example, the additional coding sequence may code for a signal peptide); the hormonal imbalance related variant nucleic acid sequence may be in combination with non-coding sequences, e.g., introns or control elements, such as promoter and terminator elements or 5' and/or 3' untranslated regions, effective for expression of the coding sequence in a suitable host; or may be a vector in which the hormonal imbalance related variant protein coding sequence is heterologous.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences, the substitution may be conservative or non-conservative.

"Antibody"—refers to IgM, IgD, IgA, and IgG antibody. The definition includes polyclonal antibodies or monoclonal antibodies. This term refers to whole antibodies or fragments of the antibodies comprising the antigen-binding domain of the anti-variant product antibodies, e.g. antibodies without the Fc portion, single chain antibodies, fragments consisting of essentially only the variable, antigen-binding domain of the antibody, etc.

"Treating a disease"—refers to administering a therapeutic substance effective to ameliorate symptoms associated with a disease, to lessen the severity or cure the disease, or to prevent the disease from occurring.

"Detection"—refers to a method of detection of a disease, disorder, pathological or normal condition. This term may refer to detection of a predisposition to a disease as well as for establishing the prognosis of the patient by determining the severity of the disease.

"Probe"—the hormonal imbalance variant nucleic acid sequence, or a sequence complementary therewith, when used to detect presence of other similar sequences in a sample or of sequences having some homology with this sequence. The detection is carried out by identification of hybridization complexes between the probe and the assayed sequence. The probe may be attached to a solid support or to a detectable label.

"Original hormonal imbalance related genes"—the amino acid or nucleic acid sequence from which the hormonal imbalance related variants of the invention have been varied as a result of alternative splicing. The original nucleic sequence is the sequence of the human hormonal imbalance related gene depicted as SEQ ID NO:1 for Glucagon and the original amino acid sequence is the sequence encoded by it; SEQ ID NO:3 for Neurotensin and the original amino acid sequence is the sequence encoded by it; SEQ ID NO:6 for Pancreatic Polypeptide and the original amino acid sequence is the sequence encoded by it; SEQ ID NO:8 for CART and the original amino acid sequence is the sequence encoded by it; SEQ ID NO:10 for Urocortin and the original amino acid sequence is the sequence encoded by it; SEQ ID NO:12 for Proenkephalin and the original amino acid sequence is the sequence encoded by it; SEQ ID NO:14 for Stanniocalcin and the original amino acid sequence is the sequence encoded by it; SEQ ID NO:16 for Natriuretic Peptide Precursor B and the original amino acid sequence is the sequence encoded by it; SEQ ID NO:18 for Neuromedin U and the original amino acid sequence is the sequence encoded by it.

SUMMARY OF THE INVENTION

The present invention relates to isolated nucleic acid molecules having a sequence selected from the group consisting of SEQ ID NOs: 2, 4, 5, 7, 9, 11, 13, 15, 17, 19; complements thereof; and fragments thereof comprising at least 15 nucleotides. The present invention relates to isolated nucleic acid molecules comprising SEQ ID NOs: 2, 4, 5, 7, 9, 11, 13, 15, 17, or 19; complements thereof; and isolated nucleic acid molecules comprising fragments of SEQ ID NOs: 2, 4, 5, 7, 9, 11, 13, 15, 17, or 19 comprising at least 15 nucleotides.

The present invention relates to PCR primers which can amplify products using sequences of SEQ ID NOs: 2, 4, 5, 7, 9, 11, 13, 15, 17, or 19 as templates.

The present invention relates to methods of screening, diagnosing and monitoring individuals for hormonal imbalance. The methods comprise detecting the presence, absence, or quantity of a transcription product that comprises a sequence selected from the group consisting of SEQ ID NOs: 2, 4, 5, 7, 9, 11, 13, 15, 17, and 19 in a sample. The presence or quantity of said transcription product is indicative of hormonal imbalance. The present invention relates to methods of treating hormonal imbalance comprising administering to a mammal in need thereof a therapeutically effective amount of a pharmaceutical composition comprising: (a) an isolated amino acid sequence selected from the group consisting of SEQ ID NO:21, SEQ ID NO:23, SEQ ID NO:24, SEQ ID NO:26, SEQ ID NO:28, SEQ ID NO:30, SEQ ID NO:32, SEQ ID NO:34, SEQ ID NO:36, SEQ ID NO:38, and a peptide comprising at least a 10 contiguous amino acid segment thereof; and (b) a carrier.

The present invention relates to kits for screening, diagnosing and monitoring an individual for hormonal imbalance.

The present invention relates to an isolated amino acid sequence selected from the group consisting of SEQ ID NOs: 21, 23, 24, 26, 28, 30, 32, 34, 36, and 38 and immunogenic fragments thereof.

The present invention relates to antibodies which specifically bind to an epitope on an amino acid sequence selected from the group consisting of SEQ ID NOs: 21, 23, 24, 26, 28, 30, 32, 34, 36, and 38.

The present invention relates to antibodies which specifically bind to an epitope on an amino acid sequence selected from the group consisting of SEQ ID NOs: 21, 23, 24, 26, 28, 30, 32, 34, 36, and 38 that are linked to detectable labels or active agents.

The present invention relates to a pharmaceutical composition comprising antibodies which specifically bind to an epitope on an amino acid sequence selected from the group consisting of SEQ ID NOs: 21, 23, 24, 26, 28, 30, 32, 34, 36, and 38 that are linked to active agents.

The present invention relates to a pharmaceutical composition comprising a bioactive peptide derived from an amino acid sequence selected from the group consisting of SEQ ID NOs: 21, 23, 24, 26, 28, 30, 32, 34, 36, and 38 that are linked to active agents.

The present invention relates to methods of treating an individual suspected of suffering from hormonal imbalance. The methods comprise the step of administering to individuals antibodies which specifically bind to an epitope on an amino acid sequence selected from the group consisting of SEQ ID NOs: 21, 23, 24, 26, 28, 30, 32, 34, 36, and 38 that are linked to active agents.

The present invention relates to methods for the identification of compounds capable of affecting the binding affinity of hormonal imbalance related proteins to the receptors of said proteins comprising the steps of: (a) providing an amino acid sequence selected from the group consisting of SEQ ID NO:21, SEQ ID NO:23, SEQ ID NO:24, SEQ ID NO:26, SEQ ID NO:28, SEQ ID NO:30, SEQ ID NO:32, SEQ ID NO:34, SEQ ID NO:36, and SEQ ID NO:38; (b) contacting a candidate compound with the amino acid sequence in the presence of at least one receptor of an hormonal Imbalance related gene; (c) determining the effect of the candidate compound on the binding of the amino acid sequence to the at least one receptor; and (d) selecting a compound capable of affecting the binding affinity of hormonal Imbalance related proteins to the receptors of said proteins.

The present invention relates to methods for determining the ratio between the level of an hormonal imbalance related protein variant in a first biological sample and a variant produced by alternative splicing in a second biological sample comprising the steps of: (a) determining the level of a first amino acid sequence of an hormonal imbalance related gene variant in a first biological sample; (b) determining the level of a second amino acid sequence of an alternative splicing form of the variant in a second biological sample; and (c) comparing the levels obtained in step (a) and step (b) to give a ratio.

BRIEF DESCRIPTION OF THE DRAWINGS

FIG. 1 shows alignment of two amino acid sequences of human origin (depicted in SEQ ID NO:20 to SEQ ID NO:21) to each other;

FIG. 2 shows multiple alignment of three amino acid sequences of human origin (depicted in SEQ ID NO:22 to SEQ ID NO:24) to each other;

FIG. 3 shows alignment of two amino acid sequences of human origin (depicted in SEQ ID NO:25 to SEQ ID NO:26) to each other;

FIG. 4 shows alignment of two amino acid sequences of human origin (depicted in SEQ ID NO:27 to SEQ ID NO:28) to each other;

FIG. 5 shows alignment of two amino acid sequences of human origin (depicted in SEQ ID NO:29 to SEQ ID NO:30) to each other;

FIG. 6 shows alignment of two amino acid sequences of human origin (depicted in SEQ ID NO:31 to SEQ ID NO:32) to each other;

FIG. 7 shows alignment of two amino acid sequences of human origin (depicted in SEQ ID NO:33 to SEQ ID NO:34) to each other;

FIG. 8 shows alignment of two amino acid sequences of human origin (depicted in SEQ ID NO:35 to SEQ ID NO:36) to each other;

FIG. 9 shows alignment of two amino acid sequences of human origin (depicted in SEQ ID NO:37 to SEQ ID NO:38) to each other;

FIG. 10 shows alignment of two nucleic acid sequences of human origin (depicted in SEQ ID NO:1 to SEQ ID NO:2) to each other;

FIG. 11 shows multiple alignment of three nucleic acid sequences of human origin (depicted in SEQ ID NO:3 to SEQ ID NO:5) to each other;

FIG. 12 shows alignment of two nucleic acid sequences of human origin (depicted in SEQ ID NO:6 to SEQ ID NO:7) to each other;

FIG. 13 shows alignment of two nucleic acid sequences of human origin (depicted in SEQ ID NO:8 to SEQ ID NO:9) to each other;

FIG. 14 shows multiple alignment of two amino acid sequences of human origin (depicted in SEQ ID NO:10 to SEQ ID NO:11) to each other.

FIG. 15 shows multiple alignment of two amino acid sequences of human origin (depicted in SEQ ID NO:12 to SEQ ID NO:13) to each other.

FIG. 16 shows multiple alignment of two amino acid sequences of human origin (depicted in SEQ ID NO:14 to SEQ ID NO:15) to each other.

FIG. 17 shows multiple alignment of two amino acid sequences of human origin (depicted in SEQ ID NO:16 to SEQ ID NO:17) to each other.

FIG. 18 shows multiple alignment of two amino acid sequences of human origin (depicted in SEQ ID NO:18 to SEQ ID NO:19) to each other.

DETAILED DESCRIPTION OF PREFERRED EMBODIMENTS

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Hormonal Imbalance Variants Nucleic Acid Sequence

The nucleic acid sequences of the invention include nucleic acid sequences which encode Hormonal Imbalance variants products and fragments and analogs thereof. The nucleic acid sequences may alternatively be sequences complementary to the above coding sequences, or to regions of said coding sequence. The length of the complementary sequences is sufficient to avoid the expression of the coding sequence. The nucleic acid sequences may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand. The nucleic acid sequences may also both include dNTPs, rNTPs as well as non-naturally occurring sequences. The sequence may also be a part of a hybrid between an amino acid sequence and a nucleic acid sequence.

In a general embodiment, the nucleic acid sequence has at least 90%, at least 91%, at least 92%, at least 93%, at least 94%, at least 95%, at least 96%, at least 97%, at least 98%, or at least 99% identity with any one of the sequences identified as SEQ ID NO:2 or SEQ ID NO:4 or SEQ ID NO:5 or SEQ ID NO:7 or SEQ ID NO:9 or SEQ ID NO:11 or SEQ ID NO:13 or SEQ ID NO:15 or SEQ ID NO:17 or SEQ ID NO:19.

The nucleic acid sequences may include the coding sequence by itself. By another alternative, the coding region may be in combination with additional coding sequences, such as those coding for fusion protein or signal peptides, in combination with non-coding sequences, such as introns and control elements, promoter and terminator elements or 5' and/or 3' untranslated regions, effective for expression of the coding sequence in a suitable host, and/or in a vector or host environment in which the variant nucleic acid sequences is introduced as a heterologous sequence.

The nucleic acid sequences of the present invention may also have the hormonal imbalance variants products coding sequences fused in-frame to a marker sequence which allows for purification of the variant product. The marker sequence may be, for example, a hexahistidine tag to provide for purification of the mature polypeptide fused to the marker in the case of a bacterial host, or the marker sequence may be a hemagglutinin (HA) tag when a mammalian host, e.g. COS-7 cells, is used. The HA tag corresponds to an epitope derived from the influenza hemagglutinin protein (Wilson, I., et al. Cell 37:767 (1984)).

Also included in the scope of the invention are fragments as defined above also referred to herein as oligonucleotides, typically having at least 17 bases, preferably 17-30 bases corresponding to a region of the coding-sequence nucleic acid sequence. The fragments may be used as probes, primers, and when complementary also as antisense agents, and the like, according to known methods.

As indicated above, the nucleic acid sequence may be substantially as depicted in SEQ ID NO:2 or SEQ ID NO:4 or SEQ ID NO:5 or SEQ ID NO:7 or SEQ ID NO:9 or SEQ ID NO:11 or SEQ ID NO:13 or SEQ ID NO:15 or SEQ ID NO:17 or SEQ ID NO:19 or fragments thereof or sequences having at least 90%, at least 91%, at least 92%, at least 93%, at least 94%, at least 95%, at least 96%, at least 97%, at least 98%, or at least 99% identity to the above sequence as explained above. Alternatively, due to the degenerative nature of the genetic code, the sequence may be a sequence coding for any one of the amino acid sequences of SEQ ID NO:21 or SEQ ID NO:23 or SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38, or fragments or analogs of said amino acid sequence.

A. Preparation of Nucleic Acid Sequences

The nucleic acid sequences may be obtained by screening cDNA libraries using oligonucleotide probes which can hybridize to or PCR-amplify nucleic acid sequences which encode the Hormonal Imbalance variants products disclosed above. cDNA libraries prepared from a variety of tissues are commercially available, and procedures for screening and isolating cDNA clones are well-known to those of skill in the art. Such techniques are described in, for example, Sambrook et al. (1989) Molecular Cloning: A Laboratory Manual (2nd Edition), Cold Spring Harbor Press, Plainview, N.Y. and Ausubel F M et al. (1989) Current Protocols in Molecular Biology, John Wiley & Sons, New York, N.Y.

The nucleic acid sequences may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the Marathon RACE kit (Clontech, Cat. # K1802-1).

Alternatively, the technique of "restriction-site" PCR (Gobinda et al. PCR Methods Appl. 2:318-22 (1993)), which uses universal primers to retrieve flanking sequence adjacent a known locus, may be employed. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, T. et al., Nucleic Acids Res. 16:8186 (1988)). The primers may be designed using OLIGO® 4.06 Primer Analysis Software (1992; National Biosciences Inc, Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Capture PCR (Lagerstrom, M. et al., PCR Methods Appl. 1:111-19 (1991)) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J. D., et al., Nucleic Acids Res. 19:3055-60 (1991). Additionally, one can use PCR, nested primers and PromoterFinder™ libraries to "walk in" genomic DNA (PromoterFinder™; Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes.

A randomly primed library may be particularly useful if an oligo d(T) library does not yield a full-length cDNA. Genomic libraries are useful for extension into the 5' non-translated regulatory region.

The nucleic acid sequences and oligonucleotides of the invention can also be prepared by solid-phase methods, according to known synthetic methods. Typically, fragments of up to about 100 bases are individually synthesized, then joined to form continuous sequences up to several hundred bases.

B. Use of Hormonal Imbalance Variants Nucleic Acid Sequences for the Production of Hormonal Imbalance Variants Products In accordance with the present invention, nucleic acid sequences specified above may be used as recombinant DNA molecules that direct the expression of Hormonal Imbalance variant products.

As will be understood by those of skill in the art, it may be advantageous to produce Hormonal Imbalance variants product-encoding nucleotide sequences possessing codons other than those which appear in SEQ ID NO:2 or SEQ ID NO:4 or SEQ ID NO:5 or SEQ ID NO:7 or SEQ ID NO:9 or SEQ ID NO:11 or SEQ ID NO:13 or SEQ ID NO:15 or SEQ ID NO:17 or SEQ ID NO:19, which are those which naturally occur in the human genome. Codons preferred by a particular prokaryotic or eukaryotic host (Murray, E. et al. Nucleic Acids Res. 17:477-508 (1989)) can be selected, for example, to increase the rate of variant product expression or to produce recombinant RNA transcripts having desirable properties, such as a longer half-life, than transcripts produced from naturally occurring sequences.

The nucleic acid sequences of the present invention can be engineered in order to alter Hormonal Imbalance variants products coding sequences for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, etc.

The present invention also includes recombinant constructs comprising one or more of the sequences as broadly described above. The constructs comprise a vector, such as a plasmid or viral vector, into which nucleic acid sequences of the invention have been inserted, in a forward or reverse orientation. In a preferred aspect of this embodiment, the constructs further comprise regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al. (supra).

The present invention also relates to host cells which are genetically engineered with vectors of the invention and the production of the product of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the expression of the variant nucleic acid sequence. The culture conditions, such as temperature, pH and the like, are those previously used with the host cell selected for expression, and will be apparent to those skilled in the art.

The nucleic acid sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA; viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: LTR or SV40 promoter, the *E. coli* lac or trp promoter, the phage lambda PL promoter, and other promoters known to control expression of genes in prokaryotic or eukaryotic cells or their viruses. The expression vectors also contain a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vectors containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces, Salmonella typhimurium*; fungal cells, such as yeast; insect cells such as *Drosophila* and *Spodoptera* Sf9; animal cells such as CHO, COS, HEK 293 or Bowes melanoma; adenoviruses; plant cells; etc. The selection of an appropriate host is deemed to be within the scope of those skilled in the art from the teachings herein. The invention is not limited by the host cells employed.

In bacterial systems, a number of expression vectors may be selected depending upon the use intended for the Hormonal Imbalance variant product. For example, when large quantities of Hormonal Imbalance variant product are needed for the induction of antibodies, vectors which direct high level expression of fusion proteins that are readily purified may be desirable. Such vectors include, but are not limited to, multifunctional *E. coli* cloning and expression vectors such as Bluescript® (Stratagene), in which the Hormonal Imbalance variants polypeptides coding sequence may be ligated into the vector in-frame with sequences for the amino-terminal Met and the subsequent 7 residues of beta-galactosidase so that a hybrid protein is produced; pIN vectors (Van Heeke & Schuster J. Biol. Chem. 264:5503-5509 (1989)); pET vectors (Novagen, Madison Wis.); and the like.

In the yeast *Saccharomyces cerevisiae*, a number of vectors containing constitutive or inducible promoters such as alpha factor, alcohol oxidase and PGH may be used. For reviews, see Ausubel et al. (supra) and Grant et al. (Methods in Enzymology 153:516-544 (1987)).

In cases where plant expression vectors are used, the expression of a sequence encoding variant products may be driven by any of a number of promoters. For example, viral promoters such as the 35S and 19S promoters of CaMV (Brisson et al., Nature 310:511-514 (1984)) may be used alone or in combination with the omega leader sequence from TMV (Takamatsu et al., EMBO J. 6:307-311 (1987)). Alternatively, plant promoters such as the small subunit of RUBISCO (Coruzzi et al., EMBO J. 3:1671-1680 (1984); Broglie et al., Science 224:838-843 (1984)); or heat shock promoters (Winter J and Sinibaldi R. M., Results Probl. Cell Differ. 17:85-105 (1991)) may be used. These constructs can be introduced into plant cells by direct DNA transformation or pathogen-mediated transfection. For reviews of such techniques, see Hobbs S. or Murry L. E. (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

Hormonal Imbalance variants products may also be expressed in an insect system. In one such system, *Autographa californica* nuclear polyhedrosis virus (AcNPV) is used as a vector to express foreign genes in *Spodoptera frugiperda* cells or in *Trichoplusia* larvae. The Hormonal Imbalance variants products coding sequence may be cloned into a nonessential region of the virus, such as the polyhedrin gene, and placed under control of the polyhedrin promoter. Successful insertion of Hormonal Imbalance coding sequences will render the polyhedrin gene inactive and produce recombinant virus lacking coat protein coat. The recombinant viruses are then used to infect *S. frugiperda* cells or *Trichoplusia* larvae in which variant protein is expressed (Smith et al., J. Virol. 46:584 (1983); Engelhard, E. K. et al., Proc. Nat. Acad. Sci. USA 91:3224-7 (1994)).

In mammalian host cells, a number of viral-based expression systems may be utilized. In cases where an adenovirus is used as an expression vector, Hormonal Imbalance variants products coding sequences may be ligated into an adenovirus transcription/translation complex consisting of the late promoter and tripartite leader sequence. Insertion in a nonessential E1 or E3 region of the viral genome will result in a viable virus capable of expressing variant protein in infected host cells (Logan and Shenk, Proc. Natl. Acad. Sci. USA 81:3655-59 (1984). In addition, transcription enhancers, such as the Rous sarcoma virus (RSV) enhancer, may be used to increase expression in mammalian host cells.

Specific initiation signals may also be required for efficient translation of variants products coding sequences. These signals include the ATG initiation codon and adjacent sequences. In cases where Hormonal Imbalance variants products coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., Results Probl. Cell Differ. 20:125-62 (1994); Bittner et al., Meth. Enzymol. 153:516-544 (1987)).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre-pro" form of the protein may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express variant products may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M., et al., Cell 11:223-32 (1977)) and adenine phosphoribosyltransferase (Lowy I., et al., Cell 22:817-23 (1980)) genes which can be employed in tk- or aprt-cells, respectively. Also, antimetabolite, antibiotic or herbicide resistance can be used as the basis for selection, for example, dhfr which confers resistance to methotrexate (Wigler M., et al., Proc. Natl. Acad. Sci. USA 77:3567-70, (1980)); npt, which confers resistance to the aminoglycosides neomycin and G-418 (Colbere-Garapin, F. et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan, Proc. Natl. Acad. Sci. USA 85:8047-51, (1988)). The use of visible markers has gained popularity with such markers as anthocyanins, beta-glucuronidase and its substrate, GUS, and luciferase and its substrates, luciferin and ATP, being widely used not only to identify transformants, but also to quantify the amount of transient or stable protein expression attributable to a specific vector system (Rhodes, C. A. et. al., Methods Mol. Biol. 55:121-131 (1995)).

Host cells transformed with nucleotide sequences encoding Hormonal Imbalance variants products may be cultured under conditions suitable for the expression and recovery of the encoded protein from cell culture. The product produced by a recombinant cell may be secreted or contained intracellularly depending on the sequence and/or the vector used. As will be understood by those of skill in the art, expression vectors containing nucleic acid sequences encoding Hormonal Imbalance variants products can be designed with signal sequences which direct secretion of Hormonal Imbalance variants products through a prokaryotic or eukaryotic cell membrane.

The Hormonal Imbalance variants products may also be expressed as recombinant proteins with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of a protease-cleavable polypeptide linker sequence between the purification domain and Hormonal Imbalance variants products is useful to facilitate purification. One such expression vector provides for expression of a fusion protein comprising a variant polypeptide fused to a polyhistidine region separated by an enterokinase cleavage site. The histidine residues facilitate purification on IMIAC (immobilized metal ion affinity chromatography, as described in Porath, et al., Protein Expr.

Purif. 3:263-281 (1992)) while the enterokinase cleavage site provides a means for isolating variant polypeptide from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

The Hormonal Imbalance variants products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

C. Diagnostic Applications Utilizing Nucleic Acid Sequences

The nucleic acid sequences of the present invention may be used for a variety of diagnostic purposes. The nucleic acid sequences may be used to detect and quantitate expression of the Hormonal Imbalance variant in patient's cells, e.g. biopsied tissues, by detecting the presence of mRNA coding for the Hormonal Imbalance variants products. Alternatively, the assay may be used to detect the soluble variants in the serum or blood. This assay typically involves obtaining total mRNA from the tissue or serum and contacting the mRNA with a nucleic acid probe. The probe is a nucleic acid molecule of at least 20 nucleotides, preferably 20-30 nucleotides, capable of specifically hybridizing with a sequence included within the sequence of a nucleic acid molecule encoding the Hormonal Imbalance variant product under hybridizing conditions, detecting the presence of mRNA hybridized to the probe, and thereby detecting the expression of variant. This assay can be used to distinguish between absence, presence, and excess expression of Hormonal Imbalance variants products and to monitor levels of Hormonal Imbalance variants expression during therapeutic intervention. In addition, the assay may be used to compare the levels of the Hormonal Imbalance variant of the invention to the levels of the original Hormonal Imbalance sequence from which it has been varied or to levels of each other, which comparison may have some physiological meaning.

The invention also contemplates the use of the nucleic acid sequences as a diagnostic for diseases resulting from inherited defective variants sequences, or diseases in which the ratio of the amount of the original Hormonal Imbalance sequence from which the Hormonal Imbalance variants were varied to the novel Hormonal Imbalance variants of the invention is altered. These sequences can be detected by comparing the sequences of the defective (i.e., mutant) Hormonal Imbalance variants coding region with that of a normal coding region. Association of the sequence coding for mutant Hormonal Imbalance variants products with abnormal variants products activity may be verified. In addition, sequences encoding mutant Hormonal Imbalance variants products can be inserted into a suitable vector for expression in a functional assay system (e.g., colorimetric assay, complementation experiments in a variant protein deficient strain of HEK293 cells) as yet another means to verify or identify mutations. Once mutant genes have been identified, one can then screen populations of interest for carriers of the mutant gene.

Individuals carrying mutations in the nucleic acid sequences of the present invention may be detected at the DNA level by a variety of techniques. Nucleic acids used for diagnosis may be obtained from a patient's cells, including but not limited to such as from blood, urine, saliva, placenta, tissue biopsy and autopsy material. Genomic DNA may be used directly for detection or may be amplified enzymatically by using PCR (Saiki, et al., Nature 324:163-166 (1986)) prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method (e.g. Cotton, et al., Proc. Natl. Acad. Sci. USA 85:4397-4401 (1985)), or by differences in melting temperatures. "Molecular beacons" (Kostrikis L. G. et al., Science 279:1228-1229 (1998)), hairpin-shaped, single-stranded synthetic oligonucleotides containing probe sequences which are complementary to the nucleic acid of the present invention, may also be used to detect point mutations or other sequence changes as well as monitor expression levels of variant product. Such diagnostics would be particularly useful for prenatal testing.

Another method for detecting mutations uses two DNA probes which are designed to hybridize to adjacent regions of a target, with abutting bases, where the region of known or suspected mutation(s) is at or near the abutting bases. The two probes may be joined at the abutting bases, e.g., in the presence of a ligase enzyme, but only if both probes are correctly base paired in the region of probe junction. The presence or absence of mutations is then detectable by the presence or absence of ligated probe.

Also suitable for detecting mutations in the Hormonal Imbalance variants products coding sequences are oligonucleotide array methods based on sequencing by hybridization (SBH), as described, for example, in U.S. Pat. No. 5,547, 839. In a typical method, the DNA target analyte is hybridized with an array of oligonucleotides formed on a microchip. The sequence of the target can then be "read" from the pattern of target binding to the array.

D. Therapeutic Applications of Nucleic Acid Sequences

Nucleic acid sequences of the invention may also be used for therapeutic purposes. Referring to a second aspect of the invention (i.e. inhibition of expression of Hormonal Imbalance variants), expression of Hormonal Imbalance variants products may be modulated through antisense technology, which controls gene expression through hybridization of complementary nucleic acid sequences, i.e. antisense DNA or RNA, to the control, 5' or regulatory regions of the gene encoding variant product. For example, the 5' coding portion of the nucleic acid sequence which codes for the product of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the nucleic acid sequence involved in transcription (Lee et al., Nucl. Acids Res. 6:3073 (1979); Cooney et al., Science 241:456 (1988); and Dervan et al., Science 251:1360 (1991)), thereby preventing transcription and the production of the variant products. An antisense RNA oligonucleotide hybridizes to the mRNA in vivo and blocks translation of the mRNA molecule into the variant products (Okano, J. Neurochem. 56:560 (1991)). The antisense constructs can be delivered to cells by procedures known in the art such that the antisense RNA or DNA may be expressed in vivo. The antisense may be an antisense mRNA or DNA sequence capable of coding such antisense mRNA. The antisense mRNA or the DNA coding thereof can be complementary to the full sequence of nucleic acid sequences coding for the Hormonal Imbalance variant protein or to a fragment of such a sequence which is sufficient to inhibit production of a protein product. Antisense technologies can also be used for inhibiting expression of one variant as compared to the other, or inhibiting the expression of the variant/s as compared to the original sequence.

Turning now to the first aspect of the invention, i.e. expression of Hormonal Imbalance variants, expression of Hormonal Imbalance variants products may be increased by providing coding sequences for coding for said Hormonal Imbalance variants products under the control of suitable control elements ending its expression in the desired host.

The nucleic acid sequences of the invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The products of the invention may also be employed in accordance with the present invention by expression of such polypeptides in vivo, which is often referred to as "gene therapy." Cells from a patient may be engineered with a nucleic acid sequence (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by procedures known in the art. As known in the art, a producer cell for producing a retroviral particle containing RNA encoding the polypeptides of the present invention may be administered to a patient for engineering cells in vivo and expression of the polypeptide in vivo. These and other methods for administering products of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, psi-2, psi-AM, PA12, T19-14X, VT-19-17-H2, psi-CRE, psi-CRIP, GP+E-86, GP+en-vAm12, and DAN cell lines as described in Miller (Human Gene Therapy, Vol. 1, pg. 5-14, (1990)). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The genes introduced into cells may be placed under the control of inducible promoters, such as the radiation-inducible Egr-1 promoter (Maceri, H. J., et al., Cancer Res. 56(19): 4311 (1996)), to stimulate variant production or antisense inhibition in response to radiation, e.g., radiation therapy for treating tumors.

Hormonal Imbalance Variants Products

The substantially purified Hormonal Imbalance variant product of the invention has been defined above as the product coded from the nucleic acid sequence of the invention. Preferably the amino acid sequence is an amino acid sequence having at least 90%, at least 91%, at least 92%, at least 93%, at least 94%, at least 95%, at least 96%, at least 97%, at least 98%, or at least 99% identity to a sequence identified as SEQ ID NO:21 or SEQ ID NO:23 to SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38. The protein or polypeptide may be in mature and/or modified form, also as defined above, for example, modified by cleavage of the leader sequence. Also contemplated are protein fragments having at least 10 contiguous amino acid residues, preferably at least 10-20 residues, derived from the Hormonal Imbalance variant products, as well as homologues as explained above.

The sequence variations are preferably those that are considered conserved substitutions, as defined above. Thus, for example, a protein with a sequence having at least 90%, at least 91%, at least 92%, at least 93%, at least 94%, at least 95%, at least 96%, at least 97%, at least 98%, or at least 99% sequence identity with the products identified as SEQ ID NO:21 or SEQ ID NO:23 to SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38, preferably by utilizing conserved substitutions as defined above is also part of the invention, and provided that it is not identical to the original peptide from which it has been varied (typically the substitutions are in regions where the variant differs from the original sequence as for example in Table 1). In a more specific embodiment, the protein has or contains the sequence identified SEQ ID NO:21 or SEQ ID NO:23 to SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38. The Hormonal Imbalance variants products may be (i) one in which one or more of the amino acid residues in a sequence listed above are substituted with a conserved or non-conserved amino acid residue (preferably a conserved amino acid residue), or (ii) one in which one or more of the amino acid residues includes a substituent group, or (iii) one in which the Hormonal Imbalance variants products is fused with another compound, such as a compound to increase the half-life of the protein (for example, polyethylene glycol (PEG)), or a moiety which serves as targeting means to direct the protein to its target tissue or target cell population (such as an antibody), or (iv) one in which additional amino acids are fused to the Hormonal Imbalance variant product. Such fragments, variants and derivatives are deemed to be within the scope of those skilled in the art from the teachings herein.

A. Preparation of Hormonal Imbalance Variants Products

Recombinant methods for producing and isolating the Hormonal Imbalance variant products, and fragments of the protein are described above.

In addition to recombinant production, fragments and portions of variant products may be produced by direct peptide synthesis using solid-phase techniques (cf. Stewart et al., (1969) Solid-Phase Peptide Synthesis, WH Freeman Co, San Francisco; Merrifield J., J. Am. Chem. Soc. 85:2149-2154 (1963)). In vitro peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Fragments of Hormonal Imbalance variants products may be chemically synthesized separately and combined using chemical methods to produce the full length molecule.

B. Therapeutic Uses and Compositions Utilizing the Hormonal Imbalance Variants Products The Hormonal Imbalance variants products of the invention are generally useful in treating hormonal imbalance.

Hormonal Imbalance variant products or fragments may be administered by any of a number of routes and methods designed to provide a consistent and predictable concentration of compound at the target organ or tissue. The product-containing compositions may be administered alone or in combination with other agents, such as stabilizing compounds, and/or in combination with other pharmaceutical agents such as drugs or hormones.

Hormonal Imbalance variants product-containing compositions may be administered by a number of routes including, but not limited to oral, subcutaneous, intravenous, intramuscular, transdermal, subcutaneous, topical, sublingual, or rectal means as well as by nasal application. Hormonal Imbalance variant product-containing compositions may also be administered via liposomes. Such administration routes and appropriate formulations are generally known to those of skill in the art.

The Hormonal Imbalance variants products can be given via intravenous or intraperitoneal injection. Similarly, the product may be injected to other localized regions of the body. The product may also be administered via nasal insufflation. Enteral administration is also possible. For such administration, the product should be formulated into an appropriate capsule or elixir for oral administration, or into a suppository for rectal administration.

The foregoing exemplary administration modes will likely require that the product be formulated into an appropriate carrier, including, e.g. ointments, gels, or suppositories. Appropriate formulations are well known to persons skilled in the art.

Dosage of the product will vary, depending upon the potency and therapeutic index of the particular polypeptide selected.

A therapeutic composition for use in the treatment method can include the product in a sterile injectable solution, the polypeptide in an oral delivery vehicle, the product in an aerosol suitable for nasal administration, or the product in a nebulized form, all prepared according to well known methods. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The product of the invention may also be used to modulate endothelial differentiation and proliferation as well as to modulate apoptosis either ex vivo or in vitro, for example, in cell cultures.

Anti-Variant Antibodies

A. Synthesis

In still another aspect of the invention, the purified variants products are used to produce anti-variant antibodies which have diagnostic and therapeutic uses related to the activity, distribution, and expression of the Hormonal Imbalance variants products.

Antibodies to the Hormonal Imbalance variant may be generated by methods well known in the art. Such antibodies may include, but are not limited to, polyclonal, monoclonal, chimeric, humanized, single chain, Fab fragments and fragments produced by an Fab expression library. Antibodies, i.e., those which inhibit dimer formation, are especially preferred for therapeutic use.

A fragment of the Hormonal Imbalance variants products for antibody induction is not required to feature biological activity but has to feature immunological activity; however, the protein fragment or oligopeptide must be antigenic. Peptides used to induce specific antibodies may have an amino acid sequence consisting of at least five amino acids, preferably at least 10 amino acids of the sequences specified in SEQ ID NO:21 or SEQ ID NO:23 to SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38. Preferably they should mimic a portion of the amino acid sequence of the natural protein and may contain the entire amino acid sequence of a small, naturally occurring molecule. Short stretches of Hormonal Imbalance variants proteins amino acids may be fused with those of another protein such as keyhole limpet hemocyanin and antibody produced against the chimeric molecule. Procedures well known in the art can be used for the production of antibodies to Hormonal Imbalance variants products.

For the production of antibodies, various hosts including goats, rabbits, rats, mice, etc. may be immunized by injection with Hormonal Imbalance variants products or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to Hormonal Imbalance variants protein may be prepared using any technique which provides for the production of antibody molecules by continuous cell lines in culture. These include, but are not limited, to the hybridoma technique originally described by Koehler and Milstein (Nature 256:495-497 (1975)), the human B-cell hybridoma technique (Kosbor et al., Immunol. Today 4:72 (1983); Cote et al., Proc. Natl. Acad. Sci. USA 80:2026-2030 (1983)) and the EBV-hybridoma technique (Cole, et al., Mol. Cell Biol. 62:109-120 (1984)).

Techniques developed for the production of "chimeric antibodies", the splicing of mouse antibody genes to human antibody genes to obtain a molecule with appropriate antigen specificity and biological activity, can also be used (Morrison et al., Proc. Natl. Acad. Sci. USA 81:6851-6855 (1984); Neuberger et al., Nature 312:604-608 (1984); Takeda et al., Nature 314:452-454 (1985)). Alternatively, techniques described for the production of single chain antibodies (U.S. Pat. No. 4,946,778) can be adapted to produce single-chain antibodies specific for the variant protein.

Antibodies may also be produced by inducing in vivo production in the lymphocyte population or by screening recombinant immunoglobulin libraries or panels of highly specific binding reagents as disclosed in Orlandi et al. (Proc. Natl. Acad. Sci. USA 86:3833-3837 (1989)), and Winter G and Milstein C. (Nature 349:293-299 (1991)).

Antibody fragments which contain specific binding sites for the Hormonal Imbalance variant protein may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W. D. et al., Science 256:1275-1281 (1989)).

B. Diagnostic Applications of Antibodies

A variety of protocols for competitive binding or immunoradiometric assays using either polyclonal or monoclonal antibodies with established specificities are well known in the art. Such immunoassays typically involve the formation of complexes between the Hormonal Imbalance variants products and its specific antibody and the measurement of complex formation. A two-site, monoclonal-based immunoassay utilizing monoclonal antibodies reactive to two noninterfering epitopes on a specific variant product is preferred, but a competitive binding assay may also be employed. These assays are described in Maddox D. E., et al. (J. Exp. Med. 158:1211 (1983)).

Antibodies which specifically bind the Hormonal Imbalance variant product are useful for the diagnosis of conditions or diseases characterized by expression of the novel Hormonal Imbalance variants of the invention (where normally it is not expressed) by over or under expression of Hormonal Imbalance variants as well as for detection of diseases in which the proportion between the amount of the Hormonal Imbalance variants of the invention and the original Hormonal Imbalance sequence from which it varied is altered. Alternatively, such antibodies may be used in assays to monitor patients being treated with Hormonal Imbalance variants products. Diagnostic assays for variants proteins include methods utilizing the antibody and a label to detect variants products in human body fluids or extracts of cells or tissues. The products and antibodies of the present invention may be used with or without modification. Frequently, the proteins and antibodies will be labeled by joining them, either covalently or noncovalently, with a reporter molecule. A wide variety of reporter molecules are known in the art.

A variety of protocols for measuring the Hormonal Imbalance variants products, using either polyclonal or monoclonal antibodies specific for the respective protein are known in the art. Examples include enzyme-linked immunosorbent assay (ELISA), radioimmunoassay (RIA), and fluorescent activated cell sorting (FACS). As noted above, a two-site, monoclonal-based immunoassay utilizing monoclonal antibodies reactive to two non-interfering epitopes on Hormonal Imbalance variants products is preferred, but a competitive binding assay may be employed. These assays are described, among other places, in Maddox, et al. (supra). Such protocols provide a basis for diagnosing altered or abnormal levels of Hormonal Imbalance variants products expression. Normal or standard values for Hormonal Imbalance variants products expression are established by combining body fluids or cell extracts taken from normal subjects, preferably human, with antibodies to Hormonal Imbalance variants products under conditions suitable for complex formation which are well known in the art. The amount of standard complex formation may be quantified by various methods, preferably by photometric methods. Then, standard values obtained from normal samples may be compared with values obtained from samples from subjects potentially affected by disease. Deviation between standard and subject values establishes the presence of disease state.

The antibody assays are useful to determine the level of Hormonal Imbalance variants products present in a body fluid sample, in order to determine whether it is being expressed at all, whether it is being overexpressed or underexpressed in the tissue, or as an indication of how Hormonal Imbalance variants levels of variable products are responding to drug treatment.

C. Therapeutic Uses of Antibodies

In addition to their diagnostic use, the antibodies may have a therapeutical utility in blocking or decreasing the activity of the hormonal Imbalance variants products in pathological conditions where beneficial effect can be achieved by such a decrease.

The antibody employed is preferably a humanized monoclonal antibody, or a human Mab produced by known globulin-gene library methods. The antibody is administered typically as a sterile solution by IV injection, although other parenteral routes may be suitable. Typically, the antibody is administered in an amount between about 1-15 mg/kg body weight of the subject. Treatment is continued, e.g., with dosing every 1-7 days, until a therapeutic improvement is seen.

Although the invention has been described with reference to specific methods and embodiments, it is appreciated that various modifications and changes may be made without departing from the invention.

Example 1

Separation

Sf-9 cells are infected with Hormonal Imbalance variants expressing baculovirus (AC-hormonal Imbalance variant) comprising the amino acid sequence of SEQ ID NO:21 or SEQ ID NO:23 to SEQ ID NO:24 or SEQ ID NO:26 or SEQ ID NO:28 or SEQ ID NO:30 or SEQ ID NO:32 or SEQ ID NO:34 or SEQ ID NO:36 or SEQ ID NO:38 at MOI of 2. The cells are grown in 28° C. at continuous shaking (90 rpm). At 60 hours post-infection (hpi), the medium is collected and cells are separated from the medium by centrifugation at 5000 rpm for 5 minutes. 10 mL medium is separated using cation exchange chromatography with a SP-Sepharose column. The column is equilibrated with PBS pH 6.5, and, following loading of the sample on the column, the column is washed with PBS to elute the unbound proteins (flow through fraction). Elution is done with increasing concentration of NaCl at a flow rate of 2 mL/min (5% NaCl/min).

The different fractions are subjected to SDS-PAGE electrophoresis and to western blotting using anti-Hormonal Imbalance variant antibody.

Example 2

Secretion

Sf-9 cells are infected with Hormonal Imbalance variants expressing baculovirus (Ac-hormonal Imbalance variant) at MOI of 2. The cells are grown at 28° C. at continuous shaking (90 rpm), and 1 mL samples are collected at 24, 48, and 60 hours post-infection (hpi). Following centrifugation, cell pellets are lysed with lysis buffer (50 mM Tris pH 7.5, 1% triton X100, and protease inhibitor cocktail) at 4° C. for 30 min and sonicated for 30 seconds. The sample is centrifuged for 10 minutes at 14000 rpm and the supernatant is designated Pellet. 40 μL of the Pellet preparation and of the medium (Designated Medium) are supplemented with sample buffer and are electrophoresed on a 15% SDS-PAGE. Following electrophoresis, the gel is subjected to a semi-dry protein transfer onto a nitrocellulose membrane. The membrane is incubated with anti-Hormonal Imbalance variants antibody for 2 hours and with secondary anti-rabbit antibody for an additional 1 hour.

Detection of the signal is done using a commercial western blot detection kit.

Example 3

Competition Binding Assays

Transfected COS-7 cells are transferred to culture plates one day after transfection at a density of $1\times10^5$ cells per well aiming at 5-8% binding of the radioactive ligand. Two days after transfection, competition binding experiments are performed for 3 hours at 4° C. using 25 pM of [$^{125}$I]hormonal imbalance variant. Binding assays are performed in 0.5 ml of a 50 mM Hepes buffer, pH 7.4, supplemented with 1 mM $CaCl_2$, 5 mM $MgCl_2$, and 0.1% (w/v) bovine serum albumin, 40 μg/ml bacitracin. Non-specific binding is determined as the binding in the presence of 1 micromole of unlabeled hormonal imbalance splice variant. Cells are washed twice in 0.5 ml of ice-cold buffer and 0.5-1 ml of lysis buffer (8 M Urea, 2% NP40 in 3 M acetic acid) is added and the bound radioactivity is counted. Determinations are made in duplicate.

Example 4

Synthetic Production of Hormonal Imbalance Splice Variant-Like Compound

Amino acid derivatives and synthesis reagents, can be obtained from commercial sources. Peptide chain extension can be performed using Applied Biosystem 433A synthesizer produced by Perkin Elmer, and a protected peptide derivative-resin can be constructed by the Boc or Fmoc method. The protected peptide resin obtained by the Boc method is deprotected with anhydrous hydrogen fluoride (HF) in the presence of p-cresol thereby releasing the peptide, which is then purified. The protected peptide resin obtained by the Fmoc method is deprotected with trifluoroacetic acid (TFA) or dilute TFA containing various scavengers, and the released peptide is purified. Purification is performed in reversed phase HPLC on a C4 or C18 column. The purity of the purified product can be confirmed by reverse phase HPLC, and its structure can be confirmed by amino acid composition analysis and mass spectrometry.

Peptides disclosed herein can be produced by a conventional peptide synthesis method. Specifically, synthesis of acylated or alkylated peptides is exemplified below.

Abbreviations: "HMP resin" means 4-hydroxymethyl-phenoxymethyl resin; "Fmoc amide resin" means 4-(2',4'-dimethoxyphenyl-Fmoc-aminomethyl) phenoxyacetamido-ethyl resin; "PAM resin" means phenylacetoamidomethyl resin; "HBTU" means 2-(1H-benzotriazole-1-yl)-1,1,3,3-tetramethyluronium hexafluorophosphate; "TBTU" means 2-(1H-benzotriazole-1-yl)-1,1,3,3-tetramethyluronium tetrafluoroborate; "HOBt" means 1-hydroxybenzotriazole; "DCC" means dicyclohexylcarbodiimide; "DIPCI" means diisopropylcarbodiimide; "TFA" means trifluoroacetic acid; "DIPEA" means diisopropylethylamine; "TIPS" means triisopropylsilane; "Fmoc" means fluorenylmethoxycarbonyl; "Boc" means t-butyloxycarbonyl; "Trt" means trityl; "Bu" means t-butyl; "Pmc" means 2,2,5,7,8-pentamethylchroman-6-sulfonyl; "Prl" means propionyl; "PhPrl" means phenyl-propionyl; "Bzl" means benzyl; "Bom" means benzyloxymethyl; "Tos" means toluenesulfonyl; "Cl-Z" means 2-chlorobenzyloxycarbonyl; "Pis" means 2-phenylisopropyl; "Mtt" means 4-methyltrityl; "DMF" means N,N-dimethylformamide; "NMP" means N-methylpyrrolidone; "DMAP" means 4-dimethylaminopyridine; "HOSu" means N-hydroxysuccinimide; "Adod" means 2-aminododecanoic acid; "Aib" means 2-aminoisobutylic acid; "Ape" means 5-aminopentanoic acid; "Cha" means cyclohexylalanine; "Dap" means 2,3-diaminopropionic acid; "Nal" means naphthylalanine; "Nle" means norleucine.

Protecting amino acids which can be used in synthesis Fmoc method: Boc-Gly, Fmoc-Gly, Fmoc-Ser (Bu), Fmoc-Ser (Trt), Fmoc-Glu (OBu), Fmoc-His (Boc), Fmoc-Gln (Trt), Fmoc-Arg (Pmc), Fmoc-Lys (Boc), Fmoc-Pro, Fmoc-Leu, Fmoc-Ala, Fmoc-Val, Fmoc-Phe, Fmoc-Phe, Fmoc-Ser (n-$C_8H_{17}$), Fmoc-Ser (n-$C_8H_{17}$), Fmoc-Cys (n-$C_8H_{17}$), Fmoc-Asp (OPis), Fmoc-Ser (Bzl), Fmoc-Cys (Trt), Fmoc-Dap (Octanoyl), Fmoc-2-Nal, Fmoc-2-Nal, Fmoc-Nle, Fmoc-Lys (Mtt), Fmoc-Aib-OH, Fmoc-Asp (O—$C_7H_{15}$). Boc method: Boc-Gly, Boc-Ser (Bzl), Boc-Ser (Ac), Boc-Ser (Prl), Boc-Glu (OBzl), Boc-His (Bom), Boc-Gln, Boc-Arg (Tos), Boc-Lys (Cl-Z), Boc-Pro, Boc-Leu, Boc-Ala, Boc-Val, Boc-Phe, Boc-Cys (n-$C_8H_{17}$), Boc-Ape, Boc-Ser (n-$C_8H_{17}$)

Units used:
(a) Analytical HPLC system Unit: Shimadzu LC-10A System; Column: YMC PROTEIN-RP (4.6 mm×150 mm); Column temperature: 40° C.; Eluent: A linear gradient of from 0 to 50% acetonitrile for 20 minutes in 0.1% trifluoroacetic acid; Flow rate: 1 mL/min; Detection: UV (210 nm); Injection volume: 10 to 100 mu l.
(b) Preparative HPLC system Unit: Waters 600 Multisolvent Delivery System; Columns: YMC-Pack-ODS-A (5 mu m, 20 mm×250 mm) YMC-Pack-PROTEIN-RP (5 mu m, C4, 10 mm×250 mm) YMC-Pack PROTEIN-RP (5 mu m, C4, 20 mm×250 mm) YMC PROTEIN-RP (4.6 mm×150 mm); Eluent: A suitable linear gradient of acetonitrile concentration in 0.1% trifluoroacetic acid; Flow rate: 10 mL/min. (for columns of an inner diameter of 20 mm), 3 mL/min. (for the column of an inner diameter of 10 mm), 1 mL/min. (for the column of an inner diameter of 4.6 mm); Detection: 210 nm, 260 nm; Injection: 10 to 2000 mu l (2000 mu l or more was injected via a pump)

(c) Mass spectrometer Unit: Finnigan MAT TSQ700; Ion source: ESI; Detection ion mode: Positive Spray; Voltage: 4.5 kV; Capillary temperature: 250° C.; Mobile phase: A mixture of 0.2% acetic acid and methanol (1:1); Flow rate: 0.2 mL/min; Scan range: m/z 300 to 1,500

(d) Analysis of amino acid sequence Unit: Applied Biosystem 477A, 492 model sequencer manufactured by Perkin Elmer (e) Analysis of amino acid composition Unit: L-8500 model amino acid analyzer manufactured by Hitachi, Co., Ltd.; Sample: Unless otherwise specified, the sample is hydrolyzed with 6 M HCl at 110° C. for 24 hours in a sealed tube.

Other compounds according to the present disclosure can be produced likewise.

Example 5

A Randomized, Single Center, Four-Period Crossover Trial to Investigate the Absolute Bioavailability of Intravenously Administered Hormonal Imbalance Splice Variant and Subcutaneously Administered Hormonal Imbalance Splice Variant at Three Different Single Doses in Healthy Subjects Objectives:
Primary: To investigate the absolute bioavailability of three different doses of Hormonal Imbalance Splice Variant administered as single intravenous and subcutaneous doses.
Secondary:
1) To investigate the dose linearity (dose proportionality) of the ascending doses.
2) To investigate and compare the pharmacodynamic profiles between the treatments.
3) To assess the safety and local tolerability.

Trial Design: A randomized, single center, unbalanced block design, four-period crossover trial to investigate the absolute bioavailability between intravenously administered Hormonal Imbalance Splice Variant and subcutaneously administered Hormonal Imbalance Splice Variant at three different single doses in healthy subjects. Three doses will be used for each way of administration: low, medium and high. To reduce the number of dosings to each individual and hence reduce the length of the trial, each subject will only receive four doses of the total of six doses, i.e. two dose levels administered as intravenous and subcutaneous, respectively. The unbalanced block design will ensure that all three-dose levels will be covered in this way although not all subjects will receive all dose levels. A sufficient washout period will be placed between the individual dosing periods.

Endpoints:
Pharmacokinetics of Hormonal Imbalance Splice Variant: AUCo-t, AUC, Cmax, tmax, t, Cl/f, Vz/f, Cl, Vz, t1/z
MRT Pharmacodynamics: GH: AUC, Cmax and tmax Cardiac output, assessment of hunger, food/energy intake, degree of pleasure related to food intake, body mass, energy expenditure, DEXA.

Safety: Safety and local tolerability will be assessed throughout the study by clinical evaluations (physical examination and vital signs), electrocardiography and laboratory tests (hematology and clinical chemistry).

Trial population and power calculation: Healthy male subjects, aged 18-45 years with a body mass index (BMI) of 19-26 kg/m$^2$ (both inclusive).

The primary objective of this study is to investigate the absolute bioavailability of Hormonal Imbalance Splice Variant administered as intravenous and subcutaneous. An unbalanced block design will be applied to reduce the trial period time and reduce the number of dosings per subject. The number of subjects needed to perform a statistical analysis of absolute bioavailability per dose levels as well as an analysis of dose linearity between doses will be calculated based on existing literature data.

Trial products: Hormonal Imbalance Splice Variant for intravenous and subcutaneous administration.

Example 6

Functional Tests on the Hormonal Imbalance Splice Variant Receptor

Transfections and tissue culture-COS-7 cells are grown in Dulbecco's modified Eagle's medium 1885 supplemented with 10% fetal calf serum, 2 mM glutamine and 0.01 mg/ml gentamicin. Cells are transfected using calcium phosphate precipitation method with chloroquine addition as previously described (Holst B. et al., Mol. Pharmacol. 53:166-175 (1998)). For gene dose experiments, variable amounts of DNA are used. The amount of cDNA (20 μg/75 cm$^2$) resulting in maximal signaling is used for dose response curves. HEK-293 cells are grown in D-MEM, Dulbecco's modified Eagle's medium 31966 with high glucose supplemented with 10% fetal calf serum, 2 mM glutamine and 0.01 mg/ml gentamicin. Cells are transfected with Lipofectamine® 2000 (Invitrogen Corp., Carlsbad, Calif.).

Phosphatidylinositol turnover: One day after transfection, COS-7 cells are incubated for 24 hours with 5 μCi of [3H]-myo-inositol (GE Healthcare, Piscataway, N.J.) in 1 ml medium supplemented with 10% fetal calf serum, 2 mM glutamine and 0.01 mg/ml gentamicin per well. Cells are washed twice in buffer, 20 mM HEPES, pH 7.4, supplemented with 140 mM NaCl, 5 mM KCl, 1 mM MgSO$_4$, 1 mM CaCl$_2$, 10 mM glucose, 0.05% (w/v) bovine serum; and are incubated in 0.5 ml buffer supplemented with 10 mM LiCl at 37° C. for 30 min. After stimulation with various concentrations of peptide for 45 min at 37° C., cells are extracted with 10% ice-cold perchloric acid followed by incubation on ice for 30 min. The resulting supernatants are neutralized with KOH in HEPES buffer, and the generated [3H]-inositol phosphate is purified on Bio-Rad AG 1-X8 anion-exchange resin (Bio-Rad Laboratories, Hercules, Calif.) as per manufacturer's instructions. Determinations are made in duplicates.

CRE, SRE and NF-κ-B reporter assay: HEK293 cells (30,000 cells/well) seeded in 96-well plates are transiently transfected. In case of the CRE reporter assay, the cells are transfected with a mixture of pFA2-CREB and pFR-Luc reporter plasmid (PathDetect CREB trans-Reporting System, Stratagene, La Jolla, Calif.) or SRE-Luc (PathDetect SRE Cis-Reporting System, Stratagene, La Jolla, Calif.) and the indicated amounts of receptor DNA. Following transfection, cells are maintained in low serum (2.5%) throughout the experiments and are treated with the respective inhibitor of intracellular signaling pathways. One day after transfection, cells are treated with the respective ligands in an assay volume of 100 µl medium for 5 hrs. The assay is terminated by washing the cells twice with PBS and addition of 100 µl Luciferase® assay reagent (LucLite®, PerkinElmer, Inc., Wellesley, Mass.). Luminescence is measured in a TopCounter (Top Count NETT, Packard Instrument Co., Meriden, Conn.) for 5 sec. Luminescence values are given as relative light units (RLU).

MAP Kinase assay: COS 7 cells (seeding density 150,000 cells/well) are transfected in the assay plates. Two days after transfection, the indicated concentration of ligand are added to assay medium without any serum and incubated for 10 min at 37° C. The reaction is stopped by removing the medium and two washing steps with ice cold PBS. The cells are lysed in sample buffer and separated on 10% SDS-PAGE according to Laemmli U. K., Nature 227:680-85 (1970). Proteins are transferred onto nitrocellulose and Western blot analysis carried out using a 1:5000 dilution of mouse monoclonal antiphospho-ERK1/2 antibody (Santa Cruz Biotechnology, Inc., Santa Cruz, Calif.). Total ERK protein is determined using a 1:10000 dilution of anti-ERK antibody (Santa Cruz Biotechnology, Inc., Santa Cruz, Calif.). Blots are probed with anti-mouse horseradish peroxidase-conjugated secondary antibodies, visualized using enhanced chemiluminescence reagent (GE Healthcare, Piscataway, N.J.) and quantified by densiometric analysis. ERK1/2 phosphorylation is normalized according to the loading of protein by expressing the data as a ratio of phosphoERK1/2 over total ERK1/2. Results are expressed as percentage of the value obtained in non-stimulated mock transfected cells.

Example 7

Efficacy of Subcutaneous Administration of Hormonal Imbalance Splice Variant on Weight Gain, Food Consumption, Hormonal, Hematological and Biochemical Parameters Hormonal Imbalance variant (1 mg/kg) or the Vehicle (1.6% mannitol) are administered once daily for 14 successive days, via the subcutaneous (SC) route, to groups comprising n=10 Sprague Dawley rats. All animals are subjected to terminal bleeding, under $CO_2$ anesthesia, immediately prior to euthanasia. Terminal blood collection is performed serially as per animal number, and not as per group.

Hematology: Blood samples (at least 500 µl) are collected into pre-labeled EDTA coated tubes. The tubes are pre-labeled and contain the following information: Study number, group number, animal number and date. The samples are kept until delivery and analysis at 2-8° C. Hematology parameters that are tested using Sysmex K×21 are: WBC, RBC, HGB, HCT, MCV, MCH, MCHC, Platelets. Differential count is preformed manually.

Biochemistry: Blood for biochemistry analysis is collected into non-coated pre-labeled tubes. The tubes are pre-labeled and contained the following information: Study number, group number, animal number and date. Following clotting, the blood from each animal is centrifuged, and the serum is collected into two pre-labeled tubes and submitted for analysis as follows: Serum, 250 µl, was kept at 2-8° C. until analysis. The samples are subjected to the following listed tests using Hitachi 917 system: Creatinine, Total bilirubin, Glucose, Triglycerides, Cholesterol, HDL, LDL, Total protein, Globulin, Albumin, Urea, Potassium, Phosphorus, Calcium, Sodium, Chloride, sGOT, sGPT, ALP, Insulin, IGF.

Urinalysis: Urine is collected into pre-labeled tubes (as above) from all animals (where possible) prior and/or after euthanasia. For all surviving animals, urine collection is performed serially as per animal number, and not as per group. Urinalysis is performed using a commercial test stick (Bayer, Multistix® 10SG) applied to urine sample and evaluating the following parameters: glucose, ketone, pH value, leukocytes, blood, density, nitrite, bilirubin, urobilinogen and protein.

Necropsy Procedures and Macroscopic Examination: All animals are subjected to a full detailed necropsy. For all surviving animals, necropsy is performed serially as per animal number, and not as per group, immediately following the scheduled terminal bleeding. At necropsy, a thorough examination is made and any abnormality or gross pathological changes in tissues and/or organs are observed and recorded.

Organ/Tissue Collection: The organs and tissues listed (Brain, Liver, Kidney, Stomach, Pancreas, Lungs, Spleen, Heart, Epididymal WAT, Retroperitoneal WAT, Interscapular BAT) are excised and weighed wet as soon as possible after excision and removal of the attached fat and other connective tissues. All organs from one animal were collected into one container, pre-labeled with the following information: Study number, group number, animal number and date.

Route of administration, dose, specific strain and species of animal tested and set of parameters to be checked could vary depending on the relevant literature available for each of the hormonal imbalance splice variants.

Example 8

Hormonal Imbalance Splice Variant Hapten Immunoconjugate Synthesis

Hormonal Imbalance Splice variant peptide is synthesized and coupled to the carrier protein KLH, yielding immunoconjugates Hormonal Imbalance Splice variant –KLH. For peptide synthesis, all haptens and substrates are prepared on a 1.0-mmol scale as C-terminal amides by using customwritten DIC_HOBt protocols for Fmoc_tBu SPPS on a CS Bio 136 automated peptide synthesizer. For experimental details, see Example 4.

Subjects. Mature male Wistar rats (n=15) (Charles River, Hollister, Calif.) are individually housed in a 12 h:12 h lit (0600 h lights on), humidity-controlled (60%), and temperature controlled (22° C.) vivarium with continuous access to chow and water. The pelleted chow diet (LM-485 Diet 7012; Harlan Teklad, Madison, Wis.) is a corn-based, extruded cereal composed of 65% carbohydrate, 13% fat, 21% protein, and metabolizable energy of 3.41 kcal/g.

Active Immunization. Age- and weight-matched mature rats are immunized by using protocols involving five immunizations over 12 weeks. Age- and weight-matched rats receive immunizations (i.p. 0.4 ml) 90 min before the dark cycle on experimental days 0, 21, 35, 56, and 84. The first three immunizations consist of Ribi MPL-TDM emulsion adjuvant (Ribi Immunochemical Research Inc.) containing 250 pg of Hormonal Imbalance Splice variant-KLH or KLH in 100 mM PBS at pH 7.4. Tail blood is collected 1 week postimmunization, centrifuged, and plasma analyzed for antibody titers and Hormonal Imbalance Splice Variant binding affinity.

What is claimed is:

1. An isolated polypeptide comprising the sequence set forth in SEQ ID NO: 21.

2. The isolated polypeptide of claim 1, wherein the isolated polypeptide consists of SEQ ID NO:21.

* * * * *

SEQUENCE LISTING

<160> NUMBER OF SEQ ID NOS: 38

<210> SEQ ID NO 1
<211> LENGTH: 1128
<212> TYPE: DNA
<213> ORGANISM: Homo sapiens

<400> SEQUENCE: 1

| | | | | | |
|---|---|---|---|---|---|
| acagagctta | ggacacagag | cacatcaaaa | gttcccaaag | agggcttgct | ctctcttcac | 60 |
| ctgctctgtt | ctacagcaca | ctaccagaag | acagcagaaa | tgaaaagcat | ttactttgtg | 120 |
| gctggattat | ttgtaatgct | ggtacaaggc | agctggcaac | gttcccttca | agacacagag | 180 |
| gagaaatcca | gatcattctc | agcttcccag | gcagacccac | tcagtgatcc | tgatcagatg | 240 |
| aacgaggaca | agcgccattc | acagggcaca | ttcaccagtg | actacagcaa | gtatctggac | 300 |
| tccaggcgtg | cccaagattt | tgtgcagtgg | ttgatgaata | ccaagaggaa | caggaataac | 360 |
| attgccaaac | gtcacgatga | atttgagaga | catgctgaag | gacctttac | cagtgatgta | 420 |
| agttcttatt | tggaaggcca | agctgccaag | gaattcattg | cttggctggt | gaaaggccga | 480 |
| ggaaggcgag | atttcccaga | agaggtcgcc | attgttgaag | aacttggccg | cagacatgct | 540 |
| gatggttctt | tctctgatga | gatgaacacc | attcttgata | tcttgccgc | cagggacttt | 600 |
| ataaactggt | tgattcagac | caaaatcact | gacaggaaat | aactatatca | ctattcaaga | 660 |
| tcatcttcac | aacatcacct | gctagccacg | tgggatgttt | gaaatgttaa | gtcctgtaaa | 720 |
| tttaagaggt | gtattctgag | gccacattgc | tttgcatgcc | aataaataaa | ttttctttta | 780 |
| gtgttgtgta | gccaaaaatt | acaaatggaa | taaagtttta | tcaaaatatt | gctaaaatat | 840 |
| cagcttttaaa | atatgaaagt | gctagattct | gttattttct | tcttattttg | gatgaagtac | 900 |
| cccaacctgt | ttacatttag | cgataaaatt | atttttctat | gatataattt | gtaaatgtaa | 960 |
| attattccga | tctgacatat | ctgcattata | ataataggag | aatagaagaa | ctggtagcca | 1020 |
| cagtggtgaa | attggaaaga | gaactttctt | cctgaaacct | ttgtcttaaa | aatactcagc | 1080 |
| tttcaatgta | tcaaagatac | aattaaataa | aattttcaag | cttcttta | | 1128 |

<210> SEQ ID NO 2
<211> LENGTH: 1048
<212> TYPE: DNA
<213> ORGANISM: Homo sapiens

<400> SEQUENCE: 2

| | | | | | |
|---|---|---|---|---|---|
| acagagctta | ggacacagag | cacatcaaaa | gttcccaaag | agggcttgct | ctctcttcac | 60 |
| ctgctctgtt | ctacagcaca | ctaccagaag | acagcagaaa | tgaaaagcat | ttactttgtg | 120 |
| gctggattat | ttgtaatgct | ggtacaaggc | agctggcaac | gttcccttca | agacacagag | 180 |
| gagaaatcca | gatcattctc | agcttcccag | gcagacccac | tcagtgatcc | tgatcagatg | 240 |
| aacgaggaca | agcgccattc | acagggcaca | ttcaccagtg | actacagcaa | gtatctggac | 300 |
| tccaggcgtg | cccaagattt | tgtgcagtgg | ttgatgaata | ccaagaggaa | caggaataac | 360 |
| attgccaaac | gtcacgatga | atttgagaga | catgctgaag | gacctttac | cagtgtttcc | 420 |
| cagaagaggt | cgccattgtt | gaagaacttg | gccgcagaca | tgctgatggt | tctttctctg | 480 |
| atgagatgaa | caccattctt | gataatcttg | ccgccaggga | ctttataaac | tggttgattc | 540 |
| agaccaaaat | cactgacagg | aaataactat | atcactattc | aagatcatct | tcacaacatc | 600 |
| acctgctagc | cacgtgggat | gtttgaaatg | ttaagtcctg | taaatttaag | aggtgtattc | 660 |

```
tgaggccaca ttgctttgca tgccaataaa taaattttct tttagtgttg tgtagccaaa    720
aattacaaat ggaataaagt tttatcaaaa tattgctaaa atatcagctt taaaatatga    780
aagtgctaga ttctgttatt ttcttcttat tttggatgaa gtaccccaac ctgtttacat    840
ttagcgataa aattattttt ctatgatata atttgtaaat gtaaattatt ccgatctgac    900
atatctgcat tataataata ggagaataga agaactggta gccacagtgg tgaaattgga    960
aagagaactt tcttcctgaa acctttgtct taaaaatact cagcttttcaa tgtatcaaag   1020 atacaattaa ataaaatttt caagcttc                                      1048

<210> SEQ ID NO 3
<211> LENGTH: 1241
<212> TYPE: DNA
<213> ORGANISM: Homo sapiens

<400> SEQUENCE: 3
agttcactca ctttcaaagc cagctgaagg aaagaggaag tgctagagag agccccttc     60 agtgtgcttc tgacttttac ggacttggct tgttagaagg ctgaaagatg atggcaggaa   120
tgaaaatcca gcttgtatgc atgctactcc tggctttcag ctcctggagt ctgtgctcag   180
attcagaaga ggaaatgaaa gcattagaag cagatttctt gaccaatatg catacatcaa   240
agattagtaa agcacatgtt ccctcttgga agatgactct gctaaatgtt tgcagtcttg   300
taaataattt gaacagccca gctgaggaaa caggagaagt tcatgaagag agcttgttg    360 caagaaggaa acttcctact gctttagatg gctttagctt ggaagcaatg ttgacaatat   420
accagctcca caaaatctgt cacagcaggg ctttttcaaca ctgggagtta atccaggaag   480
atattcttga tactggaaat gacaaaaatg gaaaggaaga agtcataaag agaaaaattc    540
cttatattct gaaacggcag ctgtatgaga ataaacccag aagacctac atactcaaaa    600 gagattctta ctattactga gagaataaat catttattta catgtgattg tgattcatca    660 tccccttaatt aaatatcaaa ttatatttgt gtgaaaatgt gacaaacaca cttatctgtc   720
tcttctacaa ttgtggttta ttgaatgtga ttttttctgca ctaatataaa ttagactaag   780
tgttttcaaa taaatctaaa tcttcagcat gatgtgttgt gtataattgg agtagatatt    840
aattaagtca cctgtataat gttttgtaat tttgcaaaac atatcttgag ttgtttaaac    900
agtcaaaatg tttgatattt tataccagct tatgagctca aagtactaca gcaaagccta    960
gcctgcatat cattcaccca aaacaaagta atagcgcctc ttttattatt ttgactgaat   1020
gttttatgga attgaaagaa acatacgttc ttttcaagac ttcctcatga atctctcaat   1080
tataggaaaa gttattgtga taaaatagga acagctgaaa gattgattaa tgaactattg   1140
ttaattcttc ctattttaat gaatgacatt gaactgaatt ttttgtctgt taaatgaact   1200
tgatagctaa taaaaagaca actagccatc aaaaaaaaaa a                       1241

<210> SEQ ID NO 4
<211> LENGTH: 641
<212> TYPE: DNA
<213> ORGANISM: Homo sapiens

<400> SEQUENCE: 4
atagttcact cactttcaaa gccagctgaa ggaaagagga agtgctagag agagccccct    60
tcagtgtgct tctgactttt acggacttgg cttgttagaa ggctgaaaga tgatggcagg   120
aatgaaaatc cagcttgtat gcatgctact cctggctttc agctcctgga gtctgtgctc   180
```

| | | | | |
|---|---|---|---|---|
| agattcagaa | gaggaaatga | aagcattaga | agcagatttc | ttgaccaata tgcatacatc | 240 |
| aaagattagt | aaagcacatg | ttccctcttg | gaagatgact | ctgctaaatg tttgcagtct | 300 |
| tgtaaataat | ttgaacagcc | cagctgagga | acaggagaa | gttcatgaag aggagcttgt | 360 |
| tgcaagaagg | aaacttccta | ctgctttaga | tggctttagc | ttggaagcaa tgttgacaat | 420 |
| ataccagctc | cacaaaatct | gtcacagcag | ggcttttcaa | cactgggagt taatccagga | 480 |
| ggatattctt | gatactggaa | atgacaaaaa | tggaaaggaa | gaagtcataa agagaaaaat | 540 |
| tccttatatt | ctgaaacggc | agcaggccac | atgtgctcga | gctgtatgag aataaaccca | 600 |
| gaagacccta | catactcaaa | agagattctt | actattactg | a | 641 |

<210> SEQ ID NO 5
<211> LENGTH: 1018
<212> TYPE: DNA
<213> ORGANISM: Homo sapiens

<400> SEQUENCE: 5

| | | | | |
|---|---|---|---|---|
| gatagttcac | tcactttcaa | agccagctga | aggaaagagg | aagtgctaga gagagccccc | 60 |
| ttcagtgtgc | ttctgacttt | tacggacttg | gcttgttaga | aggctgaaag atgatggcag | 120 |
| gaatgaaaat | ccagcttgta | tgcatgctac | tcctggcttt | cagctcctgg agtctgtgct | 180 |
| cagattcaga | agaggaaatg | aaagcattag | aagcagattc | ttgaccaat atgcatacat | 240 |
| caaagttaat | ccaggaagat | attcttgata | ctggaaatga | caaaaatgga aggaagaag | 300 |
| tcataaagag | aaaaattcct | tatattctga | acggcagct | gtatgagaat aaacccagaa | 360 |
| gaccctacat | actcaaaaga | gattcttact | attactgaga | gaataaatca tttatttaca | 420 |
| tgtgattgtg | attcatcatc | ccttaattaa | atatcaaatt | atatttgtgt gaaaatgtga | 480 |
| caaacacact | tatctgtctc | ttctacaatt | gtggtttatt | gaatgtgatt tttctgcact | 540 |
| aatataaatt | agactaagtg | ttttcaaata | aatctaaatc | ttcagcatga tgtgttgtgt | 600 |
| ataattggag | tagatattaa | ttaagtcacc | tgtataatgt | tttgtaattt tgcaaaacat | 660 |
| atcttgagtt | gtttaaacag | tcaaaatgtt | tgatatttta | taccagctta tgagctcaaa | 720 |
| gtactacagc | aaagcctagc | ctgcatatca | ttcacccaaa | acaaagtaat agcgcctctt | 780 |
| ttattatttt | gactgaatgt | tttatggaat | tgaaagaaac | atacgttctt ttcaagactt | 840 |
| cctcatgaat | ctctcaatta | taggaaaagt | tattgtgata | aaataggaac agctgaaaga | 900 |
| ttgattaatg | aactattgtt | aattcttcct | attttaatga | atgacattga actgaatttt | 960 |
| ttgtctgtta | aatgaacttg | atagctaata | aaaagacaac | tagccatcaa aaaaaaaa | 1018 |

<210> SEQ ID NO 6
<211> LENGTH: 420
<212> TYPE: DNA
<213> ORGANISM: Homo sapiens

<400> SEQUENCE: 6

| | | | | |
|---|---|---|---|---|
| atggctgccg | cacgcctctg | cctctccctg | ctgctcctgt | ccacctgcgt ggctctgtta | 60 |
| ctacagccac | tgctgggtgc | ccagggagcc | ccactggagc | cagtgtaccc aggggacaat | 120 |
| gccacaccag | agcagatggc | ccagtatgca | gctgatctcc | gtagatacat caacatgctg | 180 |
| accaggccta | ggtatgggaa | aagacacaaa | gaggacacgt | ggccttctc ggagtggggg | 240 |
| tccccgcatg | ctgctgtccc | cagggagctc | agcccgctgg | acttataatg ccaccttctg | 300 |
| tctcctacga | ctccatgagc | agcgccagcc | cagctctccc | ctctgcaccc ttggctctgg | 360 |
| ccaaagcttg | ctccctgctc | ccacacaggc | tcaataaagc | aagtcaaagc caaaaaaaaa | 420 |

<210> SEQ ID NO 7
<211> LENGTH: 450
<212> TYPE: DNA
<213> ORGANISM: Homo sapiens

<400> SEQUENCE: 7

| | | | | | |
|---|---|---|---|---|---|
| gatggctgcc | gcacgcctct | gcctctccct | gctgctcctg | tccacctgcg | tggctctgtt | 60 |
| actacagcca | ctgctgggtg | cccagggagc | cccactggag | ccagtgtacc | caggggacaa | 120 |
| tgccacacca | gagcagatgg | cccagtatgc | agctgatctc | cgtagataca | tcaacatgct | 180 |
| gaccaggcct | agtgcttgcc | cctgctgcct | cttccctccc | aggtatggga | aagacacaa | 240 |
| agaggacacg | ctggccttct | cggagtgggg | gtccccgcat | gctgctgtcc | cagggagct | 300 |
| cagcccgctg | gacttataat | gccaccttct | gtctcctacg | actccatgag | cagcgccagc | 360 |
| ccagctctcc | cctctgcacc | cttggctctg | gccaaagctt | gctccctgct | cccacacagg | 420 |
| ctcaataaag | caagtcaaag | ccaaaaaaaa | | | | 450 |

<210> SEQ ID NO 8
<211> LENGTH: 908
<212> TYPE: DNA
<213> ORGANISM: Homo sapiens

<400> SEQUENCE: 8

| | | | | | |
|---|---|---|---|---|---|
| ggttgacccg | ggccctcctc | cacaccccct | tccttcttcg | cctcctccct | ctttcctgca | 60 |
| cgggggctcg | ggctcactat | aaaaggtggg | agcgcgtggt | gccccagcaa | cgacgagttt | 120 |
| cagaacgatg | gagagctccc | gcgtgaggct | gctcccctc | ctgggcgccg | ccctgctgct | 180 |
| gatgctacct | ctgttgggta | cccgtgccca | ggaggacgcc | gagctccagc | ccgagcccct | 240 |
| ggacatctac | tctgccgtgg | atgatgcctc | ccacgagaag | gagctgatcg | aagcgctgca | 300 |
| agaagtcttg | aagaagctca | agagtaaacg | tgttcccatc | tatgagaaga | gtatgccca | 360 |
| agtccccatg | tgtgacgccg | gtgagcagtg | tgcagtgagg | aaaggggcaa | ggatcgggaa | 420 |
| gctgtgtgac | tgtccccgag | gaacctcctg | caattccttc | ctcctgaagt | gcttatgaag | 480 |
| gggcgtccat | tctcctccat | acatccccat | ccctctactt | tccccagagg | accacaccttt | 540 |
| cctcccctgga | gtttgcta | agcaacagat | aaagtttttta | tttttcctctg | aagggaaagg | 600 |
| gctctttttcc | tgctgttca | aaaataaaag | aacacattag | atgttactgt | gtgaagaata | 660 |
| atgccttgta | tggtgttgat | acgtgtgtga | agtattctta | ttttatttgt | ctgacaaact | 720 |
| cttgtgtacc | tttgtgtaaa | gaagggaagc | tttgtttgaa | aattgtatt | ttgtatgtgg | 780 |
| catggcagaa | tgaaaattag | atctagctaa | tctcggtaga | tgtcattaca | acctggaaaa | 840 |
| taaatcaccc | taagtgacac | aaattgaagc | atgtacaaat | tatacataat | aaagtgtttt | 900 |
| taataatt | | | | | | 908 |

<210> SEQ ID NO 9
<211> LENGTH: 1226
<212> TYPE: DNA
<213> ORGANISM: Homo sapiens

<400> SEQUENCE: 9

| | | | | | |
|---|---|---|---|---|---|
| aacgacgagt | ttcagaacga | tggagagctc | ccgcgtgagg | ctgctgcccc | tcctgggcgc | 60 |
| cgccctgctg | ctgatgctac | ctctgttggg | tacccgtgcc | caggaggacg | ccgagctcca | 120 |
| gccccgagcc | ctggacatct | actctgccgt | ggatgatgcc | tcccacgaga | aggagctggt | 180 |

-continued

```
cggtattccc ctcgctctcg acccccttga gctgtcgcct tgtctcttct cttgcacgcc      240
tccctcctcc ccccaccccc actcctattc ccagagtcag ggcgcgggga gctgagcgca      300
acgcccaggc acccactgcc atccgaagag cgtctcgagc tcacgggctc ctggcagtct      360
gttgagcgaa tccctcatcc cggcccctct gagcaacagg gaccccagcg gctcagagac      420
ccgcggtcag tacctgggac agcgtccgct aagtttccac ccctcgacca ttccctgtgt      480
ccgcggagtc ccaccgcaga gtgcgtgtgg gtccggggct ccttataact agggctggaa      540
gtgcgcacct gggctgggct cgcagccaag gcggcaactt caggctccga agcggtgtgt      600
tgcagatcga agcgctgcaa gaagtcttga gaagctcaa gagtaaacgt gttcccatct      660
atgagaagaa gtatggccaa gtccccatgt gtgacgccgg tgagcagtgt gcagtgagga      720
aaggggcaag gatcgggaag ctgtgtgact gtccccgagg aacctcctgc aattccttcc      780
tcctgaagtg cttatgaagg ggcgtccatt ctcctccata catccccatc cctctacttt      840
ccccagagga ccacaccttc ctccctggag tttggcttaa gcaacagata aagttttat       900 tttcctctga agggaagggg ctcttttcct gctgtttcaa aaataaaaga acacattaga      960
tgttactgtg tgaagaataa tgccttgtat ggtgttgata cgtgtgtgaa gtattcttat     1020
tttatttgtc tgacaaactc ttgtgtacct ttgtgtaaag aagggaagct ttgtttgaaa     1080
attgtatttt tgtatgtggc atggcagaat gaaaattaga tctagctaat ctcggtagat     1140
gtcattacaa cctggaaaat aaatcaccct aagtgacaca aattgaagca tgtacaaatt     1200
atacataata aagtgttttt aataat                                          1226
```

<210> SEQ ID NO 10
<211> LENGTH: 615
<212> TYPE: DNA
<213> ORGANISM: Homo sapiens

<400> SEQUENCE: 10

```
agccccggga cagaccctgt gttccccaag gcgtcttcag cctgccccga gggacagaga       60
ctggagctca atcttggacc gtacagacgc tcgccgacaa cctggccggc ggcaccatga      120
ggcaggcggg acgcgcagcg ctgctggccg cgctgctgct cctggtacag ctgtgccctg      180
ggagcagcca aggagccccc gaggcggccg gggtccagga cccgagtctg cgctggagcc      240
ccggggcacg gaaccagggt ggcggggccc gcgcgctcct cttgctgctg gcggagcgct      300
tcccgcgccg cgcggggccc ggccgattgg gactcgggac ggcaggcgag cggccgcggc      360
gggacaaccc ttctctgtcc attgacctca cctttcacct gctgcggacc ctgctggagc      420
tggcgcggac gcagagccag cgggagcgcg ccgagcagaa ccgcatcata ttcgactcgg      480
tgggcaagtg atggcccggt ttggggctgc gaaaacgttg accccttcc cccacccag       540 agttgggatg cggggcagag ccaccagggc actgtctgcg tgactatttt ttaataaaag      600
tactgaagac ccgtt                                                       615
```

<210> SEQ ID NO 11
<211> LENGTH: 775
<212> TYPE: DNA
<213> ORGANISM: Homo sapiens

<400> SEQUENCE: 11

```
tgcgtccagt gctgcttcca gcgctagccc caggggcacg aaggctggtg tagggaggtg       60
cgcccctccg ggggcccgcc agccgtcaga ctcgaagctg tggctgtcat tgcttctaca      120
atcagtgcat gttcttcgct gacgtcagtc ggagctgtcc tggcactata taaggctggc      180
```

| | | | |
|---|---|---|---|
| gacagcccg | ggacagaccc | tgtgttcccc | aaggcgtctt | cagcctgccc | cgagggacag | 240 |
| agactggagc | tcaatcttgg | accgtacaga | cgctcgccga | caacctggcc | ggcggcacca | 300 |
| tgaggcaggc | gggacgcgca | gcgctgctgg | ccgcgctgct | gctcctggta | cagctgtgcc | 360 |
| ctgggagcag | ccagaggagc | cccgagtctg | cgctggagcc | ccggggcacg | gaaccagggt | 420 |
| ggcgggggccc | gcgcgctcct | cttgctgctg | cggagcgct | tcccgcgccg | cgcggggccc | 480 |
| ggccgattgg | gactcgggac | ggcaggcgag | cggccgcggc | gggacaaccc | ttctctgtcc | 540 |
| attgacctca | cctttcacct | gctgcggacc | ctgctggagc | tggcgcggac | gcagagccag | 600 |
| cgggagcgcg | ccgagcagaa | ccgcatcata | ttcgactcgg | tgggcaagtg | atggcccggt | 660 |
| ttggggctgc | gaaaacgttg | accccttttcc | cccaccccag | agttgggatg | cggggcagag | 720 |
| ccaccagggc | actgtctgcg | tgactatttt | ttaataaaag | tactgaagac | ccgtt | 775 |

<210> SEQ ID NO 12
<211> LENGTH: 1239
<212> TYPE: DNA
<213> ORGANISM: Homo sapiens

<400> SEQUENCE: 12

| | | | |
|---|---|---|---|
| cggcgagggt | cctgccgagg | gacccgttct | gcgcccaggc | aggctcgaag | cacgcgtccc | 60 |
| tctctcctcg | cagtccatgg | cgcggttcct | gacactttgc | acttggctgc | tgttgctcgg | 120 |
| ccccgggctc | ctggcgaccg | tgcgggccga | atgcagccag | gattgcgcga | cgtgcagcta | 180 |
| ccgcctagtg | cgcccggccg | acatcaactt | cctggcttgc | gtaatggaat | gtgaaggtaa | 240 |
| actgccttct | ctgaaaattt | gggaaacctg | caaggagctc | ctgcagctgt | ccaaaccaga | 300 |
| gcttcctcaa | gatggcacca | gcaccctcag | agaaaatagc | aaaccggaag | aaagccattt | 360 |
| gctagccaaa | aggtatgggg | gcttcatgaa | aaggtatgga | ggcttcatga | agaaaatgga | 420 |
| tgagctttat | cccatggagc | cagaagaaga | ggccaatgga | agtgagatcc | tcgccaagcg | 480 |
| gtatgggggc | ttcatgaaga | aggatgcaga | ggaggacgac | tcgctggcca | attcctcaga | 540 |
| cctgctaaaa | gagcttctgg | aaacagggga | caaccgagag | cgtagccacc | accaggatgg | 600 |
| cagtgataat | gaggaagaag | tgagcaagag | atatgggggc | ttcatgagag | gcttaaagag | 660 |
| aagcccccaa | ctggaagatg | aagccaaaga | gctgcagaag | cgatatgggg | gcttcatgag | 720 |
| aagagtaggt | cgcccagagt | ggtggatgga | ctaccagaaa | cggtatggag | gtttcctgaa | 780 |
| gcgctttgcc | gaggctctgc | cctccgacga | agaaggcgaa | agttactcca | agaagttcc | 840 |
| tgaaatggaa | aaagatacg | gaggatttat | gagattttaa | tattttcccc | actagtggcc | 900 |
| ccaggcccca | gcaagcctcc | ctccatcctc | cagtgggaaa | ctgttgatgg | tgttttattg | 960 |
| tcatgtgttg | cttgccttgt | atagttgact | tcattgtctg | gataactata | caacctgaaa | 1020 |
| actgtcattt | caggttctgt | gctcttttg | gagtctttaa | gctcagtatt | agtctattgc | 1080 |
| agctatctcg | ttttcatgct | aaaatagttt | ttgttatctt | gtctcttatt | tttgacaaac | 1140 |
| atcaataaat | gcttacttgt | atatagagat | aataaaccta | ttaccccaag | tgcaaaaaaa | 1200 |
| aaaaaaaaaa | aaaaaaaaa | aaaaaaaaa | aaaaaaaa | | | 1239 |

<210> SEQ ID NO 13
<211> LENGTH: 1055
<212> TYPE: DNA
<213> ORGANISM: Homo sapiens

<400> SEQUENCE: 13

-continued

| | |
|---|---|
| cactgactga agtcctgccc tggctcttag cttcggggat ccgcgactat ctggggaccg | 60 |
| gcttgcgtaa tggaatgtga aggtaaactg ccttctctga aaatttggga aacctgcaag | 120 |
| gagctcctgc agctgtccaa accagagctt cctcaagatg gcaccagcac cctcagagaa | 180 |
| aatagcaaac cggaagaaag ccatttgcta gccaaaaggt atgggggctt catgaaaagg | 240 |
| tatggaggct tcatgaagaa aatggatgag ctttatccca tggagccaga agaagaggcc | 300 |
| aatggaagtg agatcctcgc caagcggtat gggggcttca tgaagaagga tgcagaggag | 360 |
| gacgactcgc tggccaattc ctcagacctg ctaaaagagc ttctggaaac aggggacaac | 420 |
| cgagagcgta gccaccacca ggatggcagt gataatgagg aagaagtgag caagagatat | 480 |
| gggggcttca tgagaggctt aaagagaagc ccccaactgg aagatgaagc caaagagctg | 540 |
| cagaagcgat atgggggctt catgagaaga gtaggtcgcc cagagtggtg gatggactac | 600 |
| cagaaacggt atggaggttt cctgaagcgc tttgccgagg ctctgccctc cgacgaagaa | 660 |
| ggcgaaagtt actccaaaga agttcctgaa atggaaaaaa gatacggagg atttatgaga | 720 |
| ttttaatatt tttcccacta gtggcccag gccccagcaa gcctccctcc atcctccagt | 780 |
| gggaaactgt tgatggtgtt ttattgtcat gtgttgcttg ccttgtatag ttgacttcat | 840 |
| tgtctggata actatacaac ctgaaaactg tcatttcagg ttctgtgctc ttttggagt | 900 |
| ctttaagctc agtattagtc tattgcagct atctcgtttt catgctaaaa tagttttgt | 960 |
| tatcttgtct cttattttg acaaacatca ataaatgctt acttgtatat agagataata | 1020 |
| aacctattac cccaagtgca taaaaaaact tgtaa | 1055 |

<210> SEQ ID NO 14
<211> LENGTH: 5361
<212> TYPE: DNA
<213> ORGANISM: Homo sapiens

<400> SEQUENCE: 14

| | |
|---|---|
| tttctccttc cctccacggg ccgggtgaga aagtagccgg gggctatccc gacccggcgg | 60 |
| ttcttgggga gggggccgaa caagaaaagg gaggagatgg agataacttc cccggattta | 120 |
| gcttttttgt ctttgttttt gttctcacca cttccatcgg atgactggag agtaaaaggg | 180 |
| aacccggagc ggggtggcga gcagcgcttt gagaaaatgc aggagtgtgt ttggagacgc | 240 |
| gtaaagttgc cttttcaagct ctggcctccg ggcacgcgat gctccgcggc gggctgactc | 300 |
| agggctgcct tgggcctccc tgccaccctc ctggaaatga tgcaagtcct gactgtcacc | 360 |
| tggatccctg cagcccagcc tggaatgcgt ctggattagg ggaaagacga gaaacgacac | 420 |
| tccaggtgtt gcacggccca ccaaagcggg aagatagggc agttgctcag accaaatact | 480 |
| gtatctagtg cttctgctcc tatcttcaat cgtgggggttc ttttttaatgc aaagtgtcac | 540 |
| aaggccagga attcccatgt gtgctcagtt ggcccacagc atcattgtgc ctaggaaact | 600 |
| gcttcaattt atcaagtcct ctgggctggg aatctcactg aattccaaac ggcggaaaga | 660 |
| ggaaactttc caacccgat gtgggtgtga cgcgagccag ggcccccagg gacactgtcc | 720 |
| cagagcacac cgtcccccctt taacagcaac tggagcttgg attcgctctt atattgtaca | 780 |
| gtcctttcga ccattgccct ggagcacccg cacacgcgca cgcatctccg gccgcgctca | 840 |
| cacacactca tacacacgca cgcaaacgcg tggccgccgc caggtcggca actttgtccg | 900 |
| gcgctcccag cggcgctcgg cttcctcctg tagtagttga gcgcaggccc cgcctcccgg | 960 |
| ccgtgttgtc aaaagggccg gggtctcgga ttggtccagc cgccgggaca acacctgctc | 1020 |
| gactccttca ttcaagtgac accagagctt ccagggatat ttgaggcacc atccctgcca | 1080 |

```
ttgccgggca ctcgcggcgc tgctaacggc ctggtcacat gctctccgga gagctacggg    1140
agggcgctgg gtaacctcta tccgagccgc ggccgcgagg aggagggaaa aggcgagcaa    1200
aaaggaagag tgggaggagg aggggaagcg gcgaaggagg aagaggagga ggaggaagag    1260
gggagcacaa aggatccagg tctcccgacg ggaggttaat accaagaacc atgtgtgccg    1320
agcggctggg ccagttcatg accctggctt tggtgttggc cacctttgac ccggcgcggg    1380
ggaccgacgc caccaaccca cccgagggtc cccaagacag gagctcccag cagaaaggcc    1440
gcctgtccct gcagaataca gcggagatcc agcactgttt ggtcaacgct ggcgatgtgg    1500
ggtgtggcgt gtttgaatgt tcgagaaca actcttgtga gattcggggc ttacatggga    1560
tttgcatgac ttttctgcac aacgctggaa aatttgatgc ccagggcaag tcattcatca    1620
aagacgcctt gaaatgtaag gcccacgctc tgcggcacag gttcggctgc ataagccgga    1680
agtgcccggc catcagggaa atggtgtccc agttgcagcg ggaatgctac ctcaagcacg    1740
acctgtgcgc ggctgcccag gagaacaccc gggtgatagt ggagatgatc catttcaagg    1800
acttgctgct gcacgaaccc tacgtggacc tcgtgaactt gctgctgacc tgtggggagg    1860
aggtgaagga ggccatcacc cacagcgtgc aggttcagtg tgagcagaac tggggaagcc    1920
tgtgctccat cttgagcttc tgcacctcgg ccatccagaa gcctcccacg gcgcccccg     1980 agcgccagcc ccaggtggac agaaccaagc tctccagggc ccaccacggg gaagcaggac    2040
atcacctccc agagcccagc agtagggaga ctggccgagg tgccaagggt gagcgaggta    2100
gcaagagcca cccaaacgcc catgcccgag gcagagtcgg gggccttggg gctcagggac    2160
cttccggaag cagcgagtgg gaagacgaac agtctgagta ttctgatatc cggaggtgaa    2220
atgaaaggcc tggccacgaa atctttcctc cacgccgtcc attttcttat ctatggacat    2280
tccaaaacat ttaccattag agagggggga tgtcacacgc aggattctgt ggggactgtg    2340
gacttcatcg aggtgtgtgt tcgcggaacg gacaggtgag atggagaccc ctggggccgt    2400
ggggtctcag gggtgcctgg tgaattctgc acttacacgt actcaaggga gcgcgcccgc    2460
gttatcctcg tacctttgtc ttctttccat ctgtggagtc agtgggtgtc ggccgctctg    2520 ttgtgggggga ggtgaaccag ggaggggcag ggcaaggcag gcccccaga gctgggccac     2580 acagtgggtg ctgggcctcg ccccgaagct tctggtgcag cagcctctgg tgctgtctcc    2640
gcggaagtca gggcggctgg attccaggac aggagtgaat gtaaaaataa atatcgctta    2700
gaatgcagga gaagggtgga gaggaggcag gggccgaggg ggtgcttggt gccaaactga    2760
aattcagttt cttgtgtggg gccttgcggt tcagagctct tggcgagggt ggagggagga    2820
gtgtcatttc tatgtgtaat ttctgagcca ttgtactgtc tgggctgggg gggacactgt    2880
ccaagggagt ggcccctatg agtttatatt ttaaccactg cttcaaatct cgatttcact    2940
ttttttattt atccagttat atctacatat ctgtcatcta ataaatggc tttcaaacaa      3000 agcaactggg tcattaaaac cagctcaaag ggggtttaaa aaaaaaaac cagcccatcc      3060 tttgaggctg attttctttt tttttaagtt ctattttaaa agctatcaaa cagcgacata    3120
gccatacatc tgactgcctg acatggactc ctgcccactt gggggaaacc ttatacccag    3180
aggaaaatac acacctgggg agtacatttg acaaatttcc cttaggattt cgttatctca    3240 ccttgacccct cagccaagat tggtaaagct gcgtcctggc gattccagga gacccagctg   3300
gaaacctggc ttctccatgt gagggatgg gaaaggaaag aagagaatga agactactta    3360
gtaattccca tcaggaaatg ctgacctttt acataaaatc aaggagactg ctgaaaatct    3420
```

-continued

```
ctaagggaca ggattttcca gatcctaatt ggaaatttag caataaggag aggagtccaa    3480
ggggacaaat aaaggcagag agaagagaca gaactaaaaa tacgaggaaa ggagagtgag    3540
gattttcatt aaaagtctca gcagtggggtt tcttgggtta tttaaaacat cacctaaata   3600
ggccttttct tcctaattgg ccatcaaatt aaagcctatc ctttctcaag caggagctgg    3660
tattgtaggg agtggccggg tattctgggc tgggctcttc tggagtaggg ggtcagcaaa    3720
cattgtctgc aaagggccag atactgaatc cagtactttc agtttggcga gccgtgaggt    3780
ctctgtcgaa actactcaac tctgccgtcc tagcacaaaa gcagccatag acaacacaca    3840
aacgagaggg cttggctccc ttccaggaag atttatttaa caggctccca gctgaatttc    3900
actcacagga cacagtttac tgatctctgt tctagtgagt gggtcaaaaa gcatatgcat    3960
ccttatccgt caactcatca gctcttcctc aaggcaacct gaggcagac accaagaaac     4020 caagcgtatc tgctctaaaa tgacttgttc ctggggaatg ccttcaacca aaacacagct    4080
agtatttcta tgccccaaat ccaatcccag tcttttcatga tccatgccgg cggttgggtg   4140
gggaggggaa tcattggttg ggggaaggga ggaaacccca cctccagccc ccgccaccgg    4200
gctccctggg cacccagcaa gatctggggc tgcagagaac agaagagctg gtgcacttaa    4260
tccagctctg cccttggggg gaggaggacc tgtgtgtcag gctctgccat gggaacgagt    4320
gtaaaccgtg gctgtctcct gcagtgagcc accgcggcag gcacgttgac tgttttactg    4380
acatcactca aaagctaaag caataacatt ctcctgcgtt gctgagtcag ctgttcattt    4440
gtccgccagc tcctggactg gatgtgtgaa aggcatcaca tttccatttt cctccgtgta    4500
aatgttttat gtgttcgcct actgatccca ttcgttgctt ctattgtaaa tatttgtcat    4560
ttgtatttat tatctctgtg ttttccccct aaggcataaa atggtttact gtgttcattt    4620
gaacccattt actgatctct gttgtatatt tttcatgcca ctgctttgtt ttctcctcag    4680
aagtcgggta gatagcattt ctatcccatc cctcacgtta ttggaagcat gcaacagtat    4740
ttattgctca gggtcttctg cttaaaactg aggaaggtcc acattcctgc aagcattgat    4800
tgagacattt gcacaatcta aaatgtaagc aaagtagtca ttaaaaatac accctctact    4860
tgggctttat actgcataca aatttactca tgagccttcc tttgaggaag gatgtggatc    4920
tccaaataaa gatttagtgt ttattttgag ctctgcatct taacaagatg atctgaacac    4980
ctctcctttg tatcaataaa tagccctgtt attctgaagt gagaggacca agtatagtaa    5040
aatgctgaca tctaaaacta aataaataga aaacaccagg ccagaactat agtcatactc    5100
acacaaaggg agaaatttaa actcgaacca agcaaaaggc ttcacggaaa tagcatggaa    5160
aaacaatgct tccagtggcc acttcctaag gaggaacaac cccgtctgat ctcagaattg    5220
gcaccacgtg agcttgctaa gtgataatat ctgtttctac tacggattta ggcaacagga    5280
cctgtacatt gtcacattgc attattttc ttcaagcgtt aataaaagtt ttaaataaat    5340
ggcaaaaaaa aaaaaaaaa a                                               5361
```

<210> SEQ ID NO 15
<211> LENGTH: 1073
<212> TYPE: DNA
<213> ORGANISM: Homo sapiens

<400> SEQUENCE: 15

```
cacaaaggat ccaggtctcc cgacgggagg ttaataccaa gaaccatgtg tgccgagcgg     60
ctgggccagt tcatgaccct ggctttggtg ttggccacct tgacccggc gcggggacc     120 gacgccacca acccacccga gggtccccaa gacaggagct cccagcagaa aggccgcctg   180
```

-continued

```
tccctgcaga atacagcgga gatccagcac tgtttggtca acgctggcga gtgggggtgt        240
ggcgtgtttg aatgtttcga gaacaactct tgtgagattc ggggcttaca tgggatttgc        300 atgactttc tgcacaacgc tggaaaattt gatgcccagg gcaagtcatt catcaaagac         360
gccttgaaat gtaaggccca cgctctgcgg cacaggttcg gctgcataag ccggaagtgc        420
ccggccatca gggaaatggt gtcccagttg cagcgggaat gctacctcaa gcacgacctg       480
tgcgcggctg cccaggagaa caccccgggtg atagtggaga tgatccattt caaggacttg      540
ctgctgcacg aaccctacgt ggacctcgtg aacttgctgc tgacctgtgg ggaggaggtg      600
aaggaggcca tcacccacag cgtgcaggtt cagtgtgagc agaactgggg aagcctgtgc      660
tccatcttga gcttctgcac ctcggccatc cagaagcctc ccacggcgcc ccccgagcgc      720
cagccccagg tggacagaac caagctctcc agggcccacc acgggtgct tggtgccaaa       780 ctgaaattca gtttcttgtg tgggggcctg cggttcagag ctcttggcga gggtggaggg      840
aggagtgtca tttctatgtg taatttctga gccattgtac tgtctgggct ggggggaca      900 ctgtccaagg gagtggcccc tatgagttta tattttaacc actgcttcaa atctcgattt     960 cactttttt atttatccag ttatatctac atatctgtca tctaaataaa tggctttcaa      1020
acaaagcaac tgggtcatta aaaccagctc aaaggggtt taaaaaaaaa aaa             1073
```

<210> SEQ ID NO 16
<211> LENGTH: 708
<212> TYPE: DNA
<213> ORGANISM: Homo sapiens

<400> SEQUENCE: 16

```
ccccgcaggc tgagggcagg tgggaagcaa acccggacgc atcgcagcag cagcagcagc       60
agcagaagca gcagcagcag cctccgcagt ccctccagag acatggatcc ccagacagca     120
ccttcccggg cgctcctgct cctgctcttc ttgcatctgg ctttcctggg aggtcgttcc     180
cacccgctgg gcagccccgg ttcagcctcg gacttggaaa cgtccgggtt acaggagcag    240
cgcaaccatt tgcagggcaa actgtcggag ctgcaggtgg agcagacatc cctggagccc     300
ctccaggaga gcccccgtcc cacaggtgtc tggaagtccc gggaggtagc caccgagggc    360
atccgtgggc accgcaaaat ggtcctctac acctgcgggg caccacgaag ccccaagatg    420
gtgcaagggt ctggctgctt tgggaggaag atggaccgga tcagctcctc cagtggcctg    480
ggctgcaaag tgctgaggcg gcattaagag gaagtcctgg ctgcagacac ctgcttctga    540
ttccacaagg ggcttttttcc tcaaccctgt ggccgccttt gaagtgactc attttttaa     600 tgtatttatg tatttatttg attgttttat ataagatggt ttcttacctt tgagcacaaa     660
atttccacgg tgaaataaag tcaacattat aagctttaaa aaaaaaaa                  708
```

<210> SEQ ID NO 17
<211> LENGTH: 905
<212> TYPE: DNA
<213> ORGANISM: Homo sapiens

<400> SEQUENCE: 17

```
ccccgcaggc tgagggcagg tgggaagcaa acccggacgc atcgcagcag cagcagcagc       60
agcagaagca gcagcagcag cctccgcagt ccctccagag acatggatcc ccagacagca     120
ccttcccggg cgctcctgct cctgctcttc ttgcatctgg ctttcctggg aggtcgttcc     180
cacccgctgg gcagccccgg ttcagcctcg gacttggaaa cgtccgggtt acaggagcag    240
```

```
cgcaaccatt tgcagggcaa actgtcggag ctgcaggtgg agcagacatc cctggagccc      300
ctccaggaga gcccccgtcc acaggtgtc tggaagtccc gggaggtagc caccgagggc       360
atccgtgggc accgcaaaat ggtcctctac accctgcggg caccacgaag ccccaagatg      420
gtgcaagggt ctggctgctt tgggaggaag atggaccgga tcagctcctc cagtggcctg      480
ggctgcaaag gtaagcaccc cctgccaccc cggccgcctt cccccattcc agtgtgtgac      540
actgttagag tcactttggg gtttgttgtc tctgggaacc acactctttg agaaaaggtc      600
acctggacat cgcttcctct tgttaacagc cttcagggcc aaggggtgcc tttgtggaat      660
tagtaaatgt gggcttattt cattaccatg cccacaatac cttctcccca cctcctactt      720
cttatcaaag gggcagaatc tcctttgggg gtctgtttat catttggcag ccccccagtg      780
gtgcagaaag agaaccaaac atttcctcct ggtttcctct aaactgtcta tagtctcaaa      840
ggcagagagc aggatcacca gagcaatgat aatccccaat ttacagatga ggaaactgag      900
gctca                                                                 905

<210> SEQ ID NO 18
<211> LENGTH: 817
<212> TYPE: DNA
<213> ORGANISM: Homo sapiens

<400> SEQUENCE: 18
agtcctgcgt ccgggccccg aggcgcagca gggcaccagg tggagcacca gctacgcgtg       60
gcgcagcgca gcgtccctag caccgagcct cccgcagccg ccgagatgct gcgaacagag      120
agctgccgcc ccaggtcgcc cgccggacag gtggccgcgg cgtccccgct cctgctgctg      180
ctgctgctgc tcgcctggtg cgcgggcgcc tgccgaggtg ctccaatatt acctcaagga      240
ttacagcctg aacaacagct acagttgtgg aatgagatag atgatacttg ttcgtctttt      300
ctgtccattg attctcagcc tcaggcatcc aacgcactgg aggagctttg ctttatgatt      360
atgggaatgc taccaaagcc tcaggaacaa gatgaaaaag ataatactaa aaggttctta      420
tttcattatt cgaagacaca gaagttgggc aagtcaaatg ttgtgtcgtc agttgtgcat      480
ccgttgctgc agctcgttcc tcacctgcat gagagaagaa tgaagagatt cagagtggac      540
gaagaattcc aaagtccctt tgcaagtcaa agtcgaggat atttttatt caggccacgg      600 aatggaagaa ggtcagcagg gttcatttaa aatggatgcc agctaatttt ccacagagca      660
atgctatgga atacaaaatg tactgacatt ttgttttctt ctgaaaaaaa tccttgctaa      720
atgtactctg ttgaaaatcc ctgtgttgtc aatgttctca gttgtaacaa tgttgtaaat      780
gttcaatttg ttgaaaatta aaaaatctaa aaataaa                              817

<210> SEQ ID NO 19
<211> LENGTH: 741
<212> TYPE: DNA
<213> ORGANISM: Homo sapiens

<400> SEQUENCE: 19
agtcctgcgt ccgggccccg aggcacagcc agggcaccag gtggagcacc agctacgcgt       60
ggcgcagcgc agcgtcccta gcaccgagcc tcccgcagcc gccgagatgc tgcgaacaga      120
gagctgccgc cccaggtcgc ccgccggaca ggtggccgcg gcgtcccgc tcctgctgct      180 gctgctgctg ctcgcctggt gcgcgggcgc ctgccgaggt gctccaatat tacctcaagg      240
attacagcct gaacaacagc tacagttgtg gaatgagata gatgatactt gttcgtcttt      300
tctgtccatt gattctcagc ctcaggcatc caacgcactg gaggagcttt gctttatgat      360
```

```
tatgggaatg ctaccaaagc ctcaggaaca agatgaaaaa gataatacta aaaggttctt    420
atttcattat tcgaagacac agaagttggg caagtcaaat gttgtggaag aattccaaag    480
tccctttgca agtcaaagtc gaggatatt tttattcagg ccacggaatg aagaaggtc     540 agcagggttc atttaaaatg gatgccagct aattttccac agagcaatgc tatggaatac    600
aaaatgtact gacattttgt tttcttctga aaaaaatcct tgctaaatgt actctgttga    660
aaatccctgt gttgtcaatg ttctcagttg taacaatgtt gtaaatgttc aatttgttga    720
aaattaaaaa atctaaaaat a                                              741
```

```
<210> SEQ ID NO 20
<211> LENGTH: 180
<212> TYPE: PRT
<213> ORGANISM: Homo sapiens

<400> SEQUENCE: 20

Met Lys Ser Ile Tyr Phe Val Ala Gly Leu Phe Val Met Leu Val Gln
1               5                   10                  15

Gly Ser Trp Gln Gln Asp Thr Glu Glu Lys Ser Arg Ser Leu Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 21
<211> LENGTH: 129
<212> TYPE: PRT
<213> ORGANISM: Homo sapiens

<400> SEQUENCE: 21

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60
```

```
Tyr Leu Asp Ser Arg Arg Ala Gln Asp Phe Val Gln Trp Leu Met Asn
 65                  70                  75                  80

Thr Lys Arg Asn Arg Asn Asn Ile Ala Lys Arg His Asp Glu Phe Glu
                 85                  90                  95

Arg His Ala Glu Gly Thr Phe Thr Ser Val Ser Gln Lys Arg Ser Pro
            100                 105                 110

Leu Leu Lys Asn Leu Ala Ala Asp Met Leu Met Val Leu Ser Leu Met
        115                 120                 125

Arg

<210> SEQ ID NO 22
<211> LENGTH: 170
<212> TYPE: PRT
<213> ORGANISM: Homo sapiens

<400> SEQUENCE: 22

Met Met Ala Gly Met Lys Ile Gln Leu Val Cys Met Leu Leu Leu Ala
  1               5                  10                  15

Phe Ser Ser Trp Ser Leu Cys Ser Asp Ser Glu Glu Met Lys Ala
                 20                  25                  30

Leu Glu Ala Asp Phe Leu Thr Asn Met His Thr Ser Lys Ile Ser Lys
             35                  40                  45

Ala His Val Pro Ser Trp Lys Met Thr Leu Leu Asn Val Cys Ser Leu
         50                  55                  60

Val Asn Asn Leu Asn Ser Pro Ala Glu Glu Thr Gly Glu Val His Glu
 65                  70                  75                  80

Glu Glu Leu Val Ala Arg Arg Lys Leu Pro Thr Ala Leu Asp Gly Phe
                 85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Glu Val Ile Lys Arg Lys Ile
    130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr
                165                 170

<210> SEQ ID NO 23
<211> LENGTH: 159
<212> TYPE: PRT
<213> ORGANISM: Homo sapiens

<400> SEQUENCE: 23

Met Met Ala Gly Met Lys Ile Gln Leu Val Cys Met Leu Leu Leu Ala
  1               5                  10                  15

Phe Ser Ser Trp Ser Leu Cys Ser Asp Ser Glu Glu Met Lys Ala
                 20                  25                  30

Leu Glu Ala Asp Phe Leu Thr Asn Met His Thr Ser Lys Ile Ser Lys
             35                  40                  45

Ala His Val Pro Ser Trp Lys Met Thr Leu Leu Asn Val Cys Ser Leu
         50                  55                  60

Val Asn Asn Leu Asn Ser Pro Ala Glu Glu Thr Gly Glu Val His Glu
 65                  70                  75                  80

Glu Glu Leu Val Ala Arg Arg Lys Leu Pro Thr Ala Leu Asp Gly Phe
```

```
                        85                  90                  95
Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Glu Val Ile Lys Arg Lys Ile
    130                 135                 140

Pro Tyr Ile Leu Lys Arg Gln Gln Ala Thr Cys Ala Arg Ala Val
145                 150                 155

<210> SEQ ID NO 24
<211> LENGTH: 95
<212> TYPE: PRT
<213> ORGANISM: Homo sapiens

<400> SEQUENCE: 24

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
            20                  25                  30

Leu Glu Ala Asp Phe Leu Thr Asn Met His Thr Ser Lys Leu Ile Gln
        35                  40                  45

Glu Asp Ile Leu Asp Thr Gly Asn Asp Lys Asn Gly Lys Glu Glu Val
    50                  55                  60

Ile Lys Arg Lys Ile Pro Tyr Ile Leu Lys Arg Gln Leu Tyr Glu Asn
65                  70                  75                  80

Lys Pro Arg Arg Pro Tyr Ile Leu Lys Arg Asp Ser Tyr Tyr Tyr
                85                  90                  95

<210> SEQ ID NO 25
<211> LENGTH: 95
<212> TYPE: PRT
<213> ORGANISM: Homo sapiens

<400> SEQUENCE: 25

Met Ala Ala Ala Arg Leu Cys Leu Ser Leu Leu Leu Leu Ser Thr Cys
1               5                   10                  15

Val Ala Leu Leu Leu Gln Pro Leu Leu Gly Ala Gln Gly Ala Pro Leu
            20                  25                  30

Glu Pro Val Tyr Pro Gly Asp Asn Ala Thr Pro Glu Gln Met Ala Gln
        35                  40                  45

Tyr Ala Ala Asp Leu Arg Arg Tyr Ile Asn Met Leu Thr Arg Pro Arg
    50                  55                  60

Tyr Gly Lys Arg His Lys Glu Asp Thr Leu Ala Phe Ser Glu Trp Gly
65                  70                  75                  80

Ser Pro His Ala Ala Val Pro Arg Glu Leu Ser Pro Leu Asp Leu
                85                  90                  95

<210> SEQ ID NO 26
<211> LENGTH: 105
<212> TYPE: PRT
<213> ORGANISM: Homo sapiens

<400> SEQUENCE: 26

Met Ala Ala Ala Arg Leu Cys Leu Ser Leu Leu Leu Leu Ser Thr Cys
1               5                   10                  15

Val Ala Leu Leu Leu Gln Pro Leu Leu Gly Ala Gln Gly Ala Pro Leu
            20                  25                  30
```

Glu Pro Val Tyr Pro Gly Asp Asn Ala Thr Pro Glu Gln Met Ala Gln
                35                  40                  45

Tyr Ala Ala Asp Leu Arg Arg Tyr Ile Asn Met Leu Thr Arg Pro Ser
    50                  55                  60

Ala Cys Pro Cys Cys Leu Phe Pro Pro Arg Tyr Gly Lys Arg His Lys
65                  70                  75                  80

Glu Asp Thr Leu Ala Phe Ser Glu Trp Gly Ser Pro His Ala Ala Val
                85                  90                  95

Pro Arg Glu Leu Ser Pro Leu Asp Leu
            100                 105

<210> SEQ ID NO 27
<211> LENGTH: 116
<212> TYPE: PRT
<213> ORGANISM: Homo sapiens

<400> SEQUENCE: 27

Met Glu Ser Ser Arg Val Arg Leu Leu Pro Leu Leu Gly Ala Ala Leu
1               5                   10                  15

Leu Leu Met Leu Pro Leu Leu Gly Thr Arg Ala Gln Glu Asp Ala Glu
                20                  25                  30

Leu Gln Pro Arg Ala Leu Asp Ile Tyr Ser Ala Val Asp Asp Ala Ser
            35                  40                  45

His Glu Lys Glu Leu Ile Glu Ala Leu Gln Glu Val Leu Lys Lys Leu
        50                  55                  60

Lys Ser Lys Arg Val Pro Ile Tyr Glu Lys Lys Tyr Gly Gln Val Pro
65                  70                  75                  80

Met Cys Asp Ala Gly Glu Gln Cys Ala Val Arg Lys Gly Ala Arg Ile
                85                  90                  95

Gly Lys Leu Cys Asp Cys Pro Arg Gly Thr Ser Cys Asn Ser Phe Leu
            100                 105                 110

Leu Lys Cys Leu
        115

<210> SEQ ID NO 28
<211> LENGTH: 91
<212> TYPE: PRT
<213> ORGANISM: Homo sapiens

<400> SEQUENCE: 28

Met Glu Ser Ser Arg Val Arg Leu Leu Pro Leu Leu Gly Ala Ala Leu
1               5                   10                  15

Leu Leu Met Leu Pro Leu Leu Gly Thr Arg Ala Gln Glu Asp Ala Glu
                20                  25                  30

Leu Gln Pro Arg Ala Leu Asp Ile Tyr Ser Ala Val Asp Asp Ala Ser
            35                  40                  45

His Glu Lys Glu Leu Val Gly Ile Pro Leu Ala Leu Asp Pro Leu Glu
        50                  55                  60

Leu Ser Pro Cys Leu Phe Ser Cys Thr Pro Pro Ser Ser Pro His Pro
65                  70                  75                  80

His Ser Tyr Ser Gln Ser Gln Gly Ala Gly Ser
                85                  90

<210> SEQ ID NO 29
<211> LENGTH: 124
<212> TYPE: PRT
<213> ORGANISM: Homo sapiens

<400> SEQUENCE: 29

Met Arg Gln Ala Gly Arg Ala Ala Leu Leu Ala Ala Leu Leu Leu Leu
1               5                   10                  15

Val Gln Leu Cys Pro Gly Ser Ser Gln Arg Ser Pro Glu Ala Ala Gly
            20                  25                  30

Val Gln Asp Pro Ser Leu Arg Trp Ser Pro Gly Ala Arg Asn Gln Gly
        35                  40                  45

Gly Gly Ala Arg Ala Leu Leu Leu Leu Ala Glu Arg Phe Pro Arg
    50                  55                  60

Arg Ala Gly Pro Gly Arg Leu Gly Leu Gly Thr Ala Gly Glu Arg Pro
65                  70                  75                  80

Arg Arg Asp Asn Pro Ser Leu Ser Ile Asp Leu Thr Phe His Leu Leu
                85                  90                  95

Arg Thr Leu Leu Glu Leu Ala Arg Thr Gln Ser Gln Arg Glu Arg Ala
            100                 105                 110

Glu Gln Asn Arg Ile Ile Phe Asp Ser Val Gly Lys
            115                 120

<210> SEQ ID NO 30
<211> LENGTH: 81
<212> TYPE: PRT
<213> ORGANISM: Homo sapiens

<400> SEQUENCE: 30

Met Arg Gln Ala Gly Arg Ala Ala Leu Leu Ala Ala Leu Leu Leu Leu
1               5                   10                  15

Val Gln Leu Cys Pro Gly Ser Ser Gln Arg Ser Pro Glu Ser Ala Leu
            20                  25                  30

Glu Pro Arg Gly Thr Glu Pro Gly Trp Arg Gly Pro Arg Ala Pro Leu
        35                  40                  45

Ala Ala Gly Gly Ala Leu Pro Ala Pro Arg Gly Ala Arg Pro Ile Gly
    50                  55                  60

Thr Arg Asp Gly Arg Arg Ala Ala Ala Gly Gln Pro Phe Ser Val
65                  70                  75                  80

His

<210> SEQ ID NO 31
<211> LENGTH: 267
<212> TYPE: PRT
<213> ORGANISM: Homo sapiens

<400> SEQUENCE: 31

Met Ala Arg Phe Leu Thr Leu Cys Thr Trp Leu Leu Leu Leu Gly Pro
1               5                   10                  15

Gly Leu Leu Ala Thr Val Arg Ala Glu Cys Ser Gln Asp Cys Ala Thr
            20                  25                  30

Cys Ser Tyr Arg Leu Val Arg Pro Ala Asp Ile Asn Phe Leu Ala Cys
        35                  40                  45

Val Met Glu Cys Glu Gly Lys Leu Pro Ser Leu Lys Ile Trp Glu Thr
    50                  55                  60

Cys Lys Glu Leu Leu Gln Leu Ser Lys Pro Glu Leu Pro Gln Asp Gly
65                  70                  75                  80

Thr Ser Thr Leu Arg Glu Asn Ser Lys Pro Glu Glu Ser His Leu Leu
                85                  90                  95

Ala Lys Arg Tyr Gly Gly Phe Met Lys Arg Tyr Gly Gly Phe Met Lys

-continued

```
                100                 105                 110
Lys Met Asp Glu Leu Tyr Pro Met Glu Pro Glu Glu Ala Asn Gly
            115                 120                 125
Ser Glu Ile Leu Ala Lys Arg Tyr Gly Gly Phe Met Lys Lys Asp Ala
    130                 135                 140
Glu Glu Asp Asp Ser Leu Ala Asn Ser Ser Asp Leu Leu Lys Glu Leu
145                 150                 155                 160
Leu Glu Thr Gly Asp Asn Arg Glu Arg Ser His His Gln Asp Gly Ser
                165                 170                 175
Asp Asn Glu Glu Glu Val Ser Lys Arg Tyr Gly Gly Phe Met Arg Gly
            180                 185                 190
Leu Lys Arg Ser Pro Gln Leu Glu Asp Glu Ala Lys Glu Leu Gln Lys
        195                 200                 205
Arg Tyr Gly Gly Phe Met Arg Arg Val Gly Arg Pro Glu Trp Trp Met
    210                 215                 220
Asp Tyr Gln Lys Arg Tyr Gly Gly Phe Leu Lys Arg Phe Ala Glu Ala
225                 230                 235                 240
Leu Pro Ser Asp Glu Glu Gly Glu Ser Tyr Ser Lys Glu Val Pro Glu
                245                 250                 255
Met Glu Lys Arg Tyr Gly Gly Phe Met Arg Phe
            260                 265

<210> SEQ ID NO 32
<211> LENGTH: 218
<212> TYPE: PRT
<213> ORGANISM: Homo sapiens

<400> SEQUENCE: 32

Met Glu Cys Glu Gly Lys Leu Pro Ser Leu Lys Ile Trp Glu Thr Cys
1               5                   10                  15
Lys Glu Leu Leu Gln Leu Ser Lys Pro Glu Leu Pro Gln Asp Gly Thr
            20                  25                  30
Ser Thr Leu Arg Glu Asn Ser Lys Pro Glu Glu Ser His Leu Leu Ala
        35                  40                  45
Lys Arg Tyr Gly Gly Phe Met Lys Arg Tyr Gly Gly Phe Met Lys Lys
    50                  55                  60
Met Asp Glu Leu Tyr Pro Met Glu Pro Glu Glu Ala Asn Gly Ser
65                  70                  75                  80
Glu Ile Leu Ala Lys Arg Tyr Gly Gly Phe Met Lys Lys Asp Ala Glu
                85                  90                  95
Glu Asp Asp Ser Leu Ala Asn Ser Ser Asp Leu Leu Lys Glu Leu Leu
            100                 105                 110
Glu Thr Gly Asp Asn Arg Glu Arg Ser His His Gln Asp Gly Ser Asp
        115                 120                 125
Asn Glu Glu Glu Val Ser Lys Arg Tyr Gly Gly Phe Met Arg Gly Leu
    130                 135                 140
Lys Arg Ser Pro Gln Leu Glu Asp Glu Ala Lys Glu Leu Gln Lys Arg
145                 150                 155                 160
Tyr Gly Gly Phe Met Arg Arg Val Gly Arg Pro Glu Trp Trp Met Asp
                165                 170                 175
Tyr Gln Lys Arg Tyr Gly Gly Phe Leu Lys Arg Phe Ala Glu Ala Leu
            180                 185                 190
Pro Ser Asp Glu Glu Gly Glu Ser Tyr Ser Lys Glu Val Pro Glu Met
        195                 200                 205
```

```
Glu Lys Arg Tyr Gly Gly Phe Met Arg Phe
    210                 215
```

```
<210> SEQ ID NO 33
<211> LENGTH: 302
<212> TYPE: PRT
<213> ORGANISM: Homo sapiens

<400> SEQUENCE: 33

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
    130                 135                 140

Leu Cys Ala Ala Ala Gln Glu Asn Thr Arg Val Ile Val Glu Met Ile
145                 150                 155                 160

His Phe Lys Asp Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
        275                 280                 285

Glu Trp Glu Asp Glu Gln Ser Glu Tyr Ser Asp Ile Arg Arg
    290                 295                 300

<210> SEQ ID NO 34
<211> LENGTH: 274
<212> TYPE: PRT
<213> ORGANISM: Homo sapiens

<400> SEQUENCE: 34

Met Cys Ala Glu Arg Leu Gly Gln Phe Met Thr Leu Ala Leu Val Leu
1               5                   10                  15
```

```
Ala Thr Phe Asp Pro Ala Arg Gly Thr Asp Ala Thr Asn Pro Pro Glu
            20                  25                  30

Gly Pro Gln Asp Arg Ser Ser Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
            115                 120                 125

Arg Glu Met Val Ser Gln Leu Gln Arg Glu Cys Tyr Leu Lys His Asp
130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
            195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Val Leu Gly Ala Lys Leu Lys Phe Ser Phe Leu Cys Gly Ala Leu Arg
                245                 250                 255

Phe Arg Ala Leu Gly Glu Gly Gly Arg Ser Val Ile Ser Met Cys
            260                 265                 270

Asn Phe

<210> SEQ ID NO 35
<211> LENGTH: 134
<212> TYPE: PRT
<213> ORGANISM: Homo sapiens

<400> SEQUENCE: 35

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110
```

```
Phe Gly Arg Lys Met Asp Arg Ile Ser Ser Ser Ser Gly Leu Gly Cys
        115                 120                 125

Lys Val Leu Arg Arg His
    130

<210> SEQ ID NO 36
<211> LENGTH: 162
<212> TYPE: PRT
<213> ORGANISM: Homo sapiens

<400> SEQUENCE: 36

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Gly Lys His Pro Leu Pro Pro Arg Pro Pro Ser Pro Ile Pro Val
    130                 135                 140

Cys Asp Thr Val Arg Val Thr Leu Gly Phe Val Ser Gly Asn His
145                 150                 155                 160

Thr Leu

<210> SEQ ID NO 37
<211> LENGTH: 174
<212> TYPE: PRT
<213> ORGANISM: Homo sapiens

<400> SEQUENCE: 37

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
            20                  25                  30

Ala Gly Ala Cys Arg Gly Ala Pro Ile Leu Pro Gln Gly Leu Gln Pro
        35                  40                  45

Glu Gln Gln Leu Gln Leu Trp Asn Glu Ile Asp Asp Thr Cys Ser Ser
    50                  55                  60

Phe Leu Ser Ile Asp Ser Gln Pro Gln Ala Ser Asn Ala Leu Glu Glu
65                  70                  75                  80

Leu Cys Phe Met Ile Met Gly Met Leu Pro Lys Pro Gln Glu Gln Asp
                85                  90                  95

Glu Lys Asp Asn Thr Lys Arg Phe Leu Phe His Tyr Ser Lys Thr Gln
            100                 105                 110

Lys Leu Gly Lys Ser Asn Val Val Ser Ser Val Val His Pro Leu Leu
        115                 120                 125

Gln Leu Val Pro His Leu His Glu Arg Arg Met Lys Arg Phe Arg Val
```

```
                130             135             140
Asp Glu Glu Phe Gln Ser Pro Phe Ala Ser Gln Ser Arg Gly Tyr Phe
145                 150                 155                 160

Leu Phe Arg Pro Arg Asn Gly Arg Arg Ser Ala Gly Phe Ile
                165                 170

<210> SEQ ID NO 38
<211> LENGTH: 149
<212> TYPE: PRT
<213> ORGANISM: Homo sapiens

<400> SEQUENCE: 38

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
                20                  25                  30

Ala Gly Ala Cys Arg Gly Ala Pro Ile Leu Pro Gln Gly Leu Gln Pro
                35                  40                  45

Glu Gln Gln Leu Gln Leu Trp Asn Glu Ile Asp Asp Thr Cys Ser Ser
        50                  55                  60

Phe Leu Ser Ile Asp Ser Gln Pro Gln Ala Ser Asn Ala Leu Glu Glu
65                  70                  75                  80

Leu Cys Phe Met Ile Met Gly Met Leu Pro Lys Pro Gln Glu Gln Asp
                85                  90                  95

Glu Lys Asp Asn Thr Lys Arg Phe Leu Phe His Tyr Ser Lys Thr Gln
            100                 105                 110

Lys Leu Gly Lys Ser Asn Val Val Glu Glu Phe Gln Ser Pro Phe Ala
        115                 120                 125

Ser Gln Ser Arg Gly Tyr Phe Leu Phe Arg Pro Arg Asn Gly Arg Arg
    130                 135                 140

Ser Ala Gly Phe Ile
145
```